United States Patent
Gangoiti Munecas et al.

(10) Patent No.: US 10,626,428 B2
(45) Date of Patent: Apr. 21, 2020

(54) BRANCHED ALPHA GLUCANS

(71) Applicant: NESTEC S.A., Vevey (CH)

(72) Inventors: Joana Gangoiti Munecas, AG Groningen (NL); Sander Sebastiaan Van Leeuwen, AG Groningen (NL); Lubbert Dijkhuizen, AG Groningen (NL); Christina Vafeiadi, Lausanne (CH); Lisa Lamothe, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/758,443

(22) PCT Filed: Sep. 12, 2016

(86) PCT No.: PCT/EP2016/071474
§ 371 (c)(1),
(2) Date: Mar. 8, 2018

(87) PCT Pub. No.: WO2017/046040
PCT Pub. Date: Mar. 23, 2017

(65) Prior Publication Data
US 2019/0119712 A1 Apr. 25, 2019

(30) Foreign Application Priority Data

Sep. 15, 2015 (EP) .................................... 15185336

(51) Int. Cl.
| | |
|---|---|
| *C12P 19/18* | (2006.01) |
| *C12P 19/04* | (2006.01) |
| *A23L 33/125* | (2016.01) |
| *A23L 33/21* | (2016.01) |
| *A23L 29/225* | (2016.01) |
| *A23L 29/212* | (2016.01) |
| *A61K 31/715* | (2006.01) |
| *A23K 20/163* | (2016.01) |
| *A23L 33/10* | (2016.01) |
| *A23L 33/26* | (2016.01) |
| *A61K 31/716* | (2006.01) |
| *C08B 37/00* | (2006.01) |

(52) U.S. Cl.
CPC ............ *C12P 19/04* (2013.01); *A23K 20/163* (2016.05); *A23L 29/212* (2016.08); *A23L 29/225* (2016.08); *A23L 33/10* (2016.08); *A23L 33/125* (2016.08); *A23L 33/21* (2016.08); *A23L 33/26* (2016.08); *A61K 31/715* (2013.01); *A61K 31/716* (2013.01); *C08B 37/0009* (2013.01); *C12P 19/18* (2013.01); *C12Y 204/01025* (2013.01); *A23V 2002/00* (2013.01)

(58) Field of Classification Search
None
See application file for complete search history.

(56) References Cited

FOREIGN PATENT DOCUMENTS

| | | |
|---|---|---|
| EP | 1943908 | 7/2008 |
| WO | 0190372 | 11/2001 |
| WO | 2004022076 | 3/2004 |

OTHER PUBLICATIONS

Roussel et al. "Characterization of substrate and product specificity of the purified recombinant glycogen branching enzyme of Rhodothermus obamensis" Biochemica et Biophysica Acta, 2013, vol. 1830, pp. 2167-2177, XP055317446.
Grimaud et al. "In Vitro Synthesis of Hyperbranched Alpha-Glucans Using a Biomimetic Enzymatic Toolbox" Biomacromolecules, 2013, vol. 14, pp. 438-447.
Kajiura et al "A novel enzymatic process for glycogen production" Biocatalysis and Biotransformation, Jan.-Feb. 2008, vol. 2016, No. 1-2, pp. 133-140.
Van Leeuwen et al. "Structural analysis of the alpha-d-glucan (EPS35-5) produced by the Lactobacillus reuteri strain 35-5 glucansucrase GTFA enzyme" Carbohydrate Research, 2008, vol. 343, pp. 1251-1265, XP022611143.
Anonymous "Uniprot:A0A0C4W IK3", Apr. 29, 2015, retrieved from the Internet at http://ibis.internal.epo.org/exam/dbfetch.jsp?id=Uniprot:AOAOC4WTK3 [retrieved on Mar. 2, 2016], XP055254786, 1 page.
Wang et al. "*Paenibacillus beijingensis* sp. nov., a nitrogen-fixing species isolated from what rhizosphere soil" Antoine van Leeuwenhoek, 2013, vol. 104, pp. 675-683, XF055317405.

*Primary Examiner* — Rebecca E Prouty
(74) *Attorney, Agent, or Firm* — K&L Gates LLP

(57) ABSTRACT

The present invention relates to the field of poly- and oligosaccharides and their dietary effects. In particular it relates to a method of producing a branched α-glucan. Further aspects of the invention are a branched α-glucan comprising alternating α(1→4) and α(1→6) glucosidic linkages and having α(1→4,6) branching points, a food composition, and the use of an α-glucanotransferase enzyme for reducing the digestible carbohydrates of a starch containing food material.

11 Claims, 19 Drawing Sheets
Specification includes a Sequence Listing.

Fig. 3

| Bacterial strain | NCBI accesion numbers | Motif I | | Motif II | | Motif III | | Motif IV | |
|---|---|---|---|---|---|---|---|---|---|
| A | | | 1 2 | | 3 4 | | 5 | | 6 7 |
| Azotobacter chroococcum NCIMB 8003 | AJE22990.1 | 202 | VDVVPNQ | 465 | FDGFRIDAASHIN | 500 | HLSYIESYVTQ | 567 | FVNNHDQE-HNILVTV |
| B | | | | | | | | | |
| Exiguobacterium sibiricum 255-15 | WP_012371512.1 | 138 | MDLVPNQ | 401 | FDGFRIDAASHYD | 433 | HLSYIESYKSE | 504 | FVNNHDQE-KNRVNQI |
| Exiguobacterium undae | WP_028105602.1 | 138 | MDLVPNQ | 401 | FDGFRIDAASHYD | 433 | HLSYIESYKSE | 504 | FVNNHDQE-KNRVNQI |
| Exiguobacterium antarcticum B7 | WP_014971370.1 | 138 | MDLVPNQ | 401 | FDGFRIDAASHYD | 433 | HLSYIESYKSE | 504 | FVNNHDQE-KNRVNQI |
| Exiguobacterium acetylicum | WP_029342707.1 | 138 | MDLVPNQ | 401 | FDGFRIDAASHYD | 433 | YLSYIESYKTE | 503 | FVNNHDQE-KNRVNQI |
| Bacillus kribbensis | WP_026693127.1 | 130 | EDLVPNQ | 395 | FDGFRIDAASHYD | 429 | HLSYIESYSNV | 491 | FVNNHDQE-KNRVNNI |
| Bacillus coagulans DSM1 | WP_035180801.1 | 128 | EDLVPNQ | 392 | FDGFRIDAAGHYD | 426 | HLSYIESIQSA | 497 | FVNNHDQE-KNRVNKI |
| C | | | | | | | | | |
| Lactobacillus reuteri 121 (GTFB) | AAU08014.2 | 1478 | EDIVMNQ | 1009 | FDGFRVDAADNID | 1048 | HLSYNEGYHSG | 1120 | FVTNHDQR-KNLINRL |
| Lactobacillus reuteri ML1 (ML4) | AAU08003.2 | 1479 | EDIVMNQ | 1010 | FDGFRVDAADNID | 1049 | HLSYNEGYHSG | 1121 | FVTNHDQR-KNLINRL |
| Lactobacillus salivarius GJ-24 | EGM52218.1 | 1485 | VDIVMNQ | 1024 | FDGFRIDAADHID | 1063 | HLSYNEGYRSG | 1134 | YVTNHDQR-KNLINGL |
| Pediococcus pentosaceus IE-3 | WP_036673144.1 | 841 | EDIVMNQ | 378 | FDGFRIDAADNID | 417 | HLSYNEGYHSG | 489 | FVTNHDQR-KNLINSL |
| Lactobacillus plantarum 16 | WP_016526729.1 | 1201 | EDLVMNQ | 747 | FDGFRVDAADHID | 786 | HLVYNEGYNYG | 859 | FVTNHDQR-KNLVNRI |
| Lactobacillus reuteri DSM 20016 (GTFW) | WP_011953522.1 | 1215 | EDLVMNQ | 746 | FDGFRVDAADNID | 785 | HLVYNEGYHSG | 858 | FVTNHDQR-KNVINQI |
| Lactobacillus acidipiscis KCTC 13900 | WP_035631372.1 | 765 | VDMVMNQ | 294 | FDGFRNDAADNID | 333 | HLVYNEGYHSG | 406 | FVTNHDQR-KNVINQI |
| D | | | | | | | | | |
| Lactobacillus reuteri 180 (GTF180) | AAU08001.1 | 1503 | ADWVPDQ | 1019 | FDGIRVDAVDNVD | 1058 | HINILEDWGWD | 1131 | FVRAHDSNAQDQIRQA |
| Lactobacillus reuteri 121 (GTFA) | AAU08015.1 | 1508 | ADWVPDQ | 1018 | FDSVRVDAPDNID | 1056 | HINILEDWNHA | 1128 | FVRAHDNNSQDQIQNA |
| Streptococcus mutants Si (GTFSI) | BAA26114.1 | 954 | ADWVPDQ | 471 | FDSIRVDAVDNVD | 510 | HLSILEAWSYN | 583 | FIRAHDSEVQDLIRDI |
| Leuconostoc mesenteroides NRRL B-1299 | BN964_01272 | 2688 | ADVVDNQ | 2204 | FDSIRIDAVDFIH | 2243 | HISLVEAGLDA | 2317 | IIHAHDKGVQEKVGAA |
| E | | | | | | | | | |
| Bacillus sterothermophilus (BSTA) | P06279.3 | 134 | ADVVFDH | 262 | IDGFRLDAVKHIK | 293 | LFTVGEYWSYD | 360 | FVDNHDTEPGQALQSW |
| Bacillus licheniformis (BLA) | WP_025807921.1 | 128 | GDVVIHH | 254 | LDGFRLDAVKHIK | 285 | MFTVAEYWQND | 352 | FVDNHDTQPGQSLEST |
| Bacillus sp. 707 | P19571.1 | 134 | GDVVMNH | 263 | LDGFRIDAVKHIK | 294 | MFAVAEFWKND | 362 | FVDNHDSQPEEALESF |
| Halothermothrix orenii (AmyB) | WP_015923543.1 | 251 | FDAVLNH | 368 | FDGFRLDAVKHID | 399 | VFFVGEAWVED | 466 | FVDNEDEDRDEGSYTV |
| | | | -1 | | -1  +1+1 | | +1  +2 | | -1 +2+2 -1 |
| | | | | | ▲ NU | | ▲ A/B | | ▲ TS |

Fig. 4

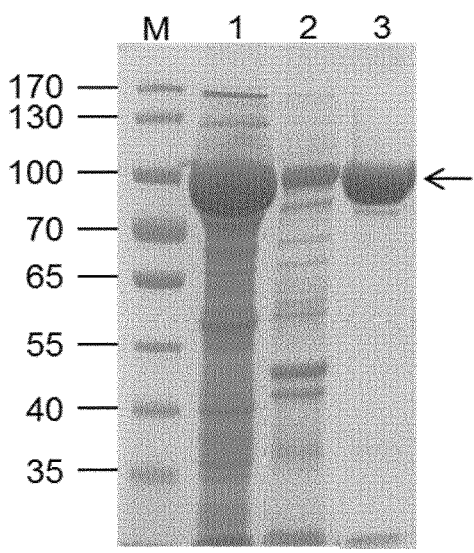

| Bacterial strain | Accession numbers[a] | Motif I | Motif II | Motif III | Motif IV |
|---|---|---|---|---|---|
| A | | 1  2 | 3 4 | 5 | 6 7 |
| *Paenibacillus beijingensis* | WP_045672861.1 | 145 VDLVPNQ | 405 GFRIDAASHYN | 437 HLSYIESYTDN | 507 FVMNHDQE-HNGIKG |
| *Azotobacter chroococcum* NCIMB 8003 | AJE22990.1 | 202 VDVVPNQ | 467 GFRIDAASHIN | 500 HLSYIESYVTQ | 567 FVNNHDQE-HNILVT |
| | | | NU | A/B | TS |

SEQUENCE LISTING

```
<160> NUMBER OF SEQ ID NOS: 98

<210> SEQ ID NO 1
<211> LENGTH: 780
<212> TYPE: PRT
<213> ORGANISM: Azotobacter chroococcum

<400> SEQUENCE: 1

Met Arg Ala Ser Pro Ser Gln Phe Phe Ala Ile Ser Leu Leu Ser Ile
1               5                   10                  15

Ala Ile Ser Gly Leu Leu Ser Gly Ala Ala Val Ala Ala Pro Ala Pro
            20                  25                  30

Thr Ala Leu Glu Gln Val Pro Asp Gly Lys Gly Gly Val Lys Trp Gln
        35                  40                  45

Glu Val Thr His Asp Ala Ser Ala Glu Glu Gln Lys Gly Gln Asp
    50                  55                  60

Pro Lys Lys Phe Leu Gly Ile Gln Ala Ile Thr Thr Glu Pro Asp Gly
65                  70                  75                  80

Ser Val Lys Val Glu Met Gly Lys Pro Glu Val Arg Gln Pro Ala Ser
                85                  90                  95

Gly Asp Val Phe Val Ser Asn Glu Lys Leu Asp Glu His Val Ile Phe
            100                 105                 110

Gln Ala Phe Ala Leu Tyr Gln Pro Asn Asp Asn Ala Thr Tyr Lys Ala
        115                 120                 125

Leu Thr Glu Asn Ala Pro Gln Leu Ala Gln Trp Gly Ile Thr Asp Val
    130                 135                 140

Trp Ser Pro Pro Tyr Arg Ala Ala Ser Asp Ser Lys Tyr Gly Glu
145                 150                 155                 160

Gly Tyr Ala Ile Ala Asp Arg Tyr Asp Leu Gly Ala Tyr Asp Lys Gly
                165                 170                 175

Pro Thr Lys Tyr Gly Thr Ala Asp Glu Leu Lys Ala Ala Ile Gly Ala
            180                 185                 190

Leu His Asn Asn Asp Ile Arg Ile Gln Val Asp Val Val Pro Asn Gln
        195                 200                 205

Ile Ile Gly Leu Asn Glu Arg His Val Leu Pro Val Thr Gly Val Asp
    210                 215                 220

Met Tyr Gly Lys Pro Met Asn Pro Phe Leu Asp His Tyr Leu Tyr Ser
225                 230                 235                 240

Thr Tyr Ser Lys Gly Ser Ala Pro Gly Gln Ala Glu His Gly Val Ile
                245                 250                 255

Lys Glu Trp Asp Tyr Phe His Phe Gly Thr Thr Gln Tyr Gln
            260                 265                 270

Gly Leu Phe Arg Val Leu Ser Asp Ala Asn Ser Thr Leu Tyr Arg Tyr
        275                 280                 285

Leu Gly Pro Asn His Pro Glu Asn Tyr Leu Pro Ala Phe Leu Ala Glu
```

```
             290                 295                 300
Ser Asp Ala Ala Lys Tyr Gly Lys Ile Asn Thr Ile Asp Gly Tyr Leu
305                 310                 315                 320

Leu Ala Asp Thr Trp Phe Ala Val Glu Asn Ala Glu Ser Glu Asn Ala
                325                 330                 335

Val Tyr Ala Pro Leu Phe Leu Tyr Tyr Glu Pro Arg Asn Gly Val
                340                 345                 350

Val Glu Gln Thr Phe Met Asp Phe Ala Arg Glu Asn Gly Tyr Thr Gly
                355                 360                 365

Ser Asp Glu Asp Ile Arg Ala Thr Met Leu Ala Glu Leu Arg Met Thr
370                 375                 380

Pro Asn Pro Ile Gly Pro Leu Met Asp Glu Tyr Leu Ala Ala Gln Pro
385                 390                 395                 400

Gly Tyr Ser Lys Lys Ser Glu Asp Ala Lys Val Thr Ala Leu Arg
                405                 410                 415

Tyr Asp Gly Pro Glu Asn Asp Ala Ser His Ile Gly Thr Asn Val Leu
                420                 425                 430

Asp Phe Glu Phe Leu Val Gly Asn Asp Leu Asp Thr Ile Arg Glu Asp
                435                 440                 445

Val Gln Gln Glu Gln Leu Asn Trp Gln Lys Tyr Leu Leu Asp Phe Gly
450                 455                 460

Phe Asp Gly Phe Arg Ile Asp Ala Ala Ser His Ile Asn Thr Asp Met
465                 470                 475                 480

Leu Arg Asp Glu Val Thr Gln Arg Leu Asn His Phe Ala Gly Glu Asp
                485                 490                 495

Val Asn Glu His Leu Ser Tyr Ile Glu Ser Tyr Val Thr Gln Gln Val
                500                 505                 510

Asp Phe Leu Gln Ser Asn Asn Tyr Gly Gln Met Ala Met Asp Ala Gly
                515                 520                 525

Pro Phe Ser Gly Leu Met Phe Ser Phe Gly Arg Asp Trp Ala Pro Leu
                530                 535                 540

Arg Tyr Ala Phe Glu Ala Ser Leu Ile Asp Arg Val Asn Gly Gly Pro
545                 550                 555                 560

Ala Leu Pro Asn Trp Ser Phe Val Asn Asn His Asp Gln Glu His Asn
                565                 570                 575

Ile Leu Val Thr Val Pro Leu Thr Glu Glu Ala Gly Gly Tyr Glu
                580                 585                 590

Pro Asn Ser Gln Pro Tyr Glu Leu Arg Gln Leu Glu Lys Tyr Asp Ala
                595                 600                 605

Asp Arg Asn Ser Val Glu Lys Gln Trp Ala Pro His Asn Val Pro Ala
610                 615                 620

Met Tyr Ala Ile Leu Leu Thr Thr Lys Asp Thr Val Pro Thr Val Phe
625                 630                 635                 640

Tyr Gly Asp Met Phe Val Ser Ser Lys Pro Tyr Met Ser Thr Pro Thr
                645                 650                 655

Pro Tyr Arg Asp Asp Ile Val Asn Ile Leu Lys Leu Arg Lys Gln Phe
                660                 665                 670

Ala Lys Gly Glu Gln Val Ile Arg Tyr Glu Asn Ser Asn Thr Gly Ser
                675                 680                 685

Asn Gly Glu Asp Leu Val Ser Asn Ile Arg Leu Gly Asn Asp Arg Lys
                690                 695                 700

Thr Gly Val Ala Val Val Ala Gly Asn Asn Pro Ala Leu Asp Thr Thr
705                 710                 715                 720
```

```
Ile Thr Val Asp Met Gly Ala Gln His Arg Asn Gln Trp Phe Val Asp
            725                 730                 735

Ala Met Gly Tyr Gln Pro Glu Arg Leu Lys Thr Asp Lys Asp Gly Arg
            740                 745                 750

Leu Thr Val Gln Val Lys Gly Thr Gln Asn Val Asp Val Lys Gly Tyr
        755                 760                 765

Leu Ala Ala Trp Val Pro Asp Leu Gln Ala Gln Glu
    770                 775                 780

<210> SEQ ID NO 2
<211> LENGTH: 34
<212> TYPE: PRT
<213> ORGANISM: Unknown
<220> FEATURE:
<223> OTHER INFORMATION: Primer pair forward

<400> SEQUENCE: 2

Cys Ala Gly Gly Gly Ala Cys Cys Gly Gly Thr Gly Cys Ala Cys
1               5                   10                  15

Cys Gly Gly Cys Cys Cys Cys Ala Cys Gly Gly Cys Cys Thr
            20                  25                  30

Cys Gly

<210> SEQ ID NO 3
<211> LENGTH: 44
<212> TYPE: PRT
<213> ORGANISM: Unknown
<220> FEATURE:
<223> OTHER INFORMATION: Primer pair reverse

<400> SEQUENCE: 3

Cys Gly Ala Gly Gly Ala Gly Ala Ala Gly Cys Cys Cys Gly Gly Thr
1               5                   10                  15

Thr Ala Cys Thr Cys Cys Thr Gly Gly Gly Cys Cys Thr Gly Gly Ala
            20                  25                  30

Gly Gly Thr Cys Cys Gly Gly Ala Ala Cys Cys Cys
        35                  40

<210> SEQ ID NO 4
<211> LENGTH: 7
<212> TYPE: PRT
<213> ORGANISM: Azotobacter chroococcum
<220> FEATURE:
<221> NAME/KEY: misc_feature
<223> OTHER INFORMATION: Motif I

<400> SEQUENCE: 4

Val Asp Val Val Pro Asn Gln
1               5

<210> SEQ ID NO 5
<211> LENGTH: 13
<212> TYPE: PRT
<213> ORGANISM: Azotobacter chroococcum
<220> FEATURE:
<221> NAME/KEY: misc_feature
<223> OTHER INFORMATION: Motif II

<400> SEQUENCE: 5

Phe Asp Gly Phe Arg Ile Asp Ala Ala Ser His Ile Asn
1               5                   10
```

```
<210> SEQ ID NO 6
<211> LENGTH: 11
<212> TYPE: PRT
<213> ORGANISM: Azotobacter chroococcum
<220> FEATURE:
<221> NAME/KEY: misc_feature
<223> OTHER INFORMATION: Motif III

<400> SEQUENCE: 6

His Leu Ser Tyr Ile Glu Ser Tyr Val Thr Gln
1               5                   10

<210> SEQ ID NO 7
<211> LENGTH: 15
<212> TYPE: PRT
<213> ORGANISM: Azotobacter chroococcum
<220> FEATURE:
<221> NAME/KEY: misc_feature
<223> OTHER INFORMATION: Motif IV

<400> SEQUENCE: 7

Phe Val Asn Asn His Asp Gln Glu His Asn Ile Leu Val Thr Val
1               5                   10                  15

<210> SEQ ID NO 8
<211> LENGTH: 7
<212> TYPE: PRT
<213> ORGANISM: Exiguobacterium sibiricum 255-15
<220> FEATURE:
<221> NAME/KEY: misc_feature
<223> OTHER INFORMATION: Motif I

<400> SEQUENCE: 8

Met Asp Leu Val Pro Asn Gln
1               5

<210> SEQ ID NO 9
<211> LENGTH: 13
<212> TYPE: PRT
<213> ORGANISM: Exiguobacterium sibiricum 255-15
<220> FEATURE:
<221> NAME/KEY: misc_feature
<223> OTHER INFORMATION: Motif II

<400> SEQUENCE: 9

Phe Asp Gly Phe Arg Ile Asp Ala Ala Ser His Tyr Asp
1               5                   10

<210> SEQ ID NO 10
<211> LENGTH: 11
<212> TYPE: PRT
<213> ORGANISM: Exiguobacterium sibiricum 255-15
<220> FEATURE:
<221> NAME/KEY: misc_feature
<223> OTHER INFORMATION: Motif III

<400> SEQUENCE: 10

His Leu Ser Tyr Ile Glu Ser Tyr Lys Ser Glu
1               5                   10

<210> SEQ ID NO 11
<211> LENGTH: 15
<212> TYPE: PRT
<213> ORGANISM: Exiguobacterium sibiricum 255-15
<220> FEATURE:
<221> NAME/KEY: misc_feature
<223> OTHER INFORMATION: Motif IV

<400> SEQUENCE: 11
```

```
Phe Val Asn Asn His Asp Gln Glu Lys Asn Arg Val Asn Gln Ile
1               5                   10                  15

<210> SEQ ID NO 12
<211> LENGTH: 7
<212> TYPE: PRT
<213> ORGANISM: Exiguobacterium undae
<220> FEATURE:
<221> NAME/KEY: misc_feature
<223> OTHER INFORMATION: Motif I

<400> SEQUENCE: 12

Met Asp Leu Val Pro Asn Gln
1               5

<210> SEQ ID NO 13
<211> LENGTH: 13
<212> TYPE: PRT
<213> ORGANISM: Exiguobacterium undae
<220> FEATURE:
<221> NAME/KEY: misc_feature
<223> OTHER INFORMATION: Motif II

<400> SEQUENCE: 13

Phe Asp Gly Phe Arg Ile Asp Ala Ala Ser His Tyr Asp
1               5                   10

<210> SEQ ID NO 14
<211> LENGTH: 11
<212> TYPE: PRT
<213> ORGANISM: Exiguobacterium undae
<220> FEATURE:
<221> NAME/KEY: misc_feature
<223> OTHER INFORMATION: Motif III

<400> SEQUENCE: 14

His Leu Ser Tyr Ile Glu Ser Tyr Lys Ser Glu
1               5                   10

<210> SEQ ID NO 15
<211> LENGTH: 15
<212> TYPE: PRT
<213> ORGANISM: Exiguobacterium undae
<220> FEATURE:
<221> NAME/KEY: misc_feature
<223> OTHER INFORMATION: Motif IV

<400> SEQUENCE: 15

Phe Val Asn Asn His Asp Gln Glu Lys Asn Arg Val Asn Gln Ile
1               5                   10                  15

<210> SEQ ID NO 16
<211> LENGTH: 7
<212> TYPE: PRT
<213> ORGANISM: Exiguobacterium antarcticum
<220> FEATURE:
<221> NAME/KEY: misc_feature
<223> OTHER INFORMATION: Motif I

<400> SEQUENCE: 16

Met Asp Leu Val Pro Asn Gln
1               5

<210> SEQ ID NO 17
<211> LENGTH: 13
<212> TYPE: PRT
<213> ORGANISM: Exiguobacterium antarcticum
```

```
<220> FEATURE:
<221> NAME/KEY: misc_feature
<223> OTHER INFORMATION: Motif II

<400> SEQUENCE: 17

Phe Asp Gly Phe Arg Ile Asp Ala Ala Ser His Tyr Asp
1               5                   10

<210> SEQ ID NO 18
<211> LENGTH: 11
<212> TYPE: PRT
<213> ORGANISM: Exiguobacterium antarcticum
<220> FEATURE:
<221> NAME/KEY: misc_feature
<223> OTHER INFORMATION: Motif III

<400> SEQUENCE: 18

His Leu Ser Tyr Ile Glu Ser Tyr Lys Ser Glu
1               5                   10

<210> SEQ ID NO 19
<211> LENGTH: 15
<212> TYPE: PRT
<213> ORGANISM: Exiguobacterium antarcticum
<220> FEATURE:
<221> NAME/KEY: misc_feature
<223> OTHER INFORMATION: Motif IV

<400> SEQUENCE: 19

Phe Val Asn Asn His Asp Gln Glu Lys Asn Arg Val Asn Gln Ile
1               5                   10                  15

<210> SEQ ID NO 20
<211> LENGTH: 7
<212> TYPE: PRT
<213> ORGANISM: Exiguobacterium acetylicum
<220> FEATURE:
<221> NAME/KEY: misc_feature
<223> OTHER INFORMATION: Motif I

<400> SEQUENCE: 20

Met Asp Leu Val Pro Asn Gln
1               5

<210> SEQ ID NO 21
<211> LENGTH: 13
<212> TYPE: PRT
<213> ORGANISM: Exiguobacterium acetylicum
<220> FEATURE:
<221> NAME/KEY: misc_feature
<223> OTHER INFORMATION: Motif II

<400> SEQUENCE: 21

Phe Asp Gly Phe Arg Ile Asp Ala Ala Ser His Tyr Asp
1               5                   10

<210> SEQ ID NO 22
<211> LENGTH: 11
<212> TYPE: PRT
<213> ORGANISM: Exiguobacterium acetylicum
<220> FEATURE:
<221> NAME/KEY: misc_feature
<223> OTHER INFORMATION: Motif III

<400> SEQUENCE: 22

Tyr Leu Ser Tyr Ile Glu Ser Tyr Lys Thr Glu
1               5                   10
```

```
<210> SEQ ID NO 23
<211> LENGTH: 15
<212> TYPE: PRT
<213> ORGANISM: Exiguobacterium acetylicum
<220> FEATURE:
<221> NAME/KEY: misc_feature
<223> OTHER INFORMATION: Motif IV

<400> SEQUENCE: 23

Phe Val Asn Asn His Asp Gln Glu Lys Asn Arg Val Asn Gln Ile
1               5                   10                  15

<210> SEQ ID NO 24
<211> LENGTH: 7
<212> TYPE: PRT
<213> ORGANISM: Bacillus kribbensis
<220> FEATURE:
<221> NAME/KEY: misc_feature
<223> OTHER INFORMATION: Motif I

<400> SEQUENCE: 24

Glu Asp Leu Val Pro Asn Gln
1               5

<210> SEQ ID NO 25
<211> LENGTH: 13
<212> TYPE: PRT
<213> ORGANISM: Bacillus kribbensis
<220> FEATURE:
<221> NAME/KEY: misc_feature
<223> OTHER INFORMATION: Motif II

<400> SEQUENCE: 25

Phe Asp Gly Phe Arg Ile Asp Ala Ala Ser His Tyr Asp
1               5                   10

<210> SEQ ID NO 26
<211> LENGTH: 11
<212> TYPE: PRT
<213> ORGANISM: Bacillus kribbensis
<220> FEATURE:
<221> NAME/KEY: misc_feature
<223> OTHER INFORMATION: Motif III

<400> SEQUENCE: 26

His Leu Ser Tyr Ile Glu Ser Tyr Ser Asn Val
1               5                   10

<210> SEQ ID NO 27
<211> LENGTH: 15
<212> TYPE: PRT
<213> ORGANISM: Bacillus kribbensis
<220> FEATURE:
<221> NAME/KEY: misc_feature
<223> OTHER INFORMATION: Motif IV

<400> SEQUENCE: 27

Phe Val Asn Asn His Asp Gln Glu Lys Asn Arg Val Asn Asn Ile
1               5                   10                  15

<210> SEQ ID NO 28
<211> LENGTH: 7
<212> TYPE: PRT
<213> ORGANISM: Bacillus coagulans DSM 1 = ATCC 7050
<220> FEATURE:
<221> NAME/KEY: misc_feature
<223> OTHER INFORMATION: Motif I
```

```
<400> SEQUENCE: 28

Glu Asp Leu Val Pro Asn Gln
1               5

<210> SEQ ID NO 29
<211> LENGTH: 13
<212> TYPE: PRT
<213> ORGANISM: Bacillus coagulans DSM 1 = ATCC 7050
<220> FEATURE:
<221> NAME/KEY: misc_feature
<223> OTHER INFORMATION: Motif II

<400> SEQUENCE: 29

Phe Asp Gly Phe Arg Ile Asp Ala Ala Gly His Tyr Asp
1               5                   10

<210> SEQ ID NO 30
<211> LENGTH: 11
<212> TYPE: PRT
<213> ORGANISM: Bacillus coagulans DSM 1 = ATCC 7050
<220> FEATURE:
<221> NAME/KEY: misc_feature
<223> OTHER INFORMATION: Motif III

<400> SEQUENCE: 30

His Leu Ser Tyr Ile Glu Ser Tyr Gln Ser Ala
1               5                   10

<210> SEQ ID NO 31
<211> LENGTH: 15
<212> TYPE: PRT
<213> ORGANISM: Bacillus coagulans DSM 1 = ATCC 7050
<220> FEATURE:
<221> NAME/KEY: misc_feature
<223> OTHER INFORMATION: Motif IV

<400> SEQUENCE: 31

Phe Val Asn Asn His Asp Gln Glu Lys Asn Arg Val Asn Lys Ile
1               5                   10                  15

<210> SEQ ID NO 32
<211> LENGTH: 7
<212> TYPE: PRT
<213> ORGANISM: Lactobacillus reuteri 121 (GtfB)
<220> FEATURE:
<221> NAME/KEY: misc_feature
<223> OTHER INFORMATION: Motif I

<400> SEQUENCE: 32

Glu Asp Ile Val Met Asn Gln
1               5

<210> SEQ ID NO 33
<211> LENGTH: 13
<212> TYPE: PRT
<213> ORGANISM: Lactobacillus reuteri 121 (GtfB)
<220> FEATURE:
<221> NAME/KEY: misc_feature
<223> OTHER INFORMATION: Motif II

<400> SEQUENCE: 33

Phe Asp Gly Phe Arg Val Asp Ala Ala Asp Asn Ile Asp
1               5                   10

<210> SEQ ID NO 34
<211> LENGTH: 11
<212> TYPE: PRT
```

```
<213> ORGANISM: Lactobacillus reuteri 121 (GtfB)
<220> FEATURE:
<221> NAME/KEY: misc_feature
<223> OTHER INFORMATION: Motif III

<400> SEQUENCE: 34

His Leu Ser Tyr Asn Glu Gly Tyr His Ser Gly
1               5                   10

<210> SEQ ID NO 35
<211> LENGTH: 15
<212> TYPE: PRT
<213> ORGANISM: Lactobacillus reuteri 121 (GtfB)
<220> FEATURE:
<221> NAME/KEY: misc_feature
<223> OTHER INFORMATION: Motif IV

<400> SEQUENCE: 35

Phe Val Thr Asn His Asp Gln Arg Lys Asn Leu Ile Asn Arg Leu
1               5                   10                  15

<210> SEQ ID NO 36
<211> LENGTH: 7
<212> TYPE: PRT
<213> ORGANISM: Lactobacillus reuteri ML1 (ML4)
<220> FEATURE:
<221> NAME/KEY: misc_feature
<223> OTHER INFORMATION: Motif I

<400> SEQUENCE: 36

Glu Asp Ile Val Met Asn Gln
1               5

<210> SEQ ID NO 37
<211> LENGTH: 13
<212> TYPE: PRT
<213> ORGANISM: Lactobacillus reuteri ML1 (ML4)
<220> FEATURE:
<221> NAME/KEY: misc_feature
<223> OTHER INFORMATION: Motif II

<400> SEQUENCE: 37

Phe Asp Gly Phe Arg Val Asp Ala Ala Asp Asn Ile Asp
1               5                   10

<210> SEQ ID NO 38
<211> LENGTH: 11
<212> TYPE: PRT
<213> ORGANISM: Lactobacillus reuteri ML1 (ML4)
<220> FEATURE:
<221> NAME/KEY: misc_feature
<223> OTHER INFORMATION: Motif III

<400> SEQUENCE: 38

His Leu Ser Tyr Asn Glu Gly Tyr His Ser Gly
1               5                   10

<210> SEQ ID NO 39
<211> LENGTH: 15
<212> TYPE: PRT
<213> ORGANISM: Lactobacillus reuteri ML1 (ML4)
<220> FEATURE:
<221> NAME/KEY: misc_feature
<223> OTHER INFORMATION: Motif IV

<400> SEQUENCE: 39

Phe Val Thr Asn His Asp Gln Arg Lys Asn Leu Ile Asn Arg Leu
1               5                   10                  15
```

```
<210> SEQ ID NO 40
<211> LENGTH: 7
<212> TYPE: PRT
<213> ORGANISM: Lactobacillus salivarius GJ-24
<220> FEATURE:
<221> NAME/KEY: misc_feature
<223> OTHER INFORMATION: Motif I

<400> SEQUENCE: 40

Val Asp Ile Val Met Asn Gln
1               5

<210> SEQ ID NO 41
<211> LENGTH: 13
<212> TYPE: PRT
<213> ORGANISM: Lactobacillus salivarius GJ-24
<220> FEATURE:
<221> NAME/KEY: misc_feature
<223> OTHER INFORMATION: Motif II

<400> SEQUENCE: 41

Phe Asp Gly Phe Arg Ile Asp Ala Ala Asp His Ile Asp
1               5                   10

<210> SEQ ID NO 42
<211> LENGTH: 11
<212> TYPE: PRT
<213> ORGANISM: Lactobacillus salivarius GJ-24
<220> FEATURE:
<221> NAME/KEY: misc_feature
<223> OTHER INFORMATION: Motif III

<400> SEQUENCE: 42

His Leu Ser Tyr Asn Glu Gly Tyr Arg Ser Gly
1               5                   10

<210> SEQ ID NO 43
<211> LENGTH: 15
<212> TYPE: PRT
<213> ORGANISM: Lactobacillus salivarius GJ-24
<220> FEATURE:
<221> NAME/KEY: misc_feature
<223> OTHER INFORMATION: Motif IV

<400> SEQUENCE: 43

Tyr Val Thr Asn His Asp Gln Arg Ala Asn Leu Ile Asn Gly Leu
1               5                   10                  15

<210> SEQ ID NO 44
<211> LENGTH: 7
<212> TYPE: PRT
<213> ORGANISM: Pediococcus pentosaceus
<220> FEATURE:
<221> NAME/KEY: misc_feature
<223> OTHER INFORMATION: Motif I

<400> SEQUENCE: 44

Glu Asp Ile Val Met Asn Gln
1               5

<210> SEQ ID NO 45
<211> LENGTH: 13
<212> TYPE: PRT
<213> ORGANISM: Pediococcus pentosaceus
<220> FEATURE:
<221> NAME/KEY: misc_feature
<223> OTHER INFORMATION: Motif II
```

```
<400> SEQUENCE: 45

Phe Asp Gly Phe Arg Ile Asp Ala Ala Asp Asn Ile Asp
1               5                   10

<210> SEQ ID NO 46
<211> LENGTH: 11
<212> TYPE: PRT
<213> ORGANISM: Pediococcus pentosaceus
<220> FEATURE:
<221> NAME/KEY: misc_feature
<223> OTHER INFORMATION: Motif III

<400> SEQUENCE: 46

His Leu Ser Tyr Asn Glu Gly Tyr His Ser Gly
1               5                   10

<210> SEQ ID NO 47
<211> LENGTH: 15
<212> TYPE: PRT
<213> ORGANISM: Pediococcus pentosaceus
<220> FEATURE:
<221> NAME/KEY: misc_feature
<223> OTHER INFORMATION: Motif IV

<400> SEQUENCE: 47

Phe Val Thr Asn His Asp Gln Arg Lys Asn Leu Ile Asn Ser Leu
1               5                   10                  15

<210> SEQ ID NO 48
<211> LENGTH: 7
<212> TYPE: PRT
<213> ORGANISM: Lactobacillus plantarum
<220> FEATURE:
<221> NAME/KEY: misc_feature
<223> OTHER INFORMATION: Motif I

<400> SEQUENCE: 48

Glu Asp Leu Val Met Asn Gln
1               5

<210> SEQ ID NO 49
<211> LENGTH: 13
<212> TYPE: PRT
<213> ORGANISM: Lactobacillus plantarum
<220> FEATURE:
<221> NAME/KEY: misc_feature
<223> OTHER INFORMATION: Motif II

<400> SEQUENCE: 49

Phe Asp Gly Phe Arg Val Asp Ala Ala Asp His Ile Asp
1               5                   10

<210> SEQ ID NO 50
<211> LENGTH: 11
<212> TYPE: PRT
<213> ORGANISM: Lactobacillus plantarum
<220> FEATURE:
<221> NAME/KEY: misc_feature
<223> OTHER INFORMATION: Motif III

<400> SEQUENCE: 50

His Leu Val Tyr Asn Glu Gly Tyr Asn Tyr Gly
1               5                   10

<210> SEQ ID NO 51
<211> LENGTH: 15
```

```
<212> TYPE: PRT
<213> ORGANISM: Lactobacillus plantarum
<220> FEATURE:
<221> NAME/KEY: misc_feature
<223> OTHER INFORMATION: Motif IV

<400> SEQUENCE: 51

Phe Val Thr Asn His Asp Gln Arg Asn Asn Leu Val Asn Arg Ile
1               5                   10                  15

<210> SEQ ID NO 52
<211> LENGTH: 7
<212> TYPE: PRT
<213> ORGANISM: Lactobacillus reuteri DSM 20016
<220> FEATURE:
<221> NAME/KEY: misc_feature
<223> OTHER INFORMATION: Motif I

<400> SEQUENCE: 52

Glu Asp Leu Val Met Asn Gln
1               5

<210> SEQ ID NO 53
<211> LENGTH: 13
<212> TYPE: PRT
<213> ORGANISM: Lactobacillus reuteri DSM 20016
<220> FEATURE:
<221> NAME/KEY: misc_feature
<223> OTHER INFORMATION: Motif II

<400> SEQUENCE: 53

Phe Asp Gly Phe Arg Val Asp Ala Ala Asp Asn Ile Asp
1               5                   10

<210> SEQ ID NO 54
<211> LENGTH: 11
<212> TYPE: PRT
<213> ORGANISM: Lactobacillus reuteri DSM 20016
<220> FEATURE:
<221> NAME/KEY: misc_feature
<223> OTHER INFORMATION: Motif III

<400> SEQUENCE: 54

His Leu Val Tyr Asn Glu Gly Tyr His Ser Gly
1               5                   10

<210> SEQ ID NO 55
<211> LENGTH: 15
<212> TYPE: PRT
<213> ORGANISM: Lactobacillus reuteri DSM 20016
<220> FEATURE:
<221> NAME/KEY: misc_feature
<223> OTHER INFORMATION: Motif IV

<400> SEQUENCE: 55

Phe Val Thr Asn His Asp Gln Arg Lys Asn Val Ile Asn Gln Ile
1               5                   10                  15

<210> SEQ ID NO 56
<211> LENGTH: 7
<212> TYPE: PRT
<213> ORGANISM: Lactobacillus acidipiscis KCTC 13900
<220> FEATURE:
<221> NAME/KEY: misc_feature
<223> OTHER INFORMATION: Motif I

<400> SEQUENCE: 56

Val Asp Met Val Met Asn Gln
```

-continued

```
<210> SEQ ID NO 57
<211> LENGTH: 13
<212> TYPE: PRT
<213> ORGANISM: Lactobacillus acidipiscis KCTC 13900
<220> FEATURE:
<221> NAME/KEY: misc_feature
<223> OTHER INFORMATION: Motif II

<400> SEQUENCE: 57

Phe Asp Gly Phe Arg Asn Asp Ala Ala Asp Asn Ile Asp
1               5                   10

<210> SEQ ID NO 58
<211> LENGTH: 11
<212> TYPE: PRT
<213> ORGANISM: Lactobacillus acidipiscis KCTC 13900
<220> FEATURE:
<221> NAME/KEY: misc_feature
<223> OTHER INFORMATION: Motif III

<400> SEQUENCE: 58

His Leu Val Tyr Asn Glu Gly Tyr His Ser Gly
1               5                   10

<210> SEQ ID NO 59
<211> LENGTH: 15
<212> TYPE: PRT
<213> ORGANISM: Lactobacillus acidipiscis KCTC 13900
<220> FEATURE:
<221> NAME/KEY: misc_feature
<223> OTHER INFORMATION: Motif IV

<400> SEQUENCE: 59

Phe Val Thr Asn His Asp Gln Arg Lys Asn Val Ile Asn Gln Ile
1               5                   10                  15

<210> SEQ ID NO 60
<211> LENGTH: 7
<212> TYPE: PRT
<213> ORGANISM: Lactobacillus reuteri 180 (Gtf180)
<220> FEATURE:
<221> NAME/KEY: misc_feature
<223> OTHER INFORMATION: Motif I

<400> SEQUENCE: 60

Ala Asp Trp Val Pro Asp Gln
1               5

<210> SEQ ID NO 61
<211> LENGTH: 13
<212> TYPE: PRT
<213> ORGANISM: Lactobacillus reuteri 180 (Gtf180)
<220> FEATURE:
<221> NAME/KEY: misc_feature
<223> OTHER INFORMATION: Motif II

<400> SEQUENCE: 61

Phe Asp Gly Ile Arg Val Asp Ala Val Asp Asn Val Asp
1               5                   10

<210> SEQ ID NO 62
<211> LENGTH: 11
<212> TYPE: PRT
<213> ORGANISM: Lactobacillus reuteri 180 (Gtf180)
<220> FEATURE:
<221> NAME/KEY: misc_feature
```

<223> OTHER INFORMATION: Motif III

<400> SEQUENCE: 62

His Ile Asn Ile Leu Glu Asp Trp Gly Trp Asp
1               5                   10

<210> SEQ ID NO 63
<211> LENGTH: 16
<212> TYPE: PRT
<213> ORGANISM: Lactobacillus reuteri 180 (Gtf180)
<220> FEATURE:
<221> NAME/KEY: misc_feature
<223> OTHER INFORMATION: Motif IV

<400> SEQUENCE: 63

Phe Val Arg Ala His Asp Ser Asn Ala Gln Asp Gln Ile Arg Gln Ala
1               5                   10                  15

<210> SEQ ID NO 64
<211> LENGTH: 7
<212> TYPE: PRT
<213> ORGANISM: Lactobacillus reuteri 121 (GtfA)
<220> FEATURE:
<221> NAME/KEY: misc_feature
<223> OTHER INFORMATION: Motif I

<400> SEQUENCE: 64

Ala Asp Trp Val Pro Asp Gln
1               5

<210> SEQ ID NO 65
<211> LENGTH: 13
<212> TYPE: PRT
<213> ORGANISM: Lactobacillus reuteri 121 (GtfA)
<220> FEATURE:
<221> NAME/KEY: misc_feature
<223> OTHER INFORMATION: Motif II

<400> SEQUENCE: 65

Phe Asp Ser Val Arg Val Asp Ala Pro Asp Asn Ile Asp
1               5                   10

<210> SEQ ID NO 66
<211> LENGTH: 11
<212> TYPE: PRT
<213> ORGANISM: Lactobacillus reuteri 121 (GtfA)
<220> FEATURE:
<221> NAME/KEY: misc_feature
<223> OTHER INFORMATION: Motif III

<400> SEQUENCE: 66

His Ile Asn Ile Leu Glu Asp Trp Asn His Ala
1               5                   10

<210> SEQ ID NO 67
<211> LENGTH: 16
<212> TYPE: PRT
<213> ORGANISM: Lactobacillus reuteri 121 (GtfA)
<220> FEATURE:
<221> NAME/KEY: misc_feature
<223> OTHER INFORMATION: Motif IV

<400> SEQUENCE: 67

Phe Val Arg Ala His Asp Asn Asn Ser Gln Asp Gln Ile Gln Asn Ala
1               5                   10                  15

<210> SEQ ID NO 68

```
<211> LENGTH: 7
<212> TYPE: PRT
<213> ORGANISM: Streptococcus mutants SI (GtfsI)
<220> FEATURE:
<221> NAME/KEY: misc_feature
<223> OTHER INFORMATION: Motif I

<400> SEQUENCE: 68

Ala Asp Trp Val Pro Asp Gln
1               5

<210> SEQ ID NO 69
<211> LENGTH: 13
<212> TYPE: PRT
<213> ORGANISM: Streptococcus mutants SI (GtfsI)
<220> FEATURE:
<221> NAME/KEY: misc_feature
<223> OTHER INFORMATION: Motif II

<400> SEQUENCE: 69

Phe Asp Ser Ile Arg Val Asp Ala Val Asp Asn Val Asp
1               5                   10

<210> SEQ ID NO 70
<211> LENGTH: 11
<212> TYPE: PRT
<213> ORGANISM: Streptococcus mutants SI (GtfsI)
<220> FEATURE:
<221> NAME/KEY: misc_feature
<223> OTHER INFORMATION: Motif III

<400> SEQUENCE: 70

His Leu Ser Ile Leu Glu Ala Trp Ser Tyr Asn
1               5                   10

<210> SEQ ID NO 71
<211> LENGTH: 16
<212> TYPE: PRT
<213> ORGANISM: Streptococcus mutants SI (GtfsI)
<220> FEATURE:
<221> NAME/KEY: misc_feature
<223> OTHER INFORMATION: Motif IV

<400> SEQUENCE: 71

Phe Ile Arg Ala His Asp Ser Glu Val Gln Asp Leu Ile Arg Asp Ile
1               5                   10                  15

<210> SEQ ID NO 72
<211> LENGTH: 7
<212> TYPE: PRT
<213> ORGANISM: Leuconostoc mesenteroides
<220> FEATURE:
<221> NAME/KEY: misc_feature
<223> OTHER INFORMATION: Motif I

<400> SEQUENCE: 72

Ala Asp Val Val Asp Asn Gln
1               5

<210> SEQ ID NO 73
<211> LENGTH: 13
<212> TYPE: PRT
<213> ORGANISM: Leuconostoc mesenteroides
<220> FEATURE:
<221> NAME/KEY: misc_feature
<223> OTHER INFORMATION: Motif II

<400> SEQUENCE: 73
```

Phe Asp Ser Ile Arg Ile Asp Ala Val Asp Phe Ile His
1               5                   10

<210> SEQ ID NO 74
<211> LENGTH: 11
<212> TYPE: PRT
<213> ORGANISM: Leuconostoc mesenteroides
<220> FEATURE:
<221> NAME/KEY: misc_feature
<223> OTHER INFORMATION: Motif III

<400> SEQUENCE: 74

His Ile Ser Leu Val Glu Ala Gly Leu Asp Ala
1               5                   10

<210> SEQ ID NO 75
<211> LENGTH: 16
<212> TYPE: PRT
<213> ORGANISM: Leuconostoc mesenteroides
<220> FEATURE:
<221> NAME/KEY: misc_feature
<223> OTHER INFORMATION: Motif IV

<400> SEQUENCE: 75

Ile Ile His Ala His Asp Lys Gly Val Gln Glu Lys Val Gly Ala Ala
1               5                   10                  15

<210> SEQ ID NO 76
<211> LENGTH: 7
<212> TYPE: PRT
<213> ORGANISM: Bacillus sterothermophilus
<220> FEATURE:
<221> NAME/KEY: misc_feature
<223> OTHER INFORMATION: Motif I

<400> SEQUENCE: 76

Ala Asp Val Val Phe Asp His
1               5

<210> SEQ ID NO 77
<211> LENGTH: 13
<212> TYPE: PRT
<213> ORGANISM: Bacillus sterothermophilus
<220> FEATURE:
<221> NAME/KEY: misc_feature
<223> OTHER INFORMATION: Motif II

<400> SEQUENCE: 77

Ile Asp Gly Phe Arg Leu Asp Ala Val Lys His Ile Lys
1               5                   10

<210> SEQ ID NO 78
<211> LENGTH: 11
<212> TYPE: PRT
<213> ORGANISM: Bacillus sterothermophilus
<220> FEATURE:
<221> NAME/KEY: misc_feature
<223> OTHER INFORMATION: Motif III

<400> SEQUENCE: 78

Leu Phe Thr Val Gly Glu Tyr Trp Ser Tyr Asp
1               5                   10

<210> SEQ ID NO 79
<211> LENGTH: 16
<212> TYPE: PRT
<213> ORGANISM: Bacillus licheniformis
<220> FEATURE:

```
<221> NAME/KEY: misc_feature
<223> OTHER INFORMATION: Motif IV

<400> SEQUENCE: 79

Phe Val Asp Asn His Asp Thr Glu Pro Gly Gln Ala Leu Gln Ser Trp
1               5                   10                  15

<210> SEQ ID NO 80
<211> LENGTH: 7
<212> TYPE: PRT
<213> ORGANISM: Bacillus licheniformis
<220> FEATURE:
<221> NAME/KEY: misc_feature
<223> OTHER INFORMATION: Motif I

<400> SEQUENCE: 80

Gly Asp Val Val Ile Asn His
1               5

<210> SEQ ID NO 81
<211> LENGTH: 13
<212> TYPE: PRT
<213> ORGANISM: Bacillus licheniformis
<220> FEATURE:
<221> NAME/KEY: misc_feature
<223> OTHER INFORMATION: Motif II

<400> SEQUENCE: 81

Leu Asp Gly Phe Arg Leu Asp Ala Val Lys His Ile Lys
1               5                   10

<210> SEQ ID NO 82
<211> LENGTH: 11
<212> TYPE: PRT
<213> ORGANISM: Bacillus licheniformis
<220> FEATURE:
<221> NAME/KEY: misc_feature
<223> OTHER INFORMATION: Motif III

<400> SEQUENCE: 82

Met Phe Thr Val Ala Glu Tyr Trp Gln Asn Asp
1               5                   10

<210> SEQ ID NO 83
<211> LENGTH: 16
<212> TYPE: PRT
<213> ORGANISM: Bacillus licheniformis
<220> FEATURE:
<221> NAME/KEY: misc_feature
<223> OTHER INFORMATION: Motif IV

<400> SEQUENCE: 83

Phe Val Asp Asn His Asp Thr Gln Pro Gly Gln Ser Leu Glu Ser Thr
1               5                   10                  15

<210> SEQ ID NO 84
<211> LENGTH: 7
<212> TYPE: PRT
<213> ORGANISM: Bacillus sp. 707
<220> FEATURE:
<221> NAME/KEY: misc_feature
<223> OTHER INFORMATION: Motif I

<400> SEQUENCE: 84

Gly Asp Val Val Met Asn His
1               5
```

```
<210> SEQ ID NO 85
<211> LENGTH: 13
<212> TYPE: PRT
<213> ORGANISM: Bacillus sp. 707
<220> FEATURE:
<221> NAME/KEY: misc_feature
<223> OTHER INFORMATION: Motif II

<400> SEQUENCE: 85

Leu Asp Gly Phe Arg Ile Asp Ala Val Lys His Ile Lys
1               5                   10

<210> SEQ ID NO 86
<211> LENGTH: 11
<212> TYPE: PRT
<213> ORGANISM: Bacillus sp. 707
<220> FEATURE:
<221> NAME/KEY: misc_feature
<223> OTHER INFORMATION: Motif III

<400> SEQUENCE: 86

Met Phe Ala Val Ala Glu Phe Trp Lys Asn Asp
1               5                   10

<210> SEQ ID NO 87
<211> LENGTH: 16
<212> TYPE: PRT
<213> ORGANISM: Bacillus sp. 707
<220> FEATURE:
<221> NAME/KEY: misc_feature
<223> OTHER INFORMATION: Motif IV

<400> SEQUENCE: 87

Phe Val Asp Asn His Asp Ser Gln Pro Glu Glu Ala Leu Glu Ser Phe
1               5                   10                  15

<210> SEQ ID NO 88
<211> LENGTH: 7
<212> TYPE: PRT
<213> ORGANISM: Halothermothrix orenii
<220> FEATURE:
<221> NAME/KEY: misc_feature
<223> OTHER INFORMATION: Motif I

<400> SEQUENCE: 88

Phe Asp Ala Val Leu Asn His
1               5

<210> SEQ ID NO 89
<211> LENGTH: 13
<212> TYPE: PRT
<213> ORGANISM: Halothermothrix orenii
<220> FEATURE:
<221> NAME/KEY: misc_feature
<223> OTHER INFORMATION: Motif II

<400> SEQUENCE: 89

Phe Asp Gly Phe Arg Leu Asp Ala Val Lys His Ile Asp
1               5                   10

<210> SEQ ID NO 90
<211> LENGTH: 11
<212> TYPE: PRT
<213> ORGANISM: Paenibacillus beijingensis
<220> FEATURE:
<221> NAME/KEY: misc_feature
<223> OTHER INFORMATION: Motif III

<400> SEQUENCE: 90
```

```
Val Phe Phe Val Gly Glu Ala Trp Val Glu Asp
1               5                   10
```

<210> SEQ ID NO 91
<211> LENGTH: 16
<212> TYPE: PRT
<213> ORGANISM: Paenibacillus beijingensis
<220> FEATURE:
<221> NAME/KEY: misc_feature
<223> OTHER INFORMATION: Motif IV

<400> SEQUENCE: 91

```
Phe Val Asp Asn His Asp Thr Asp Arg Asp Glu Gly Ser Tyr Thr Val
1               5                   10                  15
```

<210> SEQ ID NO 92
<211> LENGTH: 776
<212> TYPE: PRT
<213> ORGANISM: Paenibacillus beijingensis

<400> SEQUENCE: 92

```
Met Thr Leu Arg Asn Asn Trp Met Lys Val Ser Leu Ser Leu Ser Leu
1               5                   10                  15

Leu Ala Gly Thr Ala Ile Ala Gly Val Ala Pro Ala Asn Ala Ala Glu
                20                  25                  30

Ser Asn Ala Lys Gly Phe Val Ser Asn Ala Glu Leu Asp Lys His Val
            35                  40                  45

Ile Phe Gln Ser Phe Ser Leu Tyr Gln Pro Tyr Glu Lys Asn Met Tyr
        50                  55                  60

Asn Ile Leu Gly Lys Asn Ser Ala Lys Leu Lys Asp Trp Gly Ile Thr
65                  70                  75                  80

Asp Ile Trp Met Pro Pro Ala Tyr Arg Thr Phe Ser Gly Ser Tyr Tyr
                85                  90                  95

Gly Glu Gly Tyr Ala Ile Ser Asp Arg Tyr Asp Leu Gly Glu Phe Pro
            100                 105                 110

Asn Gly Leu Asn Gly Glu Arg Ala Thr Lys Tyr Gly Thr Ser Asp Glu
        115                 120                 125

Leu Lys Arg Ala Ile Lys Gln Leu His Ser Lys Asp Leu Asn Val Gln
130                 135                 140

Val Asp Leu Val Pro Asn Gln Met Met Gly Phe Pro Lys Gln Glu Ile
145                 150                 155                 160

Val Asn Val Thr Ala Val Asp Ser Tyr Gly Asn Glu Ile Asp Pro Ala
                165                 170                 175

Phe Lys Asp Lys Leu Val Pro Leu Tyr Thr Lys Gly Gly Pro Gly
            180                 185                 190

Gln Ala Lys Tyr Gly Leu Ile Lys Glu Trp Ser Ser Lys Tyr Phe Asn
        195                 200                 205

Gly Gly Gly Pro Met Gln Met Gly Ser Met Arg Ile Met Val Asp Ala
    210                 215                 220

Glu Gly Lys Pro Tyr Arg Tyr Phe Gly Pro Asp His Gln Asp Asn Tyr
225                 230                 235                 240

Leu Pro Glu Trp Leu Ala Ser Ser Glu Ala Gln Lys Tyr Gly Lys Ile
                245                 250                 255

Asn His Ile Asp Asn Tyr Leu Thr Val Asp Ser Tyr Phe Ala Val Lys
            260                 265                 270

Gly Ala Asn Thr Asp Asn Asp Gln Val Trp Arg Ser Leu Leu Leu Tyr
        275                 280                 285
```

-continued

Tyr Val Asp Pro Gln Ala Gly Ser Ala Asn Glu Ser Tyr Leu Asp Phe
290                 295                 300

Met Arg Lys Asn Gly Phe Glu Gly Ala Thr Asp Asp Glu Val Arg Glu
305                 310                 315                 320

Lys Ile Ile Ala Ala Asp Ser Ala Val Thr Lys Leu Thr Asp Ser
            325                 330                 335

Tyr Ile Asn Ala Gln Pro Gly Tyr Ser Ala Thr Asp Pro Lys Gly
            340                 345                 350

Leu His Arg Tyr Asn Asn Gly Val Asn Gly Asn Val Asn Gln Asn Val
            355                 360                 365

Leu Gln Tyr Glu Phe Leu Val Gly Thr Asp Ile Asp Asn Ser Asn Pro
370                 375                 380

Thr Val Gln Ala Glu Gln Leu Asn Trp Val Lys Phe Leu Ile Asp Lys
385                 390                 395                 400

Tyr Gly Phe Asp Gly Phe Arg Ile Asp Ala Ala Ser His Tyr Asn Thr
            405                 410                 415

Lys Ile Leu Thr Asp Met Arg Asp Glu Met Ser Ser Arg Phe Gly Asp
            420                 425                 430

Asp Leu Asn Asn His Leu Ser Tyr Ile Glu Ser Tyr Thr Asp Asn Gln
            435                 440                 445

Leu Gly Phe Glu Asn Ser Thr Gly Asn Gly Gln Leu Val Tyr Asp His
            450                 455                 460

Gly Val Phe Gly Ala Leu Arg Asp Ser Leu Gly Lys Glu His Asn Trp
465                 470                 475                 480

Arg Pro Leu Ser Asp Ile Val Thr Ser Ser Tyr Val Asn Arg Ala Asn
                485                 490                 495

Pro Asp Ala Lys Pro Thr Pro Asn Trp Ser Phe Val Met Asn His Asp
            500                 505                 510

Gln Glu His Asn Gly Ile Lys Gly Ile Pro Leu Thr Glu Glu Glu Ala
            515                 520                 525

Gly Gly Thr Lys Lys Asn Thr Val Asp Tyr Glu Lys Lys Gln Phe Glu
530                 535                 540

Lys Tyr Tyr Ala Asp Met Val Asn Ala Asp Lys Lys Tyr Ala Asn Tyr
545                 550                 555                 560

Asn Val Pro Ser Gln Tyr Ala Tyr Leu Leu Thr Asn Lys Asp Thr Val
                565                 570                 575

Pro Thr Val Tyr Tyr Gly Asp Met Phe Lys Ser Thr Ala Ser Tyr Met
            580                 585                 590

Ser Glu Lys Thr Gln Tyr Phe Glu Pro Ile Val Lys Leu Leu Gln Ala
            595                 600                 605

Arg Gln Lys Tyr Val Ser Gly Asp Gln Lys Ile Thr Tyr Tyr Asn Ser
610                 615                 620

Asn Thr Ser Trp Ser Ala Gly Trp Asp Leu Leu Ala Ser Val Arg Phe
625                 630                 635                 640

Gly Thr Ser Arg Asp Thr Gly Val Ala Thr Val Ile Gly Ser Asn Pro
                645                 650                 655

Asn Thr Gln Glu Leu Ile Ser Val Asp Met Gly Lys Leu His Ala Asn
            660                 665                 670

Gln Thr Phe Glu Asp Val Met Gly Phe Asn Thr Gln Lys Leu Thr Thr
            675                 680                 685

Asp Glu Asn Gly Val Leu Thr Val Pro Val Lys Gly Val Ser Asn Pro
690                 695                 700

```
Leu Val His Gly Tyr Leu Gly Val Trp Val Pro Ser Lys Glu Lys Gly
705                 710                 715                 720

Gly Glu Lys Val Lys Val Lys Gly Lys Ile Gly Val Asp Ala Ser Val
                725                 730                 735

Glu Ser Asn Thr Glu Ser Glu Thr Lys Thr Asp Gly Ile Thr Asn Gly
            740                 745                 750

His Glu Trp Gln Gln Gln Gln Glu Ala Glu Gln Leu Lys Lys Trp Asn
        755                 760                 765

Lys Ala Leu Arg Arg Phe Ser Asn
    770                 775

<210> SEQ ID NO 93
<211> LENGTH: 32
<212> TYPE: PRT
<213> ORGANISM: Unknown
<220> FEATURE:
<223> OTHER INFORMATION: PbF

<400> SEQUENCE: 93

Cys Ala Gly Gly Gly Ala Cys Cys Cys Gly Gly Thr Gly Cys Gly Gly
1               5                   10                  15

Ala Ala Ala Gly Cys Ala Ala Thr Gly Cys Gly Ala Ala Ala Gly Gly
            20                  25                  30

<210> SEQ ID NO 94
<211> LENGTH: 46
<212> TYPE: PRT
<213> ORGANISM: Unknown
<220> FEATURE:
<223> OTHER INFORMATION: PbR

<400> SEQUENCE: 94

Cys Gly Ala Gly Gly Ala Gly Ala Ala Gly Cys Cys Cys Gly Gly Thr
1               5                   10                  15

Thr Ala Ala Thr Thr Gly Cys Thr Ala Ala Ala Cys Cys Gly Thr Cys
            20                  25                  30

Thr Thr Ala Ala Thr Gly Cys Thr Thr Thr Ala Thr Thr Cys
        35                  40                  45

<210> SEQ ID NO 95
<211> LENGTH: 7
<212> TYPE: PRT
<213> ORGANISM: Paenibacillus beijingensis
<220> FEATURE:
<221> NAME/KEY: misc_feature
<223> OTHER INFORMATION: Motif I

<400> SEQUENCE: 95

Val Asp Leu Val Pro Asn Gln
1               5

<210> SEQ ID NO 96
<211> LENGTH: 11
<212> TYPE: PRT
<213> ORGANISM: Paenibacillus beijingensis
<220> FEATURE:
<221> NAME/KEY: misc_feature
<223> OTHER INFORMATION: Motif II

<400> SEQUENCE: 96

Gly Phe Arg Ile Asp Ala Ala Ser His Tyr Asn
1               5                   10
```

```
<210> SEQ ID NO 97
<211> LENGTH: 11
<212> TYPE: PRT
<213> ORGANISM: Paenibacillus beijingensis
<220> FEATURE:
<221> NAME/KEY: misc_feature
<223> OTHER INFORMATION: Motif III

<400> SEQUENCE: 97

His Leu Ser Tyr Ile Glu Ser Tyr Thr Asp Asn
1               5                   10

<210> SEQ ID NO 98
<211> LENGTH: 14
<212> TYPE: PRT
<213> ORGANISM: Paenibacillus beijingensis
<220> FEATURE:
<221> NAME/KEY: misc_feature
<223> OTHER INFORMATION: Motif IV

<400> SEQUENCE: 98

Phe Val Met Asn His Asp Gln Glu His Asn Gly Ile Lys Gly
1               5                   10
```

US 10,626,428 B2

BRANCHED ALPHA GLUCANS

CROSS REFERENCE TO RELATED APPLICATIONS

The present application is a National Stage of International Application No. PCT/EP2016/071474, filed on Sep. 12, 2016, which claims priority to European Patent Application No. 15185336.3, filed on Sep. 15, 2015, the entire contents of which are being incorporated herein by reference.

FIELD OF THE INVENTION

The present invention relates to the field of poly- and oligosaccharides and their dietary effects. In particular it relates to a method of producing a branched α-glucan. Further aspects of the invention are a branched α-glucan comprising alternating α(1→4) and α(1→6) glucosidic linkages and having α(1→4,6) branching points, a food composition, and the use of an α-glucanotransferase enzyme for reducing the digestible carbohydrates of a starch containing food material.

BACKGROUND OF THE INVENTION

The prevalence of obesity and being overweight is rapidly increasing worldwide. The development of foods with high satiating capacities and low energy densities may help to prevent weight gain and to stimulate weight loss. Consumption of food and drinks containing non-digestible carbohydrates instead of sugars induces a lower blood glucose rise after meals compared to sugar-containing food and drinks.

The most common carbohydrate in human diets is starch. This polysaccharide is produced by most green plants as an energy store. It is contained in large amounts in such staple foods as potatoes, wheat, maize, rice, and cassava. Various methods have been proposed for the chemical modification of starch and malto-oligosaccharides into non-digestible carbohydrates.

EP2427565 describes the use of a glucanotransferase enzyme of *Lactobacillus reuteri* 121 GTFB to convert starch into linear gluco-oligosaccharides containing relatively long isomalto-oligosaccharide side chains. Such materials are partially resistant to digestion and hence give less glucose production on consumption, contributing to the prevention of obesity and type II diabetes.

It has been observed that highly branched α-glucans can combine a reduced digestibility with a thickening effect triggered by the low pH conditions of the stomach. This thickening leads to feelings of satiety. The production of highly branched α-glucans from sucrose has been described, for example the synthesis of reuteran by the *Lactobacillus reuteri* 121 GTFA glucansucrase (Kralj et al., 2002).

It would be desirable to provide further means for the enzymatic modification of starch, starch derivatives and malto-oligosaccharides in order to change their functional properties and enhance their nutritional value. In particular it would be beneficial to provide enzymes to perform such modifications which are suitable for use in food manufacture and exhibit good enzyme activity and thermostability.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

An object of the present invention is to improve the state of the art and to provide an improved solution for the enzymatic modification of starch and other polysaccharide or oligosaccharide into materials having reduced digestibility, or at least to provide a useful alternative. The object of the present invention is achieved by the subject matter of the independent claims. The dependent claims further develop the idea of the present invention.

Accordingly, the present invention provides in a first aspect a method of producing an α-glucan with a ratio of branching of at least 8% comprising contacting a polysaccharide or oligosaccharide substrate comprising at its non-reducing end at least two α(1→4) linked D-glucose units with an α-glucanotransferase enzyme capable of cleaving α(1→4) glucosidic linkages and making new alternating α(1→4) and α(1→6) glucosidic linkages with α(1→4,6) branching points, wherein said α-glucanotransferase is selected from the group consisting of GTFB, GTFC and GTFD types of enzyme, or a functional homolog thereof having the specified enzymatic activity.

In a second aspect, the invention relates to an α-glucan comprising alternating α(1→4) and α(1→6) glucosidic linkages and having α(1→4,6) branching points wherein the α-glucan has a ratio of branching of at least 15% and an average molecular mass between $1\times10^6$ Da and $40\times10^6$ Da. A third aspect of the invention relates to a food composition comprising an α-glucan comprising alternating α(1→4) and α(1→6) glucosidic linkages and having α(1→4,6) branching points wherein the α-glucan has a ratio of branching of at least 15% and an average molecular mass between $1\times10^6$ Da and $40\times10^6$ Da.

A still further aspect of the invention is the use of an α-glucanotransferase enzyme that comprises an amino acid sequence having at least 80% identity to SEQ ID NO:1, or has an amino acid sequence of SEQ ID NO:1, for reducing the digestible carbohydrates of a starch containing food material.

INCORPORATION BY REFERENCE OF SEQUENCE LISTING ON ASCII TEXT FILE

The content of the following submission on ASCII text file is incorporated herein by reference in its entirety: a computer readable form (CRF) of the Sequence Listing (file name:—PatentIn-Branched Alpha Glucans-3712036.03037_ST25, Size 36,869 bytes, and Date of Creation Jul. 10, 2018).

Recently, the inventors have identified two novel glycoside hydrolase subfamilies of enzymes inactive on sucrose, but displaying 4,6-α-glucanotransferase (4,6-α-GTase) activity on starch/maltodextrin substrates, and represented by the *Lactobacillus reuteri* 121 GTFB (S. Kralj et al., 2011) and the *Exiguobacterium sibiricum* 255-15 GTFC enzymes (Gangoiti et al., 2015). Both GTFB and GTFC enzymes catalyze the cleavage of the α(1→4) and the synthesis of linear α(1→6)-glucan chains. Like glucansucrases, GTFB type of enzymes are exclusively found in lactic acid bacteria and possess a catalytic $(\alpha/\beta)_8$-barrel domain that is circularly permuted with respect to that of the GH13 α-amylase enzymes. In contrast, the GTFC type of enzymes is present in non-lactic acid Gram-positive bacteria, and has a non-permuted domain organization resembling that of GH13 enzymes. GTFC enzymes thus appear to represent further evolutionary intermediates between GH13 α-amylases and GH70 glucansucrases/GTFB-like 4,6-α-glucanotransferases.

The inventors have identified a novel GH70 family protein in the genome of the nitrogen-fixing bacterium *Azotobacter chroococccum* NCIMB 8003. This enzyme is designated GTFD and is most closely related to GTFC type of enzymes, sharing the same domain architecture and displaying hydrolase/transglycosylase activity with starch/maltodextrin substrates. However, the *A. chroococcum* GTFD enzyme is unable to synthesize consecutive α(1→6) glucosidic bonds, and instead it forms a higher molecular mass and relatively highly branched α-glucan with alternating α(1→4) and α(1→6) glucosidic linkages from amylose and starch. Therefore this polymer is similar to reuteran synthesized by the *L. reuteri* 121 GTFA glucansucrase from sucrose, regarded as a health promoting food ingredient. The GTFD enzyme shows its maximum activity at pH 6.5 and 60° C., and exhibits a higher thermostability than the GTFA glucansucrase and the GTFB and GTFC 4,6-α-glucanotransferases. An enzyme that converts starch into a reuteran-like α-glucan polymer has not been described before.

1D $^1$H NMR analysis of the branched α-glucan formed by the *A. chroococcum* GTFD enzyme revealed the formation of α(1→4) and α(1→6) linkages. Methylation analysis of the α-glucan revealed the presence of terminal, 4-substituted, 6-substituted, and 4,6-disubstituted glucopyranose residues. The presence of 6-substituted, and 4,6-disubstituted glucopyranose residues means that the GTFD enzyme forms α(1→6) linkages in linear and branched orientation. No evidence was observed for two consecutive α(1→6)-linked glucopyranose residues by 2D NMR spectroscopy analysis. Thus, all the branched residues are α(1→4,6)-α-D-Glcp-α(1→4)-residues. Also, all 6-substituted glucopyranose residues detected by methylation analysis must be α(1→4)-linked and are connecting α(1→4) glucan chains forming alternating α(1→6)/α(1→4) linkages in the linear part of the α-glucan structure. This is in contrast to the action of branching enzymes with E.C. 2.4.1.18 activity disclosed in EP1943908. Such branching enzymes only create α(1→4, 6) branching points but do not create α(1→6) linkages in the linear part of the α-glucan structure, and so do not form alternating α(1→4) and α(1→6) glucosidic linkages.

The inventors have identified a second example of a GH70 family protein displaying this novel reaction and product specificity in the genome of the bacterium *Paenibacillus beijingensis* DSM 24997. This enzyme is designated GTFD and is closely related to the GTFC subfamily of enzymes present in *Bacillus, Geobacillus* and *Exiguobacterium* strains. It displays 4,6-α-glucanotransferase activity with starch/maltodextrin substrates but, like *A. chroococcum* GTFD, is unable to synthesize consecutive α(1→6) glucosidic bonds. The *P. beijingensis* GTFD activity on amylose results in the synthesis of a high-molecular (HMM) and low-molecular mass (LMM) polysaccharides, highly branched α-glucans with alternating α(1→4) and α(1→6) glucosidic linkages.

1D $^1$H NMR analysis of the branched α-glucan formed by the *P. beijingensis* GTFD enzyme revealed the formation of α(1→4) and α(1→6) linkages. Methylation analysis of the α-glucan revealed the presence of terminal, 4-substituted, 6-substituted, and 4,6-disubstituted glucopyranose residues. The presence of 6-substituted, and 4,6-disubstituted glucopyranose residues means that the GTFD enzyme forms α(1→6) linkages in linear and branched orientation. No evidence was observed for two consecutive α(1→6)-linked glucopyranose residues by 2D NMR spectroscopy analysis. Thus, all the branched residues are α(1→4,6)-α-D-Glcp-α(1→4)-residues. Also, all 6-substituted glucopyranose residues detected by methylation analysis must be α(1→4)-linked and are connecting α(1→4) glucan chains forming alternating α(1→6)/α(1→4) linkages in the linear part of the α-glucan structure. This is in contrast to the action of branching enzymes with E.C. 2.4.1.18 activity disclosed in EP1943908. Such branching enzymes only create α(1→4,6) branching points but do not create α(1→6) linkages in the linear part of the α-glucan structure.

DESCRIPTION OF THE DRAWINGS

FIG. 3 shows the sequence alignment of conserved motifs I-IV in the catalytic domain of *Azotobacter chroococcum* NCIMB 8003 GTFD enzyme (A), (putative) GTFC-like 4,6-α-glucanotransferase enzymes (B), (putative) GTFB-like 4,6-α-glucanotransferase enzymes (C), glucansucrase enzymes (D), and GH13 α-amylase enzymes (E). The seven strictly conserved amino acid residues in GH70 enzymes (indicated by the numbers 1 to 7 above the sequences) are also conserved in the novel *Azotobacter chroococcum*

Figure 1:
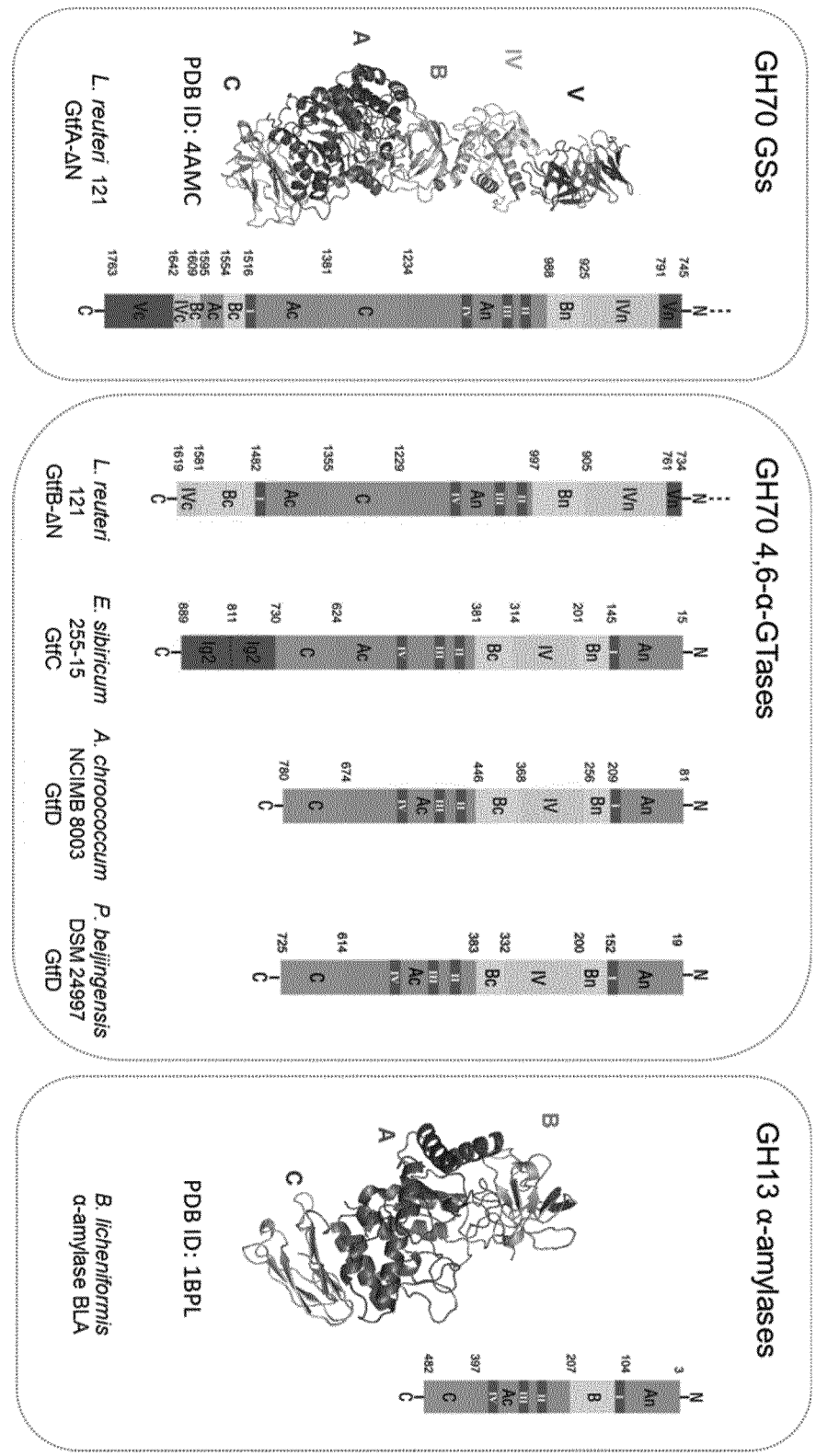
FIG. 1 shows a linear schematic representation of the domain organization of GH70 family proteins. From left to right: *Lactobacillus reuteri* 121 GTFA-ΔN glucansucrase (Pijning et al., 2012), *Lactobacillus reuteri* 121 GTFB-ΔN 4,6-α-glucanotransferase (Bai et al., 2015b), *Exiguobacterium sibiricum* 255-15 GTFC 4,6-α-glucanotransferase (Gangoiti et al., 2015), *Azotobacter chroococcum* NCIMB 8003 GTFD enzyme and *P. beijingensis* DSM 24997 GTFD. The crystal structure of the GTFA-ΔN glucansucrase (Pijning et al., 2012) (left) and the *B. licheniformis* α-amylase (Machius et al., Mol Biol 246:545-559 (1995)) (right) are included showing the unusual "U-fold" domain structure of GH70 glucansucrases, in which 4 of the 5 domains are built up form two discontinuous segments of the polypeptide chain, i.e. are formed from the N- and C-terminal halves. Domains A, B, C and IV were identified in the *A. chroococcum* GTFD primary structure by sequence comparisons with the *L. reuteri* 121 GTFB and *E. sibiricum* GTFC sequences, using Clustal W2. GTFD enzyme lacks the Ig2-like domains identified in *E. sibiricum* GTFC and domain V exclusively found in glucansucrases and GTFB-like 4,6-α-glucanotransferases. Domains A, B, C and IV were assigned in *P. beijingensis* GTFD by sequence comparison with *L. reuteri* 121 GTFB. The order of the conserved regions I-IV in glucansucrases and GTFB-like 4,6-α-glucanotransferases is II-III-IV-I, reflecting their circularly permuted domain organization. The amino acid residue numbers indicate the start of each domain. Conserved regions I-IV are represented by dark grey rectangles.

NCIMB 8003 GTFD protein. Amino acids that constitute the catalytic triad are indicated with triangles. Residues forming acceptor subsites −1, +1 and +2 in GTF180-ΔN (Vujičić-agar et al., 2010) are shown lightly shaded. Symbols: NU=nucleophile, A/B=general acid/base, TS=transition state stabilizer.

The sequence identification numbers for the motifs I-IV of *Azotobacter chroococcum* NCIMB 8003 are SEQ ID NO:4, SEQ ID NO:5, SEQ ID NO:6, and SEQ ID NO:7 respectively. The sequence identification numbers for the motifs I-IV of *Exiguobacterium sibiricum* 255-15 are SEQ ID NO:8, SEQ ID NO:9, SEQ ID NO:10, and SEQ ID NO:11 respectively. The sequence identification numbers for the motifs I-IV of *Exiguobacterium undae* are SEQ ID NO:12, SEQ ID NO:13, SEQ ID NO:14, and SEQ ID NO:15 respectively. The sequence identification numbers for the motifs I-IV of *Exiguobacterium antarcticum* are SEQ ID NO:16, SEQ ID NO:17, SEQ ID NO:18, and SEQ ID NO:19 respectively. The sequence identification numbers for the motifs I-IV of *Exiguobacterium acetylicum* are SEQ ID NO:20, SEQ ID NO:21, SEQ ID NO:22, and SEQ ID NO:23 respectively. The sequence identification numbers for the motifs I-IV of *Bacillus kribbensis* are SEQ ID NO:24, SEQ ID NO:25, SEQ ID NO:26, and SEQ ID NO:27 respectively. The sequence identification numbers for the motifs I-IV of *Bacillus coagulans* DSM 1 are SEQ ID NO:28, SEQ ID NO:29, SEQ ID NO:30, and SEQ ID NO:31 respectively. The sequence identification numbers for the motifs I-IV of *Lactobacillus reuteri* 121 (GtfB) are SEQ ID NO:32, SEQ ID NO:33, SEQ ID NO:34, and SEQ ID NO:35 respectively. The sequence identification numbers for the motifs I-IV of *Lactobacillus reuteri* ML1 (ML4) are SEQ ID NO:36, SEQ ID NO:37, SEQ ID NO:38, and SEQ ID NO:39 respectively. The sequence identification numbers for the motifs I-IV of *Lactobacillus salivarius* GJ-24 are SEQ ID NO:40, SEQ ID NO:41, SEQ ID NO:42, and SEQ ID NO:43 respectively. The sequence identification numbers for the motifs I-IV of *Pediococcus pentosaceus* are SEQ ID NO:44, SEQ ID NO:45, SEQ ID NO:46, and SEQ ID NO:47 respectively. The sequence identification numbers for the motifs I-IV of *Lactobacillus plantarum* are SEQ ID NO:48, SEQ ID NO:49, SEQ ID NO:50, and SEQ ID NO:51 respectively. The sequence identification numbers for the motifs I-IV of *Lactobacillus reuteri* DSM 20016 are SEQ ID NO:52, SEQ ID NO:53, SEQ ID NO:54, and SEQ ID NO:55 respectively. The sequence identification numbers for the motifs I-IV of *Lactobacillus acidipiscis* KCTC 13900 are SEQ ID NO:56, SEQ ID NO:57, SEQ ID NO:58, and SEQ ID NO:59 respectively. The sequence identification numbers for the motifs I-IV of *Lactobacillus reuteri* 180 are SEQ ID NO:60, SEQ ID NO:61, SEQ ID NO:62, and SEQ ID NO:63 respectively. The sequence identification numbers for the motifs I-IV of *Lactobacillus reuteri* 121 (GtfA) are SEQ ID NO:64, SEQ ID NO:65, SEQ ID NO:66, and SEQ ID NO:67 respectively. The sequence identification numbers for the motifs I-IV of *Streptococcus mutants* SI (GtfsI) are SEQ ID NO:68, SEQ ID NO:69, SEQ ID NO:70, and SEQ ID NO:71 respectively. The sequence identification numbers for the motifs I-IV of *Leuconostoc mesenteroides* are SEQ ID NO:72, SEQ ID NO:73, SEQ ID NO:74, and SEQ ID NO:75 respectively. The sequence identification numbers for the motifs I-IV of *Bacillus sterothermophilus* are SEQ ID NO:76, SEQ ID NO:77, SEQ ID NO:78, and SEQ ID NO:79 respectively. The sequence identification numbers for the motifs I-IV of *Bacillus licheniformis* are SEQ ID NO:80, SEQ ID NO:81, SEQ ID NO:82, and SEQ ID NO:83 respectively. The sequence identification numbers for the motifs I-IV of *Bacillus* sp. 707 are SEQ ID NO:84, SEQ ID NO:85, SEQ ID NO:86, and SEQ ID NO:87 respectively. The sequence identification numbers for the motifs I-IV of *Halothermothrix orenii* are SEQ ID NO:88, SEQ ID NO:89, SEQ ID NO:90, and SEQ ID NO:91 respectively.

FIG. 4 shows an SDS-PAGE analysis of the *Azotobacter chroococcum* NCIMB 8003 GTFD protein purified from *E. coli* BL21 Star (DE3). Lane M, molecular mass standards; lane 1, sample of cell free extract; lane 2, sample of the insoluble fraction after centrifugation of lysed cells; lane 3, pooled fractions after Ni-NTA agarose column chromatography. Bands corresponding to the GTFD protein are marked with an arrow.

Figure 5:
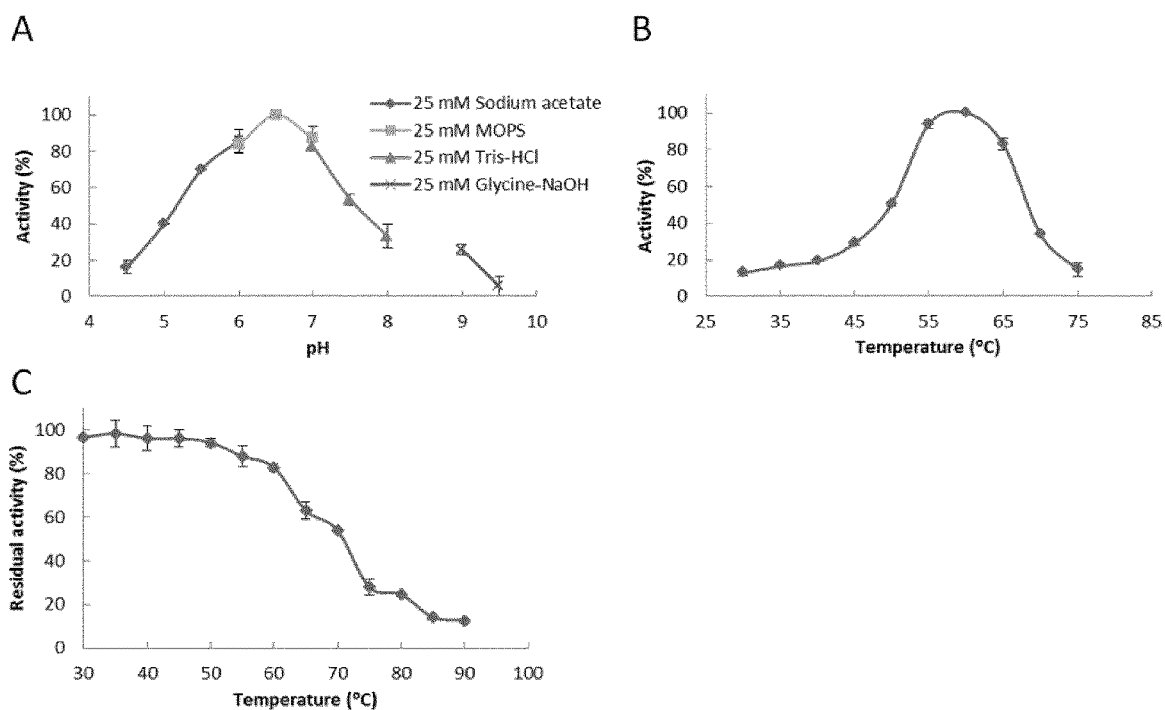

FIG. 5 shows biochemical properties of the purified *Azotobacter chroococcum* NCIMB 8003 GTFD enzyme. (A) Effect of pH on GTFD activity. The assays were carried out at 37° C. and relative enzyme activity was compared with enzyme activity at pH 6.5 (100% value). (B) Effect of temperature on GTFD activity. Experiments were performed at pH 6.5 and relative activity was compared with the enzyme activity at 60° C. (100% value). (C) Effect of temperature on GTFD stability. GTFD enzyme (0.5 mg ml$^{-1}$) was incubated for 10 min at the indicated temperature in 20 mM Tris-HCl pH 8.0 buffer containing 1 mM CaCl$_2$. Residual activity was assayed at 50° C. in the standard conditions described in experimental section.

Figure 6:
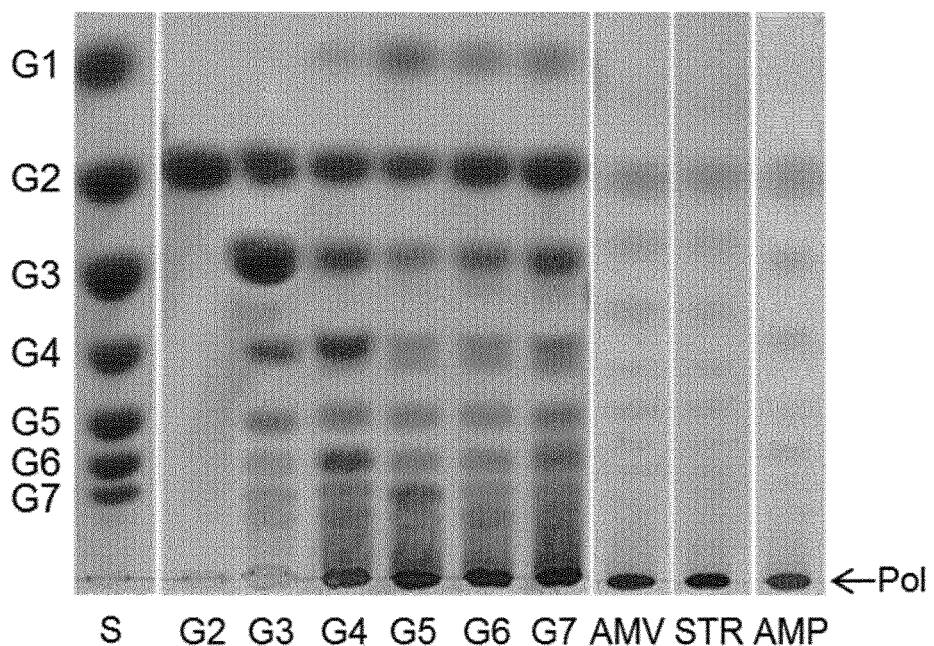

FIG. 6 shows a TLC analysis of the product mixtures synthesized by 40 μg ml$^{-1}$ of the *Azotobacter chroococcum* NCIMB 8003 GTFD enzyme from incubations with 25 mM malto-oligosaccharides (DP2-DP7), 0.6% (w/v) amylose V, 0.6% potato soluble starch, and 0.6% amylopectin. The reaction mixtures were incubated at 37° C. and pH 6.5 during 24 h. S, standard; G1, glucose; G2-G7, maltose to maltoheptaose; AMV, amylose V; STR, starch; AMP, amylopectin; Pol, polymer.

Figure 7:
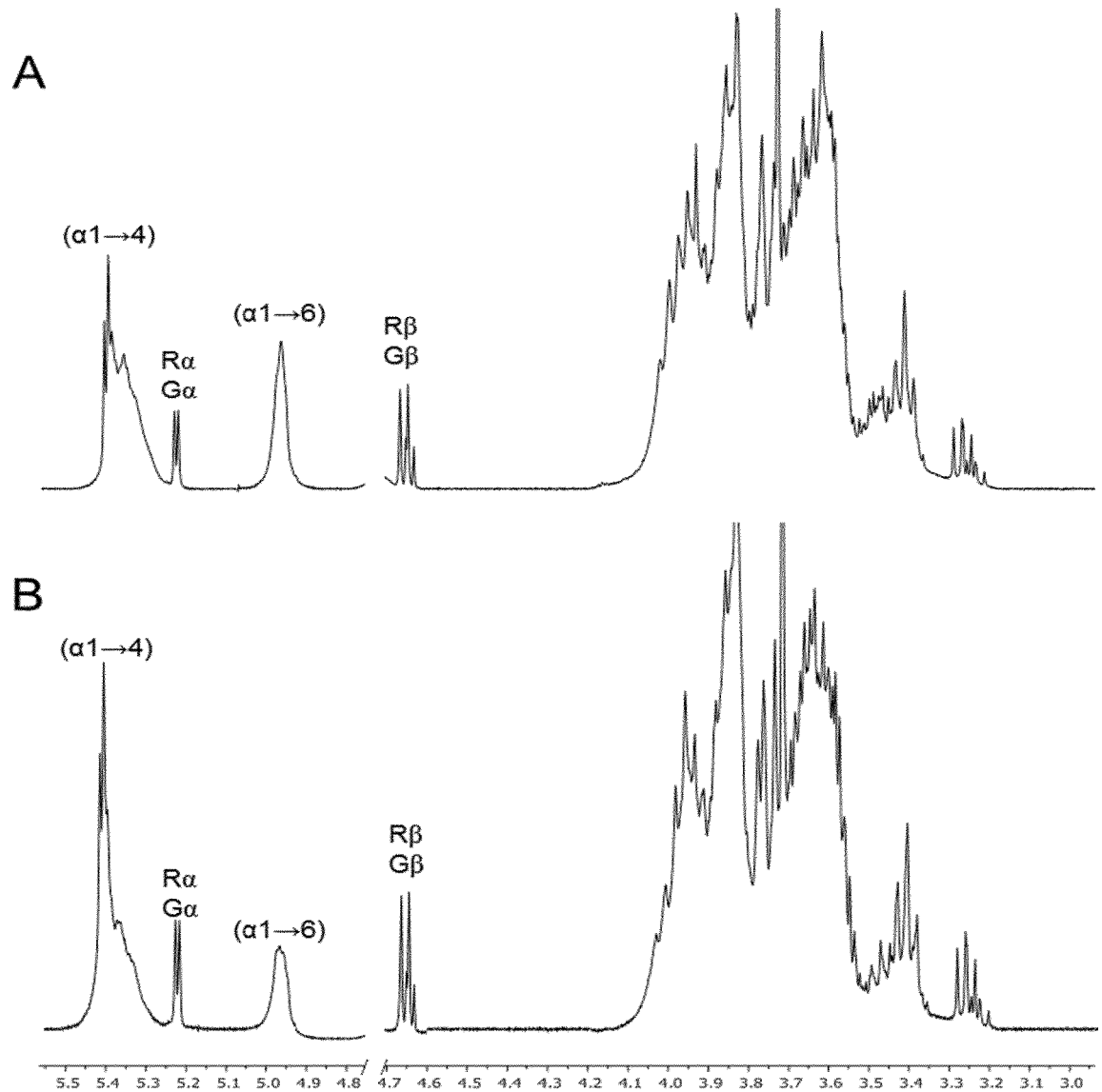

FIG. 7 shows a 500-MHz 1-dimensional $^1$H NMR analysis of reaction mixtures obtained by the incubation of 0.6% (w/v) amylose V (A) and potato starch (B) with 40 μg ml$^{-1}$ of *Azotobacter chroococcum* NCIMB 8003 GTFD enzyme (pH 6.5, 24 h), recorded in D$_2$O. Chemical shifts are given in parts per million relative to the signal of internal acetone (δ 2.225).

Figure 8:
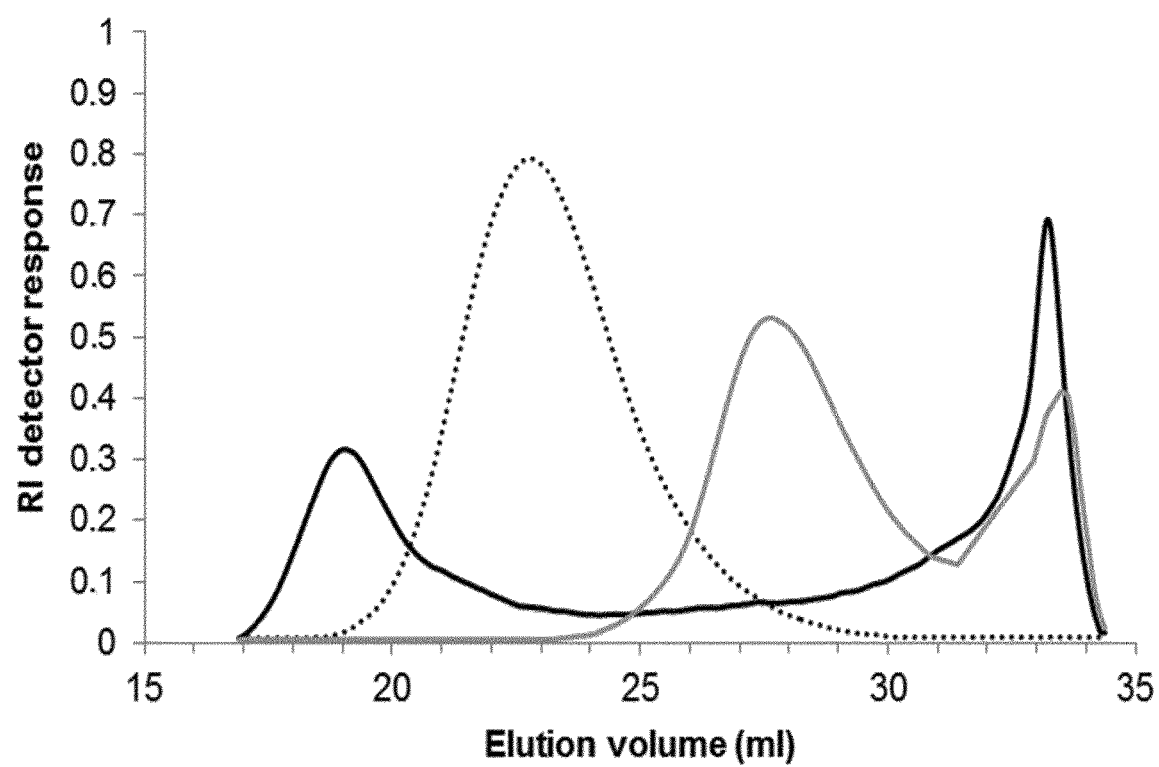

FIG. 8 shows HPSEC profiles of the reaction products obtained from 0.6% (w/v) amylose V, incubated with 40 μg ml$^{-1}$ of *Azotobacter chroococcum* NCIMB 8003 GTFD enzyme (pH 6.5) and *Lactobacillus reuteri* 121 GTFB enzyme (pH 4.7) for 24 h at 37° C. The dashed line corresponds to the elution profile of the amylose V. The solid black and grey lines correspond to the elution profiles of products synthesized by GTFD and GTFB enzymes, respectively.

Figure 9:
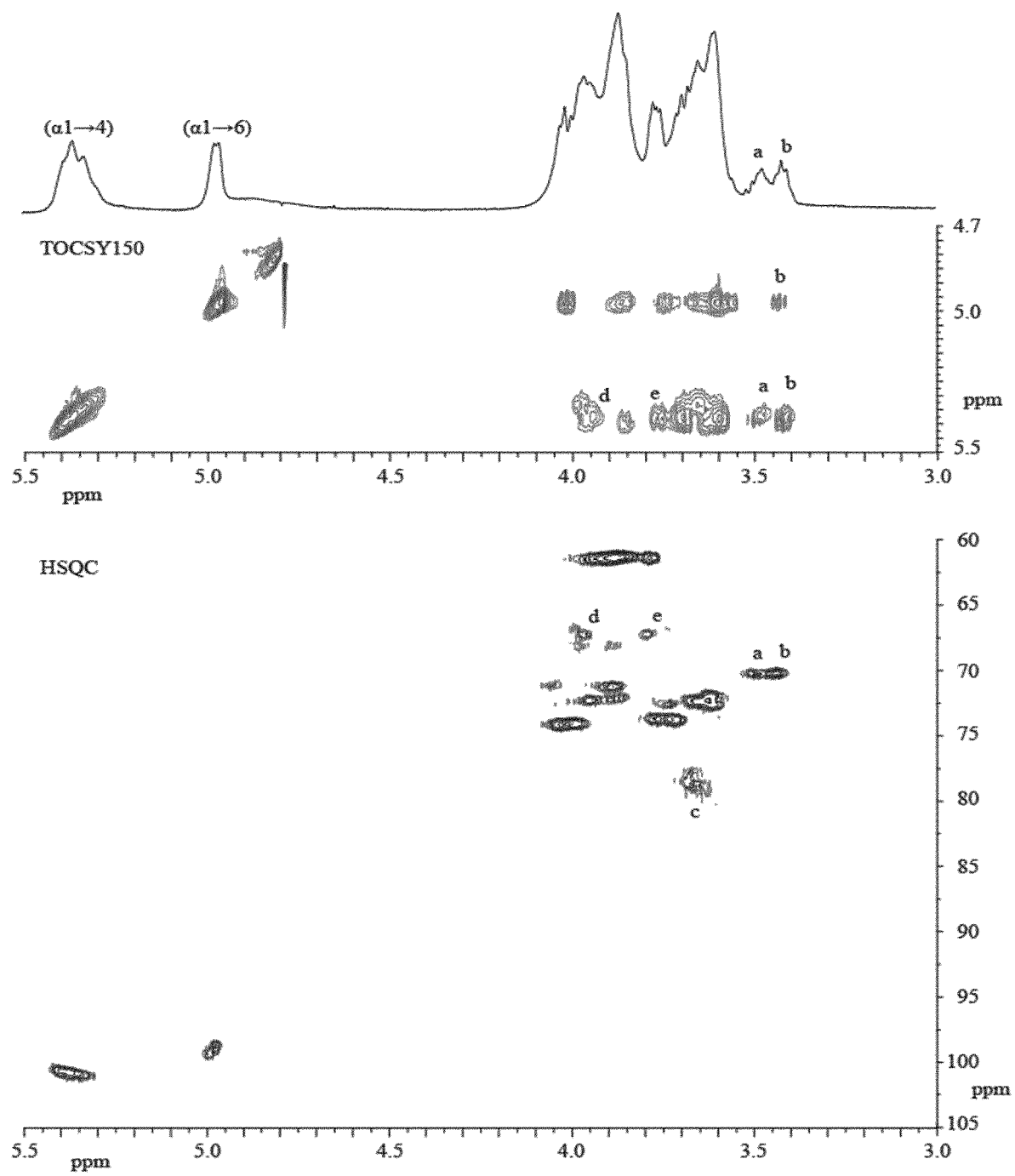

FIG. 9 shows a 500-MHz 1D $^1$HNMR spectrum, 2D H-$^1$H TOCSY spectra (mixing time 150 ms), and 2D $^{13}$C-$^1$H HSQC spectrum of the void-volume Bio-Gel P-2 polysaccharide fraction, obtained after 24 h incubation of 0.6% (w/v) amylose V with the *Azotobacter chroococcum* NCIMB 8003 GTFD enzyme (40 μg ml$^{-1}$) recorded at 300K in D$_2$O. Peaks for α(1→4) and α(1→6) anomeric signals have been indicated. Structural reporter peaks a. H-4 for 6-substituted Glc, b. H-4 for terminal Glc, c. for H-4 for 4-substituted Glc, d. H-6a for 6-substituted Glc and e. H-6b for 6-substituted Glc.

Figure 10:
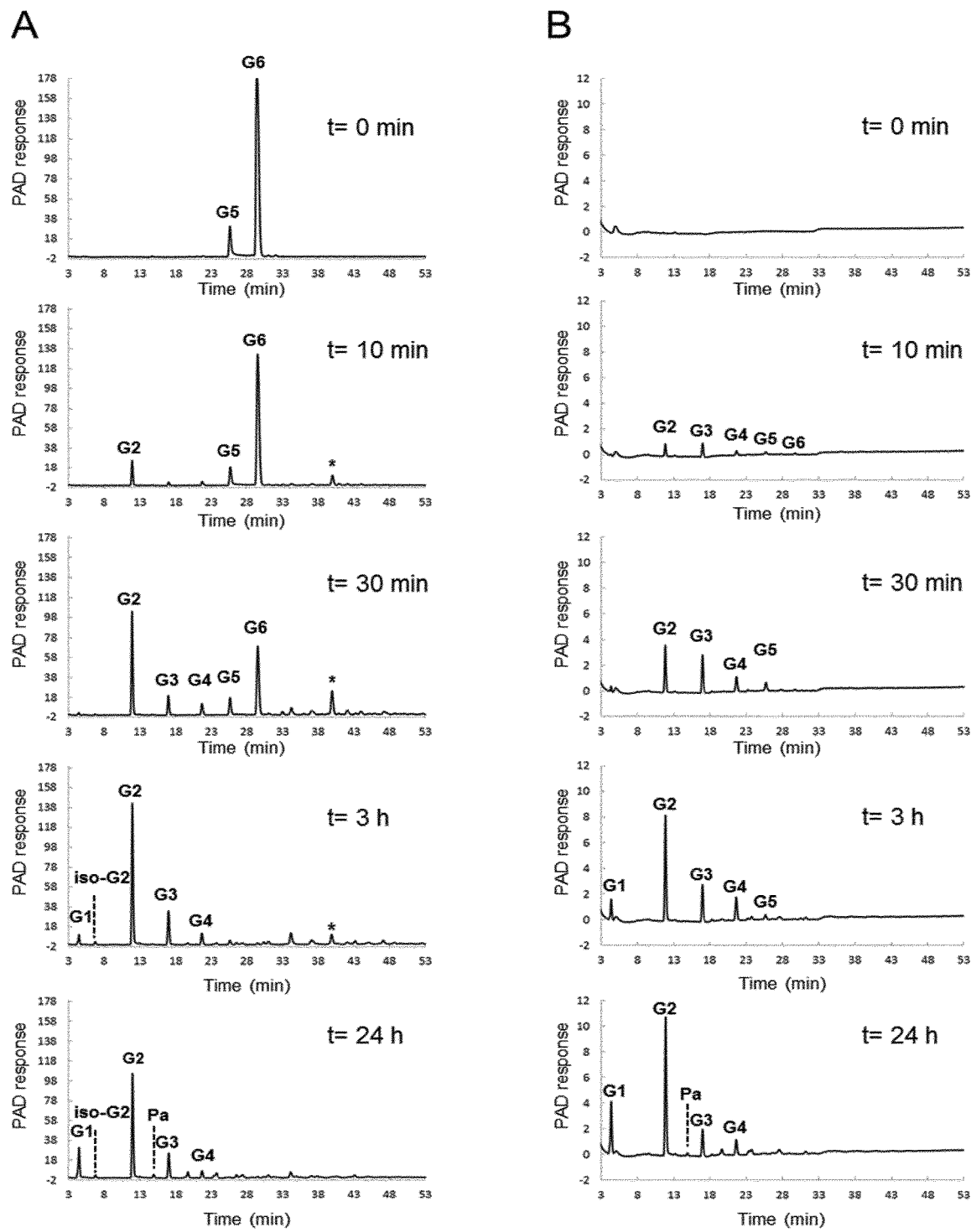

FIG. 10 shows an HPAEC-PAD profile of the oligosaccharide mixture formed upon incubation of the *Azotobacter chroococcum* NCIMB 8003 GTFD enzyme (20 μg ml$^{-1}$) with (A) maltohexaose and (B) amylose V for t=10 min, 30 min, 3 h, and 24 h (pH 6.5, 37° C.). The identity of peaks was assigned using commercial oligosaccharide standards.*Unidentified carbohydrate structure. G1, glucose; G2-G6, maltose to maltohexaose; iso-G2, isomaltose; Pa, panose.

Figure 11:
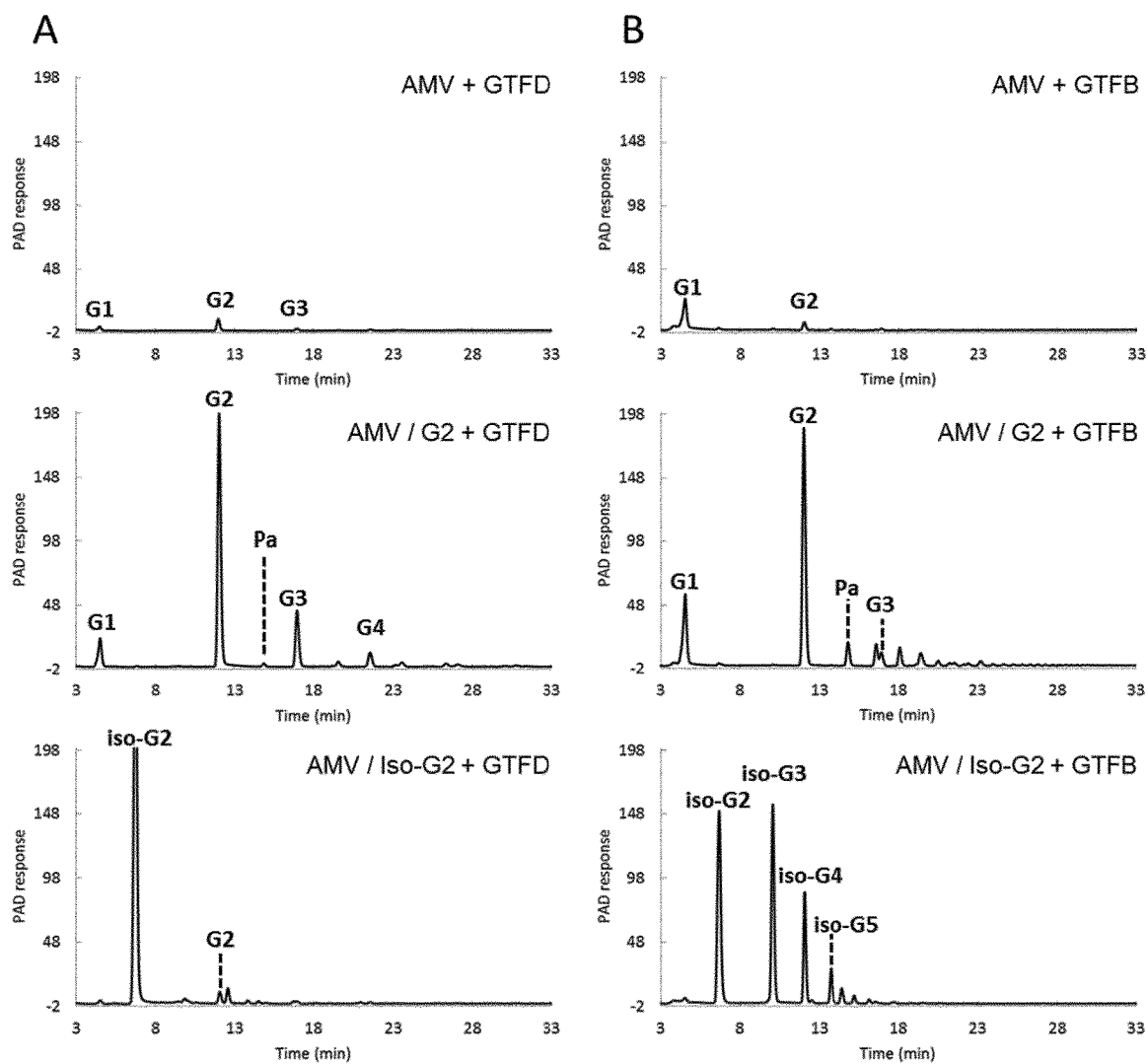

FIG. 11 shows an HPAEC-PAD profile of the oligosaccharide mixture formed upon the incubation of Azotobacter chroococcum NCIMB 8003 GTFD enzyme (40 μg ml$^{-1}$) (A) and Lactobacillus reuteri 121 GTFB enzyme (40 μg ml$^{-1}$) (B) with 0.35% amylose V (AMV) (donor substrate) or amylose V with 25 mM maltose or 25 mM isomaltose (acceptor substrates) for 24 h at 37° C. The identity of peaks was assigned using commercial oligosaccharide standards. G1, glucose; G2-G4, maltose to maltotetraose; iso-G2-iso-G5, isomaltose to isomaltopentaose; Pa, panose.

Figure 12:
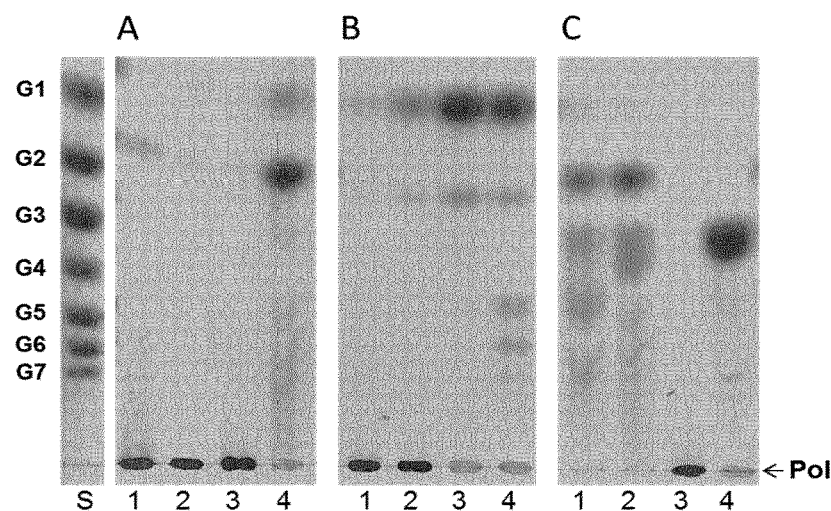

FIG. 12 shows a TLC analysis of the Azotobacter chroococcum NCIMB 8003 GTFD polymer, Lactobacillus reuteri 121 GTFA reuteran polymer and Lactobacillus reuteri 121 GTFB isomalto/malto-polysaccharide (IMMP), after treatment with (A) Aspergillus oryzae α-amylase, (B) Chaetomium erraticum dextranase and (C) Klebsiella planticola pullulanase M1. Lanes 1-3: product mixtures generated by the enzymatic hydrolysis of the GTFD polymer, reuteran and IMMP, respectively. Lane 4, positive controls for the α-amylase, dextranase and pullulanase treatments: starch (A), dextran (B) and pullulan (C). Lane S, standard: glucose (G1) to maltoheptaose (G7); Pol, polymer.

Figure 13:
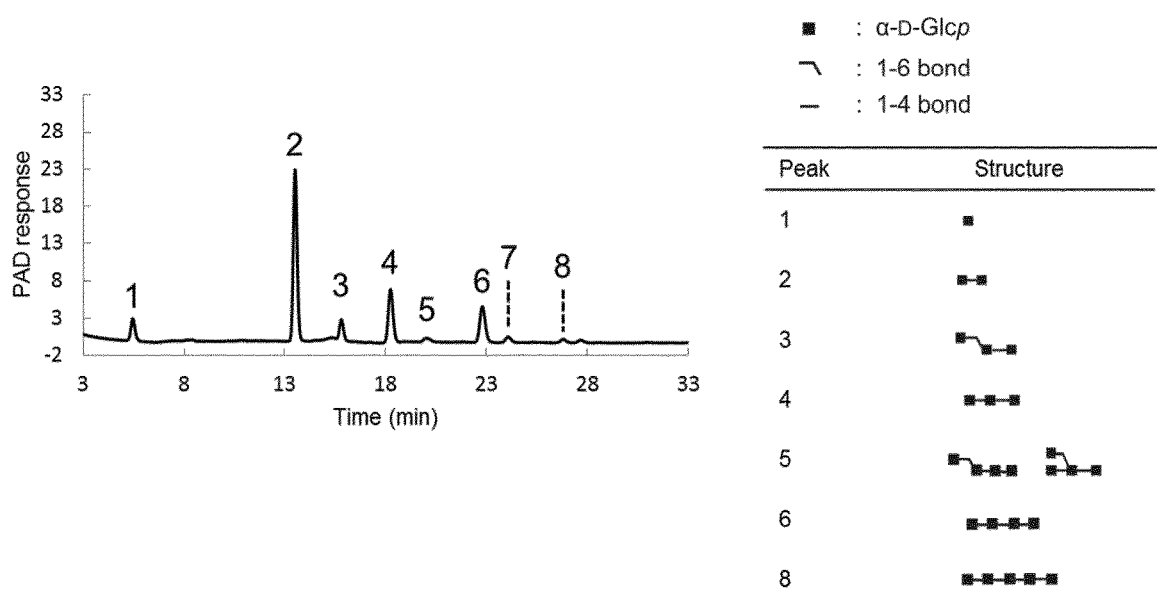

FIG. 13 shows an HPAEC-PAD profile of the oligosaccharides formed after treatment of the Azotobacter chroococcum NCIMB 8003 GTFD polymer with pullulanase M1. Established oligosaccharide structures are included. The identity of peaks 1-6 and 8 was assigned using commercial oligosaccharide standards and by comparison with the profile of the pullulanase hydrolysate of reuteran. Peak 7 corresponds to an oligosaccharide of DP5 with at least one α(1→6) linkage (van Leeuwen et al., 2008).

Figures 14, 15:
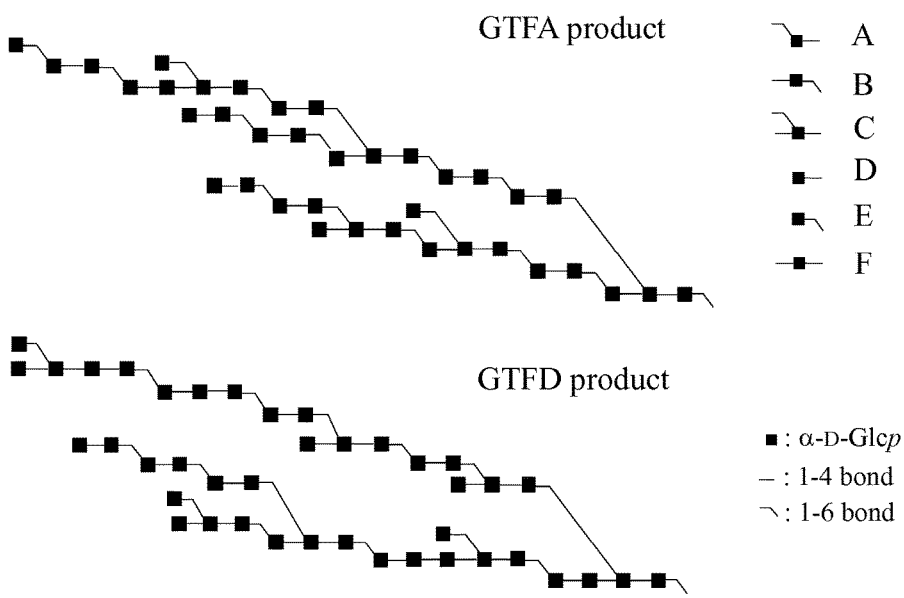

FIG. 14 is a visual representation of composite structures for the Lactobacillus reuteri 121 GTFA product from sucrose and the Azotobacter chroococcum NCIMB 8003 GTFD product from amylose. The composite structures contain all structural features established for the respective products. Quantities of each structural element fit with the combined data of 1D $^1$H NMR integration and methylation analysis.

FIG. 15 shows the sequence alignment of conserved motifs I-IV in the catalytic domains of Azotobacter chroococcum NCIMB 8003 and Paenibacilus beijingensis DSM 24997 GTFD enzymes. The seven strictly conserved amino acid residues in GH70 enzymes are indicated by the numbers 1 to 7 above the sequences. Residues forming acceptor subsites −1, +1 and +2 in GTF180-ΔN (Vujidčić-agar et al., 2010) are shown lightly shaded. Symbols: NU=nucleophile, A/B=general acid/base, TS=transition state stabilizer.

Figure 16:
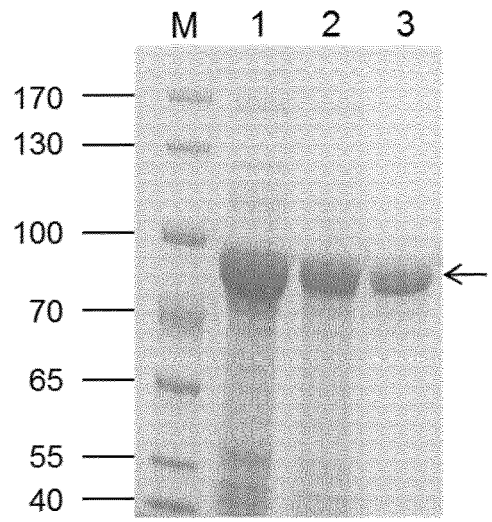

FIG. 16 shows SDS-PAGE analysis of P. beijingensis GTFD 4,6-α-glucanotransferase at different stages of purification. Lane M, molecular mass standards; lane 1, sample of E. coli cell free extract; lane 2, sample of the insoluble fraction after centrifugation of lysed cells; lane 3, purified GTFD enzyme after Ni-NTA agarose column chromatography. Bands corresponding to the P. beijingensis GTFD protein are indicated with an arrow.

Figure 17:
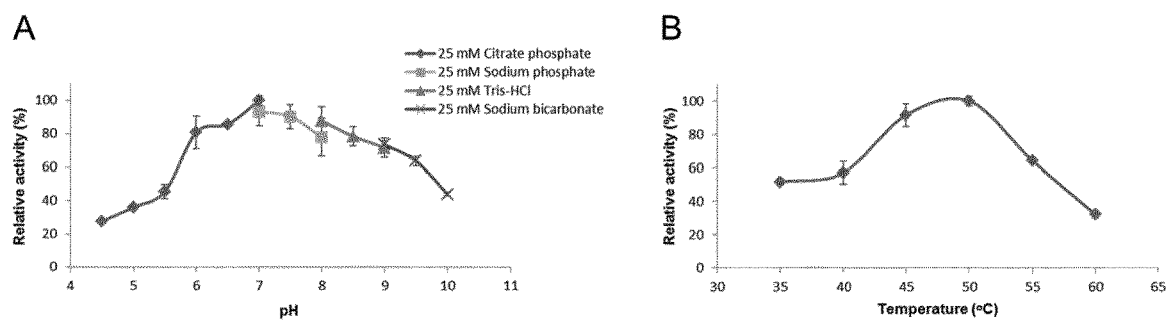

FIG. 17 shows biochemical properties of the purified GTFD enzyme from P. beijingensis. (A) Effect of pH on GTFD activity. Experiments were carried out at 40° C. and the relative enzyme activity was compared with enzyme activity at pH 7.0 (100% value). (B) Effect of temperature on GTFD activity. The assays were performed at pH 7.0 and relative activity was compared with the enzyme activity at 50° C. (100% value). The results are the mean of two replicates, and the bars indicate the standard error of two replicates.

Figure 18:
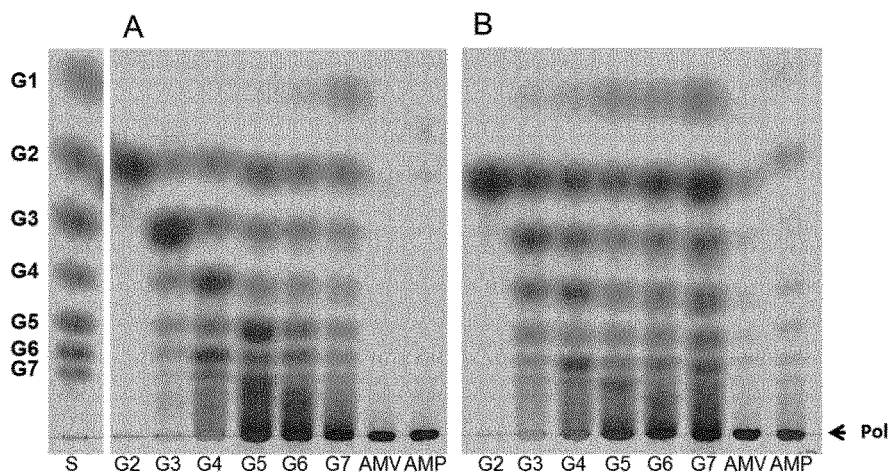

FIG. 18 shows TLC analysis of the products produced by the P. beijingensis GTFD (A) and A. chroococcum GTFD (B) enzymes at 40 μg ml$^{-1}$ from 25 mM malto-oligosaccharides (DP2-DP7), 0.6% (w v$^{-1}$) amylose V, and 0.6% (w v$^{-1}$) amylopectin. The reaction mixtures were incubated at 37° C. and pH 7.0 (P. beijingensis GTFD) or pH 6.5 (A. chroococcum GTFD) during 24 h. S, standard; G1, glucose; G2, maltose; G3, maltotriose; G4, maltotetraose; G5, maltopentaose; G6, maltohexaose; G7, maltoheptaose; AMV, amylose V; AMP, amylopectin; Pol, polymer.

Figure 19:
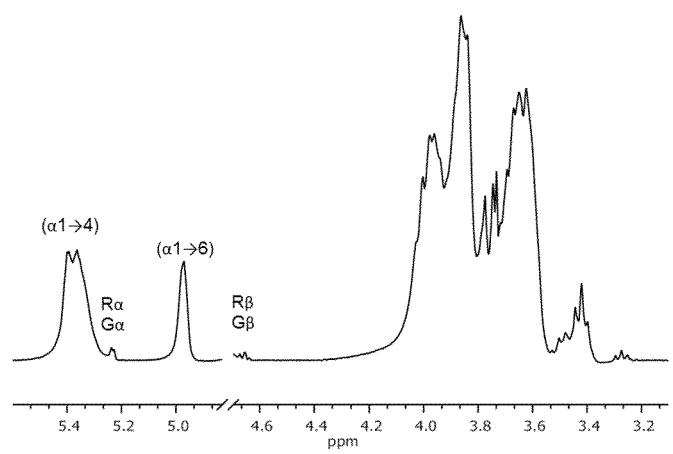

FIG. 19 shows one-dimensional 500-MHz $^1$H NMR spectra of the product mixtures generated after the incubation of 0.6% (w v$^{-1}$) amylose V with the P. beijingensis GTFD 4,6-α-glucanotransferase enzyme at 40 μg ml$^{-1}$ for 24 h at 37° C. and pH 7.0. The spectrum was recorded in D$_2$O at 25° C. Chemical shifts are shown in parts per million relative to the signal of internal acetone (δ=2.225). Gα/β and Rα/β indicate the anomeric signals corresponding to the D-Glcp units and the reducing −(1→4)-D-Glcp units, respectively.

Figure 20:
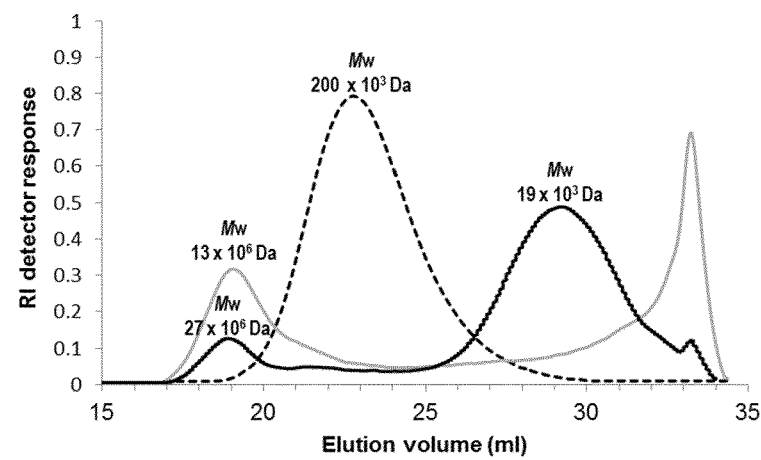

FIG. 20 shows HPSEC chromatograms of the product mixtures obtained by the incubation of 0.6% (w v$^{-1}$) amylose V with 40 μg ml$^{-1}$ of A. chroococcum GTFD enzyme (pH 6.5) and P. beijingensis GTFD enzyme (pH 7.0) for 24 h at 37° C. The dashed line corresponds to the elution profile of the starting amylose V. The solid black and grey lines correspond to the elution profiles of products synthesized by P. beijingensis and A. chroococcum GTFD enzymes, respectively.

Figure 21:
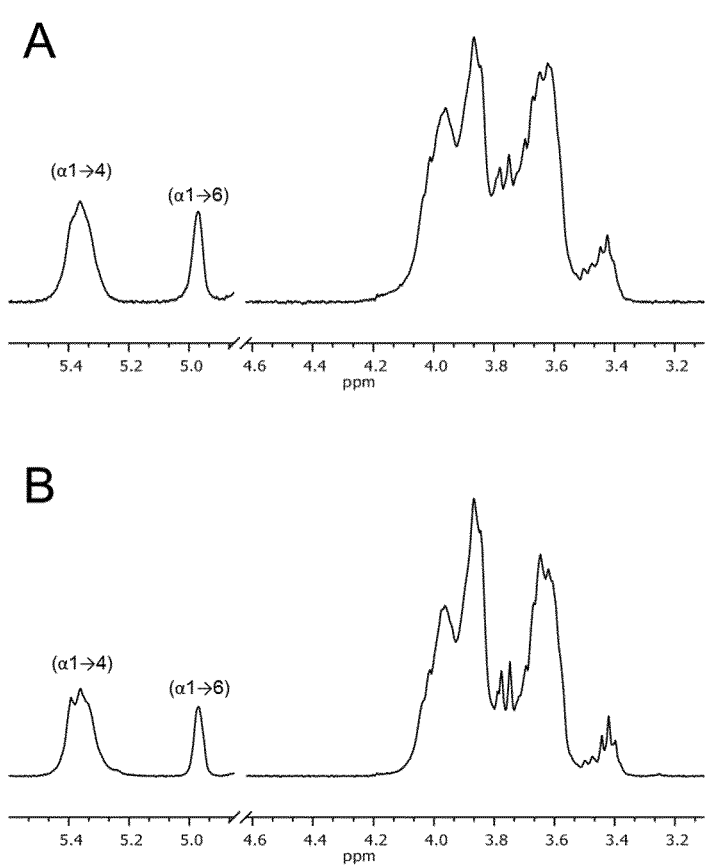

FIG. 21 shows 500-MHz $^1$H NMR spectra of the high- (HMM) (A) and low molecular mass (LMM) (B) polysaccharides produced by the P. beijingensis GTFD enzyme, isolated by size-exclusion chromatography on a Sephadex S200 column. The reaction products were obtained from 0.6% (w v$^{-1}$) amylose V, incubated with 40 μg ml$^{-1}$ of the P. beijingensis GTFD enzyme for 24 h at 37° C. and pH 7.0. The spectra were recorded in D$_2$O at 25° C. Chemical shifts are shown in parts per million relative to the signal of internal acetone (δ=2.225). Peaks for α(1→4) and α(1→6) anomeric signals have been indicated.

Figure 22:
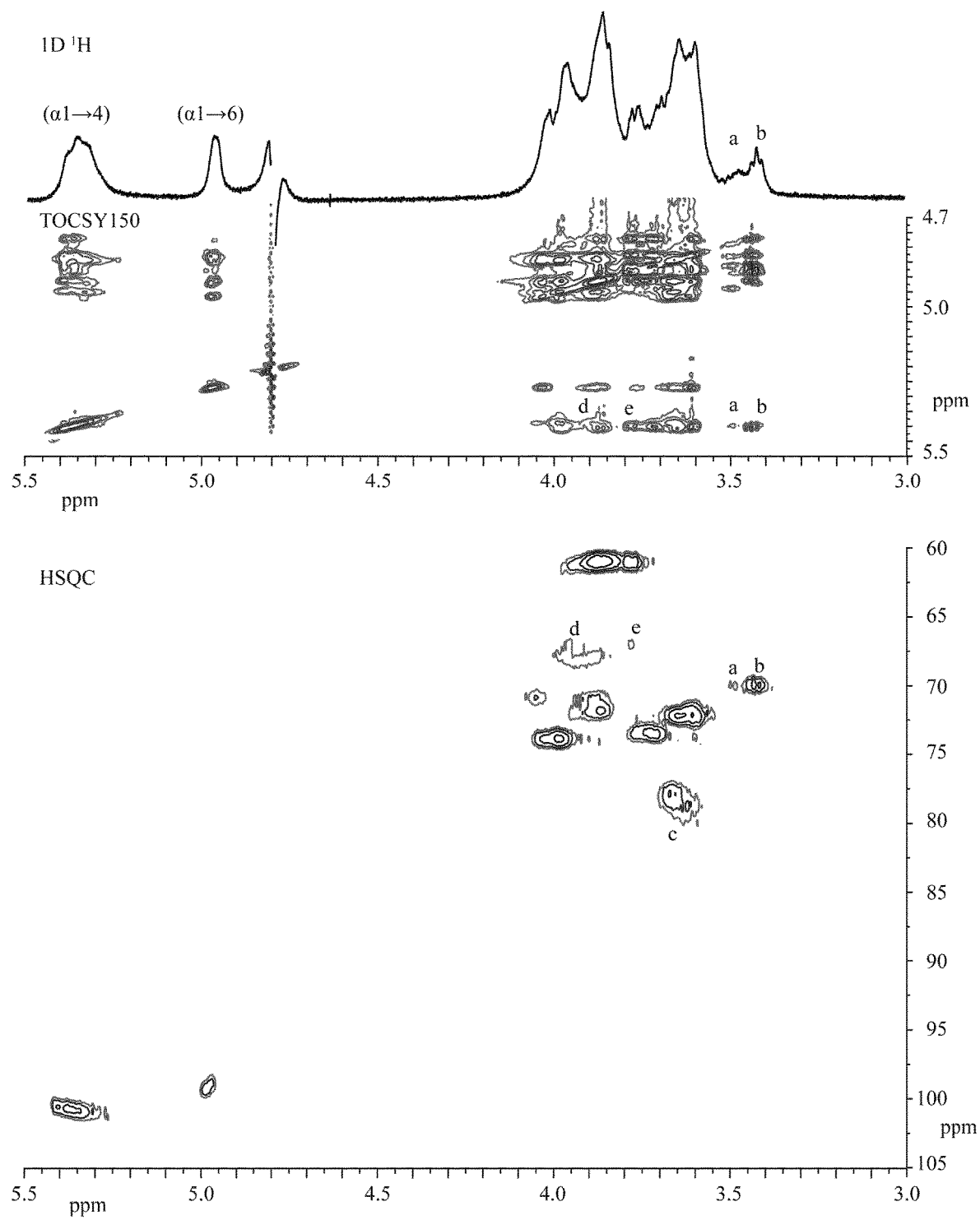

FIG. 22 shows a 500-MHz 1D $^1$H NMR spectrum, 2D $^1$H-$^1$H TOCSY spectra (mixing time 150 ms), and 2D$^{13}$C-$^1$H HSQC spectrum of the HMM product of P. beijingensis GTFD enzyme incubated with amylose V, recorded at 298K in D$_2$O. Peaks for α(1→4) and α(1→6) anomeric signals have been indicated. Structural reporter peaks a: H-4 for 6-substituted Glcp, b: H-4 for terminal Glcp, c: for H-4 for 4-substituted Glcp, d: H-6a for 6-substituted Glcp and e: H-6b for 6-substituted Glcp.

Figure 23:
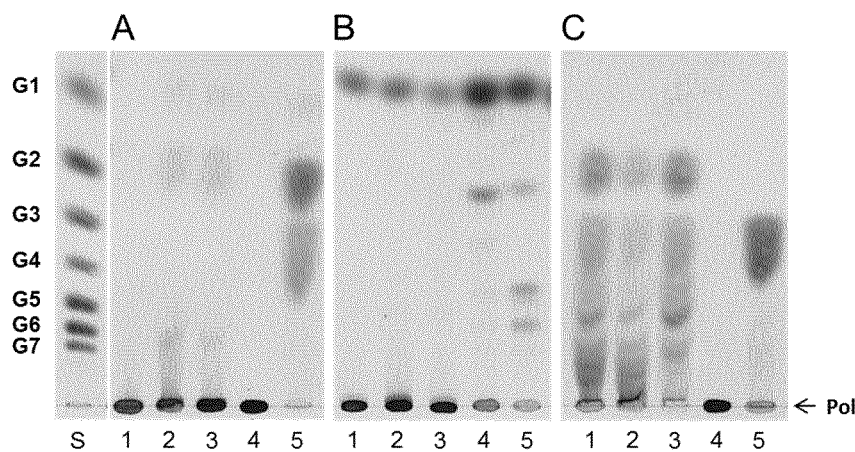

FIG. 23 shows enzymatic treatment of the P. beijingensis DSM 24997 GTFD HMM and LMM polymers, A. chroococcum NCIMB 8003 GTFD reuteran-like polymer, and L. reuteri 121 GTFB isomalto/malto-polysaccharide (IMMP). Reaction mixtures containing 5 mg ml$^{-1}$ of α-glucans were incubated separately with a high dose of (A) Aspergillus oryzae α-amylase, (B) Chaetomium erraticum dextranase and (C) Klebsiella planticola pullulanase M1 for 48 h at 37° C. and subjected to TLC analysis. Lanes 1-4: reaction products generated by the enzymatic treatment of the P. beijingensis GTFD HMM polymer, P. beijingensis GTFD LMM polymer, reuteran-like polymer, and IMMP, respectively. Lane 5, positive controls for the α-amylase, dextranase and pullulanase digestions: amylose (A), dextran (B) and pullulan (C). Lane S, standard: glucose (G1) to maltoheptaose (G7); Pol, polymer.

Figure 24:
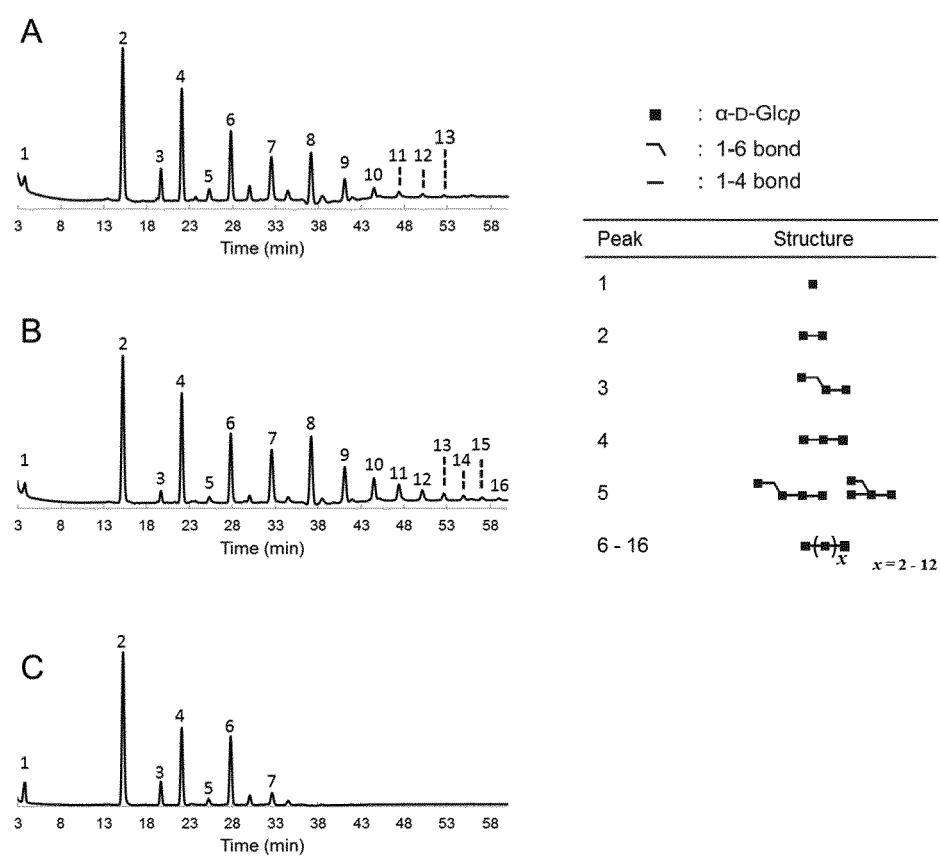

FIG. 24 shows HPAEC-PAD profiles of the oligosaccharides formed after treatment of the *P. beijingensis* GTFD HMM polymer (A), *P. beijingensis* GTFD LMM polymer (B), and *A. chroococcum* GTFD polymer (C) with pullulanase M1. Established oligosaccharide structures are included. The identity of peaks 1-16 was assigned using commercial oligosaccharide standards and by comparison with the profile of the pullulanase hydrolysate of reuteran.

Figure 25:
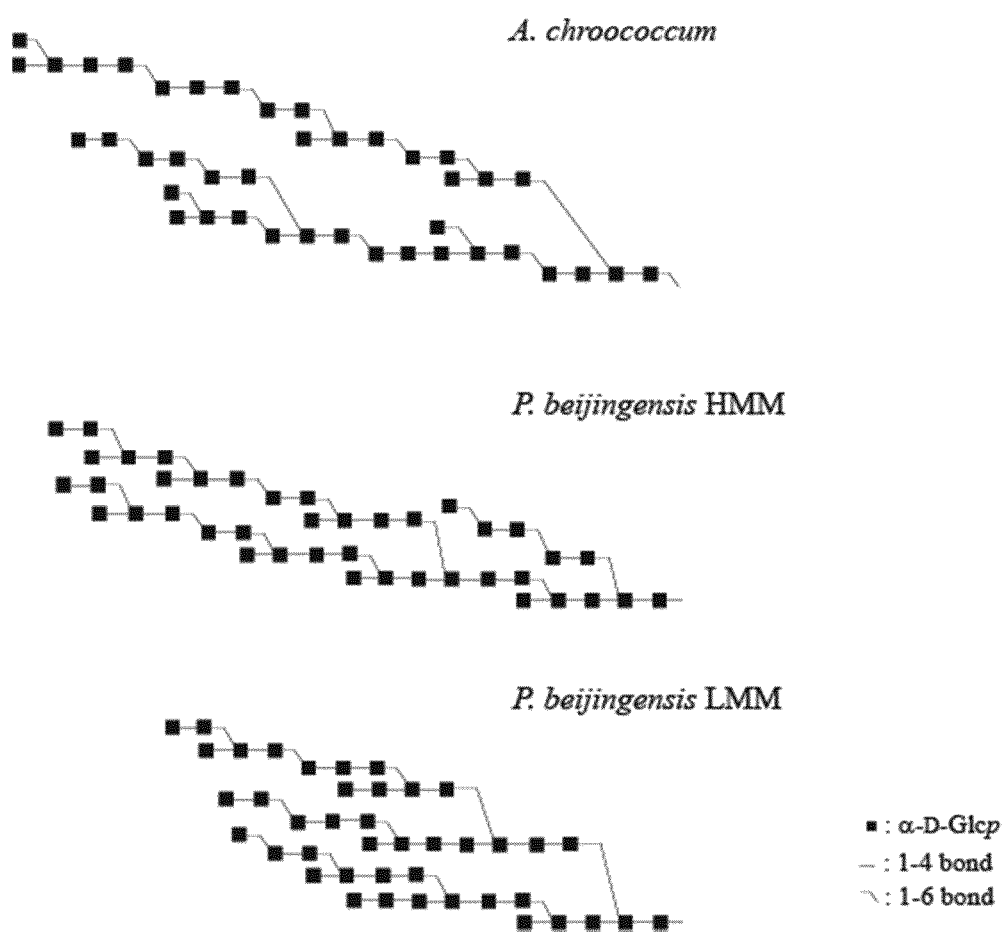

FIG. 25 is a visual representation of composite structures for the *A. chroococcum* NCIMB 8003 GTFD polymer, the HMM *P. beijingensis* GTFD polymer and the LMM *P. beijingensis* GTFD polymer formed from amylose V. The composite structures contain all structural features established for the respective products. Quantities of each structural element fit with the combined data of 1D $^1$H NMR integration and methylation analysis, as well as enzymatic degradation studies with α-amylase, dextranase and pullulanase.

Figure 26:
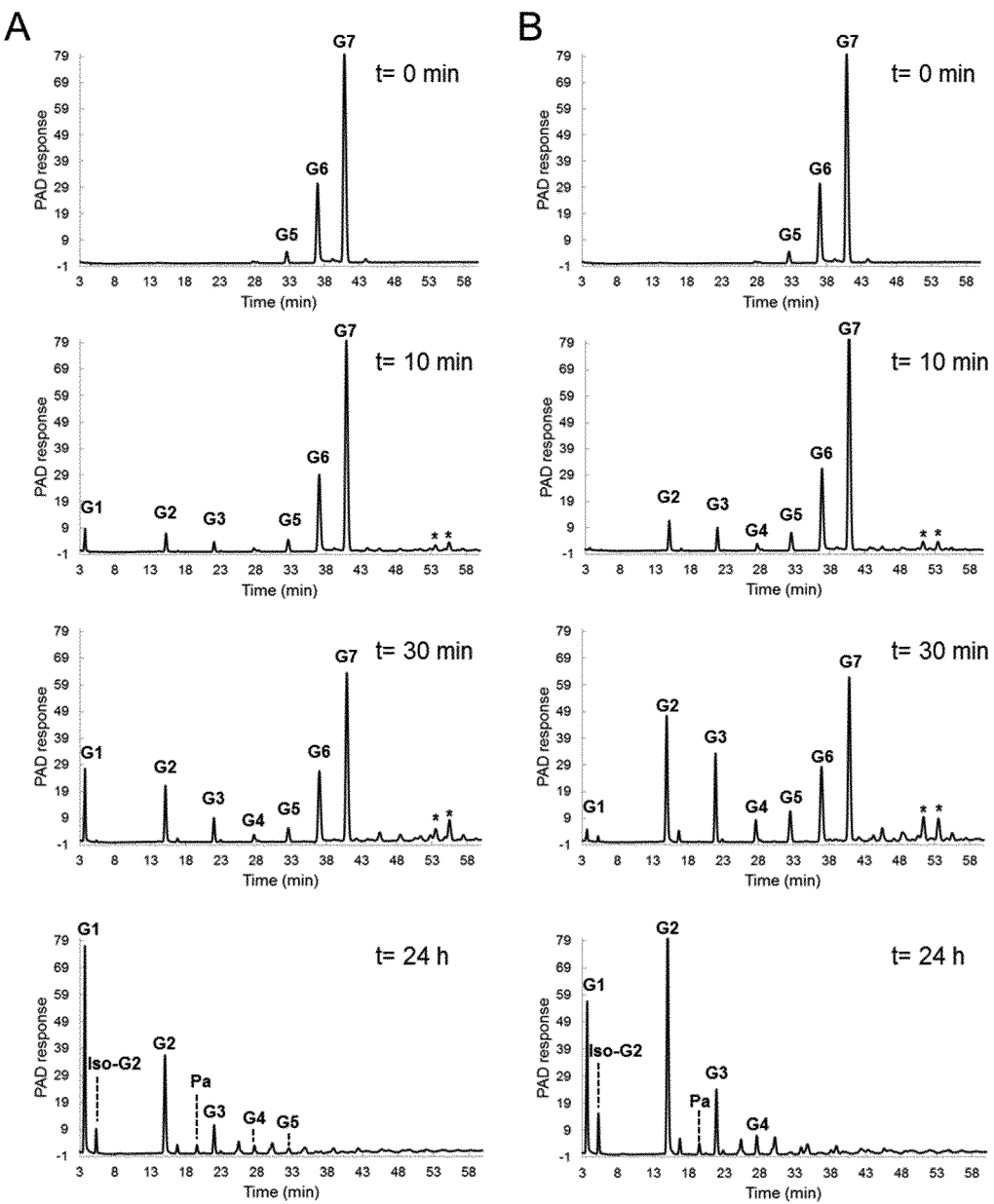

FIG. 26 shows HPAEC-PAD profiles of the oligosaccharide mixtures formed upon incubation of maltoheptaose with *P. beijingensis* GTFD (A) and *A. chroococcum* (B) GTFD enzymes (20 μg ml$^{-1}$) for t=10 min, 30 min, 3 h, and 24 h, at 37° C. and pH 7.0 and pH 6.5, respectively. The identity of peaks was assigned using commercial oligosaccharide standards.*Unidentified carbohydrate structures. G1, glucose; G2-G6, maltose to maltohexaose; iso-G2, isomaltose; Pa, panose.

Figure 27:
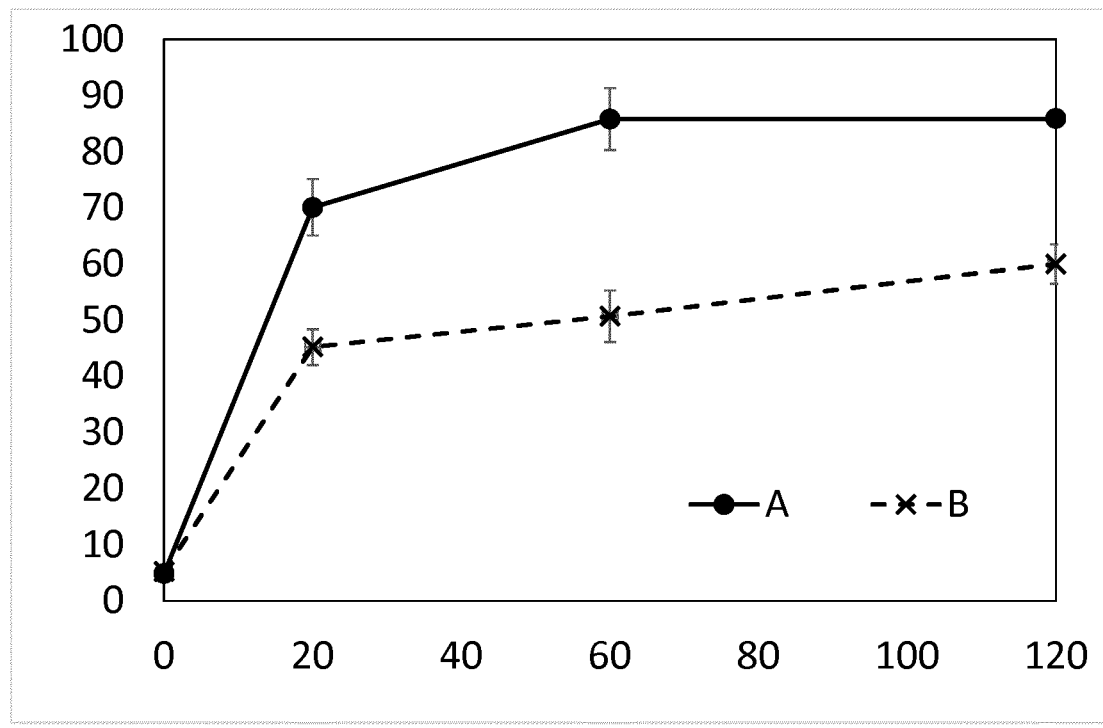

FIG. 27 is a plot of in vitro digestibility of gelatinized wheat starch treated with *A. chroococcum* GTFD (B) compared to untreated gelatinized wheat starch (A). The graph plots % hydrolysed sample versus time in minutes.

Figure 28:
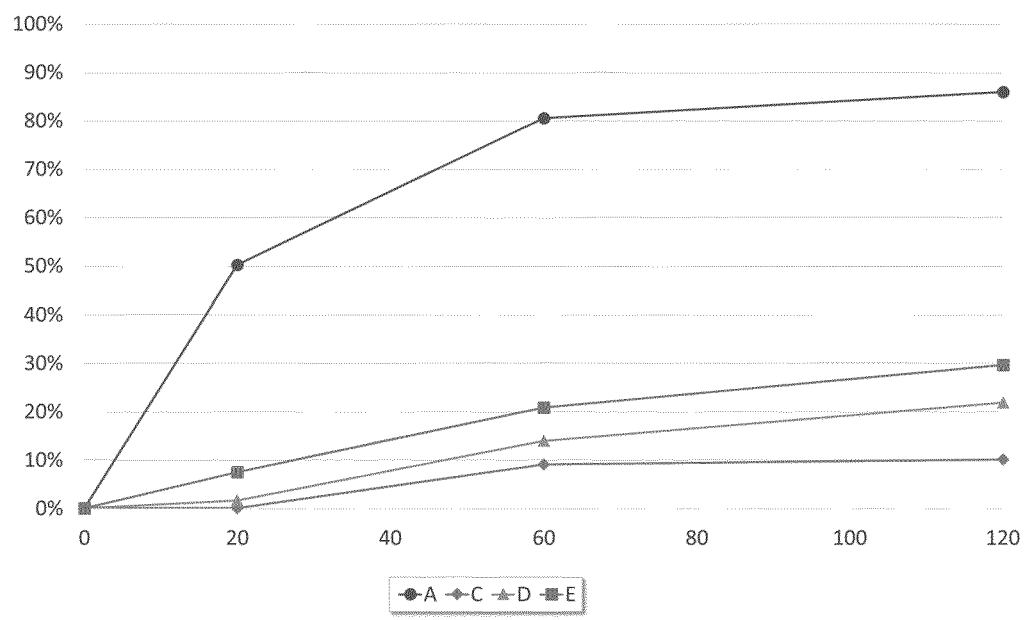

FIG. 28 is a plot of in vitro digestibility of *A. chroococcum* GTFD—high molecular mass (C), *P. beijingensis* GTFD—high molecular mass (D), and *P. beijingensis* GTFD—low molecular mass (E) products from Amylose V compared to gelatinized wheat starch (A). The graph plots % hydrolysed sample versus time in minutes.

DETAILED DESCRIPTION OF THE INVENTION

Consequently the present invention relates in part to a method of producing an α-glucan with a ratio of branching of at least 8% (for example at least 12%) comprising contacting a polysaccharide or oligosaccharide substrate comprising at its non-reducing end at least two α(1→4) linked D-glucose units with an α-glucanotransferase enzyme capable of cleaving α(1→4) glucosidic linkages and making new alternating α(1→4) and α(1→6) glucosidic linkages with α(1→4,6) branching points, wherein said α-glucanotransferase is selected from the group consisting of GTFB, GTFC and GTFD types of enzyme (for example a GTFD type of enzyme), or a functional homolog thereof having the specified enzymatic activity. For example, the α-glucanotransferase enzyme in the method of the invention may be capable of cleaving α(1→4) glucosidic linkages and transferring malto-oligosaccharides up to DP5, resulting in the formation of single α(1→6) linkages, in both alternating and branching patterns. Polysaccharides are polymeric carbohydrate molecules composed of long chains of monosaccharide units bound together by glycosidic linkages. Oligosaccharides are saccharide polymers containing a small number (typically three to nine) of monosaccharides. An example of a substrate comprising at its non-reducing end at least two α(1→4) linked D-glucose units is amylose.

The method of the invention may comprise contacting a polysaccharide or oligosaccharide substrate comprising at its non-reducing end at least two α(1→4) linked D-glucose units with an α-glucanotransferase enzyme capable of cleaving α(1→4) glucosidic linkages and making new alternating α(1→4) and α(1→6) glucosidic linkages with (for example together with) α(1→4,6) branching points without forming consecutive α(1→6) glucosidic linkages, wherein said α-glucanotransferase is selected from the group consisting of GTFB, GTFC and GTFD types of enzyme, or a functional homolog thereof having the specified enzymatic activity. In the present specification, the abbreviation GTF refers to glucanotransferase.

The alternating α(1→4) and α(1→6) glucosidic linkages may be interspersed with some consecutive α(1→4) glucosidic linkages, such a structure can also be described as chains of α(1→4) linked D-glucose units interspersed with α(1→6) glucosidic linkages. Single α(1→6) glucosidic linkages between one or more α(1→4) glucosidic linkages as may be formed in the method of the invention are sometimes referred to as "bridging" α(1→6) linkages. The notation (α1→4) may be used instead of α(1→4) to refer to a 1→4 α linkage, but these are equivalent, as are (α1→6) and α(1→6).

The method of the invention may comprise contacting a polysaccharide or oligosaccharide substrate comprising at its non-reducing end at least two α(1→4) linked D-glucose units with an α-glucanotransferase enzyme capable of cleaving α(1→4) glucosidic linkages and making new α(1→6) glucosidic linkages to form structures having chains of α(1→4) linked D-glucose units interspersed with α(1→6) glucosidic linkages and having α(1→4,6) branching points, without forming consecutive α(1→6) glucosidic linkages, wherein said α-glucanotransferase is selected from the group consisting of GTFB, GTFC and GTFD types of enzyme, or a functional homolog thereof having the specified enzymatic activity.

In the context of the present invention, the ratio of branching is defined as the total number of branching anhydroglucose units (AGU), i.e. AGU being bound to three other units, with respect to the total number of AGU of a molecule. The ratio of branching can be determined by methods known in the art, such as methylation with gas chromatography. The α-glucan produced by the method of the invention may have a ratio of branching of at least 8%, for example at least 10%, for example at least 15%.

The α-glucan produced by the method of the invention may comprise at least one α(1→4) glucosidic linkage adjacent to an α(1→6) glucosidic linkage and at least one α(1→4,6) branching point. The α-glucan produced by the method of the invention may comprise alternating α(1→4) and α(1→6) glucosidic linkages and have α(1→4,6) branching points, for example the α-glucan produced by the method of the invention may comprise between 40 and 50 percent consecutive α(1→4) glucosidic linkages, between 12 and 21 percent single α(1→6) glucosidic linkages in alternating pattern and between 8 and 25 percent α(1→4,6) branching points, for example between 12 and 21 percent α(1→4,6) branching points, for example between 15 and 20 percent α(1→4,6) branching points. The α-glucan produced by the method of the invention may have less than 1% consecutive α(1→6) glucosidic linkages, for example it may have less than 0.5% consecutive α(1→6) glucosidic linkages, for further example it may have no consecutive α(1→6) glucosidic linkages.

The α-glucanotransferase in the method of the invention may comprise an amino acid sequence having at least 80% identity to SEQ ID NO:1 (for example at least 90, 95, 96, 97, 98, or 99% identity to SEQ ID NO:1). The α-glucanotransferase in the method of the invention may consist of an amino acid sequence having at least 80% identity to SEQ ID NO:1 (for example at least 90, 95, 96, 97, 98, or 99% identity to SEQ ID NO:1).

```
                                         (SEQ ID NO: 1)
mraspsqffa isllsiaisg llsgaavaap aptaleqvpd gkggvkwqev thdasaeeeq kgqdpkkflg iqaittepdg svkvemgkpe vrqpasgdvf vsnekldehv ifqafalyqp ndnatykalt enapqlaqwg itdvwspppy raasdskyge gyaiadrydl gaydkgptky gtadelkaai galhnndiri qvdvvpnqii glnerhvlpv tgvdmygkpm npfldhylys tyskgsapgq aehgvikewd yfhfhgtttq yqglfrvlsd anstlyrylg pnhpenylpa flaesdaaky gkintidgyl ladtwfaven aesenavyap lflyyeeprn gvveqtfmdf arengytgsd ediratmlae lrmtpnpigp lmdeylaaqp gyskksedda kvtalrydgp endashigtn vldfeflvgn dldtiredvq qeqlnwqkyl ldfgfdgfri daashintdm lrdevtqrln hfagedvneh lsyiesyvtq qvdflqsnny gqmamdagpf sglmfsfgrd waplryafea slidrvnggp alpnwsfvnn hdqehnilvt vplteeeagg yepnsqpyel rqlekydadr nsvekqwaph nvpamyaill ttkdtvptvf ygdmfvsskp ymstptpyrd divnilklrk qfakgeqvir yensntgsng edlvsnirlg ndrktgvavv agnnpaldtt itvdmgaqhr nqwfvdamgy qperlktdkd grltvqvkgt qnvdvkgyla awvpdlqaqe
```

The α-glucanotransferase in the method of the invention may be an *Azotobacter chroococccum* GTFD enzyme for example the α-glucanotransferase in the method of the invention may be an *Azotobacter chroococccum* NCIMB 8003 GTFD enzyme. The method of the invention for producing an α-glucan with a ratio of branching of at least 8% may comprise contacting a polysaccharide or oligosaccharide substrate comprising at its non-reducing end at least two α(1→4) linked D-glucose units with an *Azotobacter chroococccum* GTFD enzyme.

A further aspect of the invention provides a method for producing an α-glucan with a ratio of branching of at least 8%, the method comprising contacting a polysaccharide or oligosaccharide substrate, comprising at its non-reducing end at least two α(1→4) linked D-glucose units, with an α-glucanotransferase enzyme comprising (for example consisting of) an amino acid sequence having at least 80% identity to SEQ ID NO:92 (for example at least 90, 95, 96, 97, 98, or 99% identity to SEQ ID NO:92). SEQ ID NO:92 is the sequence of *Paenibacillus beijingensis* DSM 24997 GFTD enzyme, Gen bank accession WP_052702730.1.

The α-glucanotransferase in the method of the invention may comprise an amino acid sequence having at least 80% identity to SEQ ID NO:92 (for example at least 90, 95, 96, 97, 98, or 99% identity to SEQ ID NO:92). The α-glucanotransferase in the method of the invention may consist of an amino acid sequence having at least 80% identity to SEQ ID NO:92 (for example at least 90, 95, 96, 97, 98, or 99% identity to SEQ ID NO:92).

The α-glucanotransferase in the method of the invention may be a *Paenibacillus beijingensis* GTFD enzyme for example the α-glucanotransferase in the method of the invention may be a *Paenibacillus beijingensis* DSM 24997 GFTD enzyme. *Paenibacillus beijingensis* DSM 24997 is the type strain of *P. beijingensis*, also known as ACCC 03082, and may be obtained from Leibniz-Institut DSMZ—Deutsche Sammlung von Mikroorganismen and Zellkulturen GmbH. The method of the invention for producing an α-glucan with a ratio of branching of at least 8% may comprise contacting a polysaccharide or oligosaccharide substrate comprising at its non-reducing end at least two α(1→4) linked D-glucose units with a *Paenibacillus beijingensis* GTFD enzyme.

An aspect of the invention provides a method for producing an α-glucan with a ratio of branching of at least 8%, the method comprising contacting a polysaccharide or oligosaccharide substrate, comprising at its non-reducing end at least two α(1→4) linked D-glucose units, with α-glucanotransferase comprising an amino acid sequence having at least 80% identity to SEQ ID NO:92.

The substrate in the method of the invention may have a degree of polymerization of at least three, for example it may comprise at least three D-glucose units. The degree of polymerization is the number of monomeric units in a polymer or oligomer molecule. For example, the substrate in the method of the invention may have a degree of polymerization of at least four, for example it may comprise at least four D-glucose units. The substrate in the method of the invention may be selected from the group consisting of starch (for example waxy starch or high amylose starch), starch derivatives, malto-oligosaccharides, amylose, amylopectin, maltodextrins, α(1→4) glucans and combinations thereof. Starch derivatives are prepared by physically, enzymatically, or chemically treating native starch to change its properties.

The substrate in the method of the invention may be comprised within another material, for example the substrate may be starch provided in the form of flour. It is advantageous to be able to convert polysaccharides or oligosaccharides comprised within food ingredients into α-glucans with lower digestibility, for example branched α-glucans. Such a conversion may increase the fibre content of the ingredients and/or may aid in reducing the calorie content of the ingredients. The method of the invention may be performed as part of a food processing operation, for example the α-glucanotransferase enzyme may be applied to food ingredients during a process to produce a food product. The substrate may be comprised within a material which already has a positive nutritional profile, for example the substrate may be comprised within whole grain flour.

The extent to which the polysaccharide or oligosaccharide substrate may be converted by the α-glucanotransferase enzyme in the method of the invention can be adjusted by limiting the time of reaction. Partially converted substrates will provide different physical properties. The production of α-glucan in the method of the invention may be stopped before the reaction between the substrate and the α-glucanotransferase enzyme has reached completion, for example it may be stopped by denaturing (e.g. by heat) or removing the enzyme.

The α-glucanotransferase enzyme in the method of the invention may be immobilized, for example immobilized before contacting the polysaccharide or oligosaccharide substrate. Such immobilization techniques are well known in the art. Removal of the enzyme (discussed above) may be facilitated by immobilization of the enzyme. Immobilization techniques may be selected from the group consisting of covalent binding, entrapment, physical adsorption, cross-linking and combinations of these. In immobilization by covalent binding, enzymes are covalently linked to a support through the functional groups in the enzymes that are not essential for the catalytic activity. Oxides materials such as alumina, silica, and silicated alumina can be used for covalent binding of the enzyme. In immobilization by entrapment the enzyme is localized within the lattice of a polymer matrix or membrane. Entrapment methods are classified into five major types: lattice, microcapsule, liposome, membrane, and reverse micelle. The enzyme is entrapped in the matrix of various synthetic or natural polymers. Alginate, a naturally occurring polysaccharide that forms gels by ionotropic gelation is one such immobilization matrix. Immobilization by physical adsorption is the simplest and the oldest method of immobilizing enzymes onto carriers. Immobilization by adsorption is based on the physical interactions between the enzymes and the carrier, such as hydrogen bonding, hydrophobic interactions, van der Waals force, and their combinations. Adsorption is generally less disruptive to the enzymes than chemical means of attachment. Immobilization by cross-linking utilizes bi- or multifunctional compounds, which serve as the reagent for intermolecular cross-linking of the enzymes. Cross-linking may be used in combination with other immobilization methods such as adsorption or entrapment.

The polysaccharide or oligosaccharide substrate may be contacted with an α-glucanotransferase enzyme in the method of the invention at a temperature of between 30° C. and 75° C. (for example between 40° C. and 75° C., for example between 50° C. and 70° C., for example between 35° C. and 45° C.) and a pH of between 4.8 and 8.0 (for example between 5.5 and 7.5, for example between 6.0 and 7.0).

In a further embodiment the present invention pertains to an α-glucan comprising alternating $\alpha(1\rightarrow4)$ and $\alpha(1\rightarrow6)$ glucosidic linkages and having $\alpha(1\rightarrow4,6)$ branching points wherein the α-glucan has a ratio of branching of at least 12% (for example at least 15%), has more than 1 wt. % maltopentose units and has an average molecular mass between $1\times10^6$ Da and $40\times10^6$ Da, for example, an average molecular mass between $5\times10^6$ Da and $30\times10^6$ Da, for example, an average molecular mass between $10\times10^6$ Da and $20\times10^6$ Da. The α-glucan according to the invention may comprise between 40 and 50 percent consecutive $\alpha(1\rightarrow4)$ glucosidic linkages, between 12 and 21 percent single $\alpha(1\rightarrow6)$ glucosidic linkages in alternating pattern and between 12 and 25 percent $\alpha(1\rightarrow4,6)$ branching points, for example between 12 and 21 percent $\alpha(1\rightarrow4,6)$ branching points, for example between 15 and 20 percent $\alpha(1\rightarrow4,6)$ branching points. The α-glucan according to the invention may have less than 1% consecutive $\alpha(1\rightarrow6)$ glucosidic linkages, for example it may have less than 0.5% consecutive $\alpha(1\rightarrow6)$ glucosidic linkages, for further example it may have no consecutive $\alpha(1\rightarrow6)$ glucosidic linkages. The α-glucan of the invention is similar to the reuteran synthesized by the L. reuteri 121 GTFA glucansucrase from sucrose, regarded as a health promoting food ingredient, but has some important differences. The ratio of branching is higher, for example in the samples analysed in table 3 it can be seen that Azotobacter chroococcum NCIMB 8003 GTFD enzyme produces 18% branching compared to 11% for L. reuteri 121 GTFA enzyme. The more branching is present in an α-glucan, the less access is provided to digestive enzymes and so the α-glucan could present a lower digestibility. The α-glucan of the invention also comprises maltopentose units in its structure (see FIG. 14) which are not present in reuteran, for example reuteran produced by the L. reuteri 121 GTFA enzyme. Higher amounts of consecutive $\alpha(1\rightarrow4)$ linkages, for example maltopentose units, may provide particular physical properties such as gelling and viscosity modification which provide useful applications, for example in foodstuffs.

The α-glucan of the invention may have $\alpha(1\rightarrow4,6)$ branching points, a ratio of branching of at least 12%, more than 1 wt. % maltopentose units, less than 1% consecutive $\alpha(1\rightarrow6)$ glucosidic linkages (for example less than 0.5% consecutive $\alpha(1\rightarrow6)$ glucosidic linkages, for further example no consecutive $\alpha(1\rightarrow6)$ glucosidic linkages), an average molecular mass between $1\times10^6$ Da and $40\times10^6$ Da and may comprise structures (for example linear structures) having chains of $\alpha(1\rightarrow4)$ linked D-glucose units interspersed with $\alpha(1\rightarrow6)$ glucosidic linkages. The α-glucan of the invention may comprise at least 1% of structures having chains of $\alpha(1\rightarrow4)$ linked D-glucose units interspersed with $\alpha(1\rightarrow6)$ glucosidic linkages, for example at least 10% structures having chains of $\alpha(1\rightarrow4)$ linked D-glucose units interspersed with $\alpha(1\rightarrow6)$ glucosidic linkages, for further example at least 20% structures having chains of $\alpha(1\rightarrow4)$ linked D-glucose units interspersed with $\alpha(1\rightarrow6)$ glucosidic linkages. The α-glucan of the invention may have at least 5% $\alpha(1\rightarrow6)$ glucosidic linkages. The Paenibacillus beijingensi GTFD enzyme synthesizes a high and a low molecular mass polymer from amylose V (see FIG. 20). Both polymer fractions have high degrees of branching of around 17-21%. The Paenibacillus beijingensi GTFD enzyme can synthesize polymers with long $\alpha(1\rightarrow4)$ sequences, for example maltohexaose and maltoheptaose units (see FIG. 24). Under the experimental conditions used, the high molecular mass polymer has an average molecular mass of $27\times10^6$ Da and the low molecular mass polymer has an average molecular mass of $19\times10^3$ Da. This provides the possibility of creating reuteran-like polymers of different sizes. The α-glucan of the invention may have a ratio of branching of at least 15% (for example at least 17%, for further example at least 20%) and have an average molecular mass between $22\times10^6$ Da and $35\times10^6$ Da. The α-glucan of the invention may have a ratio of branching of at least 15% (for example at least 17%, for further example at least 20%) and have an average molecular mass between $15\times10^3$ Da and $25\times10^3$ Da. The α-glucan of the invention may have more than 1 wt. % maltohexaose units. The α-glucan of the invention may have more than 1 wt. % maltoheptaose units. The α-glucan of the invention may have a ratio of branching of at least 17%, an average molecular mass between $15\times10^3$ Da and $25\times10^3$ Da, more than 1 wt. % maltohexaose units and more than 1 wt. % maltoheptaose units.

In a further aspect, the invention provides an α-glucan obtainable (for example obtained) by contacting a polysaccharide or oligosaccharide substrate comprising at its non-reducing end at least two $\alpha(1\rightarrow4)$ linked D-glucose units with an α-glucanotransferase enzyme comprising an amino acid sequence having at least 80% identity to SEQ ID NO:1, or at least 80% identity to SEQ ID NO:92.

The α-glucan of the invention can be regarded as a dietary fiber. Due to its highly branched structure, the α-glucan will resist enzymatic degradation in the upper gastrointestinal tract and end up in the large intestine where it can be fully fermented by the colonic microflora. In addition, such dietary fibres enhance satiety in humans or animals. Blood sugar levels rise after a meal. As the α-glucans of the invention display reduced digestibility compared to materials such as starch, meals prepared containing them will cause a reduced blood glucose response compared to the equivalent meal with starch, and will provoke a lower insulin response. A composition comprising the α-glucan of the invention may be for use in the control of postprandial blood glucose and insulin levels in a subject. The subject may be a human or a pet. A composition comprising the α-glucan of the invention may be for use in the treatment or prevention of a disorder linked to an increase in postprandial blood glucose and insulin levels in a subject. The disorder may be selected from the group consisting of diabetes, for example gestational diabetes; impairment of glucose metabolism; hyperinsulinemia or insulin resistance. The subject may be a diabetic or pre-diabetic human or pet.

Typically, postprandial hyper-insulinemia may promote the development of insulin resistance, metabolic syndrome, glucose intolerance and type-2 diabetes [Kopp W., Metabolism. 2003, July; 52(7):840-844]. Lowering the insulin demand after a meal however, can reduce on one hand the deterioration of the glycemic control in type-2 diabetes and on the other hand reduce the risk of developing type-2 diabetes in predisposed subjects.

A "pre-diabetic patient" is a subject showing insulin resistance or impaired glucose metabolism and is predisposed, for example by family history, lifestyle or genetics, for developing diabetes later in life. Reducing insulin secretion reduces the risk of the pancreas becoming exhausted in the long term, and so is beneficial for management of the pancreas in pre-diabetes or patients with metabolic disorders. The use of a composition comprising the α-glucan of the invention would consequently reduce the risk and/or the development of diabetes, impaired glucose metabolism, hyperinsulinemia or insulin resistance in those subjects.

Prevalence of diabetes, insulin resistance or glucose intolerance is mostly observed in adult humans. However, more and more children are affected, or predisposed or at risk of developing such a disorder later in life. Hence, advantageously, prevention and/or treatment of those disorders is started already in young age. Alternatively, and similarly as observed with humans; diabetes, hyperinsulinemia or insulin resistance are more and more widespread among animals, particularly with animals kept as pet animals. Hence, the invention also pertains to cats and dogs.

A composition comprising the α-glucan of the invention may be for non-therapeutic use to decrease plasma postprandial glucose and insulin levels. It is advantageous that a composition comprising the α-glucan of the invention can also be administered to subjects, for example healthy subjects, which may be at risk of developing diabetes type-2, insulin resistance or glucose intolerance at some later time. A composition comprising the α-glucan of the invention, as disclosed herein, provides a reduced insulin level after consumption. Many healthy people desire to lose weight. Consuming meals which contain dietary fibre can increase satiety and therefore help people consume fewer digestible calories. A composition comprising the α-glucan of the invention may be for non-therapeutic use to lose weight.

Another aspect of the invention relates to a food composition comprising the α-glucan of the invention. The food composition may for example comprise between 1 and 20 wt. % of the α-glucan of the invention. The food composition may be a beverage, for example a powdered beverage mix or a beverage creamer; a breakfast cereal; a pet food product; a baked dough product, for example a bread, a pizza or a filled savoury turnover; or a confectionery product. The confectionery product may be a frozen confectionery product such as an ice-cream; a baked confectionery product such as a biscuit, for example a filled biscuit or wafer; a chocolate confectionery product; or a sugar-style confectionery product such as a gum, a jelly, a hard-boiled sweet or a chewy sweet. The term "sugar-style confectionery product" or "sugar-style candy" refers to confectionery products which would traditionally have been based on sugar, but may be manufactured with alternative sweeteners and/or sugar substitutes.

In a further embodiment, the invention provides for the use of a GTFD α-glucanotransferase enzyme for reducing the digestible carbohydrates of a food material. The invention provides for the use of an α-glucanotransferase enzyme that comprises an amino acid sequence having at least 80% identity to SEQ ID NO:1 (for example at least 90, 95, 96, 97, 98, or 99% identity to SEQ ID NO:1), or has an amino acid sequence of SEQ ID NO:1, for reducing the digestible carbohydrates of a food material, for example a starch-containing food material. In the scope of the current invention, digestible carbohydrates correspond to the fraction of the total carbohydrates that is digestible and available to provide energy to body cells.

The invention further provides for the use of a GTFD α-glucanotransferase enzyme that comprises an amino acid sequence having at least 80% identity to SEQ ID NO:92 (for example at least 90, 95, 96, 97, 98, or 99% identity to SEQ ID NO:92), or has an amino acid sequence of SEQ ID NO:92, for reducing the digestible carbohydrates of a food material, for example a starch-containing food material.

The invention provides for the use of a GTFD α-glucanotransferase enzyme for reducing the glycemic index of a food material, for example α-glucanotransferase enzyme that comprises an amino acid sequence having at least 80% identity (for example at least 90, 95, 96, 97, 98, or 99% identity) to SEQ ID NO:1 or SEQ ID NO:92. The glycemic index is a number associated with a particular type of food that indicates the food's effect on a person's blood glucose (also called blood sugar) level. A value of 100 represents the standard, an equivalent amount of pure glucose.

Those skilled in the art will understand that they can freely combine all features of the present invention disclosed herein. In particular, features described for the method of the present invention may be combined with the product of the present invention and vice versa. Further, features described for different embodiments of the present invention may be combined. Where known equivalents exist to specific features, such equivalents are incorporated as if specifically referred to in this specification. Further advantages and features of the present invention are apparent from the figures and experimental section.

EXPERIMENTAL SECTION

Introduction

Glycoside Hydrolase (GH) family 70 originally was established for glucansucrase (GSs) enzymes (http://www-.cazy.org/), which solely are found in lactic acid bacteria (Lombard et al., 2014). GSs use sucrose to synthesize a diversity of linear and branched α-glucans, differing in the type of glycosidic linkages, the degree and type of branching, the length of the glucan chains, molecular mass, and the conformation of the polymers. Depending on the main glucosidic linkage present in their glucans products, they can be divided into dextran [α(1→6) linkages], mutan [α(1→3) linkages], reuteran [α(1→4) and α(1→6) linkages], and alternan [alternating α(1→3) and α(1→6) linkages]. Enzymes from GH70 belong to clan GH-H (also known as α-amylase superfamily), together with enzymes from families GH13 (mainly starch modifying enzymes) and GH77 (e.g. 4-α-glucanotransferases) (Stam et al., 2006). All GH-H members employ a similar catalytic mechanism, involving a covalent glucosyl intermediate and retention of the α-configuration in their products, but they vary widely in their product and reaction specificity.

To date, 60 GS enzymes have been biochemically characterized and three-dimensional structures are available for four proteins with different product specificity (Vujicic-Zagar et al., 2010; Ito et al., 2011; Brison et al., 2012; Pijning et al., 2012). These crystal structures showed that GSs are structurally similar to the closely related GH13 and GH77 starch modifying enzymes, confirming earlier secondary-structure predictions (MacGregor et al., 1996; 2001). However, GSs also possess unique structural features. Firstly, compared to GH13 and GH77 enzymes, their catalytic $(\alpha/\beta)_8$-barrel domain is circularly permuted. As a consequence, in GSs the order of the four signature sequence motifs I-IV of clan GH-H is II-III-IV-I (FIG. 1), and does not correspond to the order found in GH13 and GH77 enzymes (I-II-III-IV). Secondly, these crystal structures revealed that in GS proteins the peptide chain contains 5 domains (A, B, C, IV, and V) and that the peptide chain follows an unusual "U" fold domain structure, in which 4 of the 5 domains are built up from two discontinuous segments of the polypeptide chain (FIG. 1). The A, B, and C domains form the catalytic core and are also found in GH13 enzymes. In contrast, domains IV and V are unique to GS. The role of domain IV remains to be elucidated, whereas domain V appears to be important for polysaccharide synthesis. Indeed, truncation of domain V in the *Lactobacillus reuteri* 180 GTF180 glucansucrase enzyme yielded a catalytically fully active enzyme but with heavily impaired polysaccharide synthesis ability. This truncated protein instead produced a large amount of oligosaccharides (Meng et al., 2015).

Recently, a GH70 subfamily of enzymes inactive on sucrose, but displaying clear hydrolase/transglycosylase activity on malto-oligosaccharides (MOS) and starch has been identified, which also reflects the evolutionary relationships between families GH70 and GH13 (Kralj et al., 2011). Members of this subfamily have clear sequence similarity with GS enzymes, and are only found in lactic acid bacteria. The *Lactobacillus reuteri* 121 GTFB enzyme is the first characterized member of this subfamily cleaving α(1→4) linkages and synthesizing α(1→6) linkages, designated as a 4,6-α-glucanotransferase (4,6-α-GT) enzyme. As a result of GTFB enzyme activity, linear isomalto-/malto-polysaccharides (IMMPs) are produced which consist of linear α(1→6)-glucan chains attached to the non-reducing ends of MOS or starch fragments. IMMPs represent a new type of starch derived soluble dietary fiber according to in vitro studies, and as such they are potentially valuable food ingredients (Bai et al., 2015a; Dobruchowska et al., 2012; Dijkhuizen et al., 2010; Leemhuis et al., 2014). The exact in vivo role of GTFB-like enzymes remains unknown. It should be noted that the gtfB gene was identified upstream of the gtfA gene from *L. reuteri* 121 encoding a regular GH70 glucansucrase that converts sucrose into reuteran, a branched glucan with alternating α(1→4) and α(1→6) linkages) (Kralj et al., 2002; van Leeuwen et al., 2008a, Dobruchowska et al., 2013).

More recently a second GH70 subfamily with 4,6-α-glucanotransferase activity in non-lactic acid bacteria has been identified and the *Exiguobacterium sibiricum* 255-15 GTFC enzyme (Gangoiti et al., 2015) characterized. *Exiguobacterium* is a genus of bacilli and the data shows that biochemically this GTFC enzyme is rather similar to the *L. reuteri* GTFB enzymes. A main difference observed is that this GTFC enzyme synthesizes IsoMalto-/Malto-Oligosaccharides (IMMOs), instead of a (modified) polymer (IMMP) from malto-oligosaccharides and amylose V. Regarding their amino acid sequences, the *L. reuteri* 121 GTFB and the *E. sibiricum* GTFC share only 30% identity, but they display high conservation in their signature motifs I-IV. However, the order of these conserved motifs in GTFC enzymes is I-II-III-IV reflecting their non-permuted domain organization, similar to GH13 proteins but differing from the permuted order II-III-IV-I characteristic for glucansucrases and GTFB-like 4,6-α-glucanotransferases (FIG. 1). GTFC enzymes share the A, B and C domains with GH13 enzymes. GTFC enzymes additionally possess a domain IV inserted into domain B, however, and in several cases Ig-like2 domains that may allow cell surface binding. In view of its activity and domain organization, the *E. sibiricum* GTFC 4,6-α-glucanotransferase enzyme represents an evolutionary intermediate between GH13 α-amylases and GH70 glucansucrases/GTFB-like 4,6-α-glucanotransferases (Gangoiti et al., 2015).

This experimental section reports the biochemical characterization of a novel GH70 enzyme with unique product specificity and a different microbial origin, *Azotobacter chroococcum* NCIMB 8003. This protein was designated GTFD and resembles 4,6-α-glucanotransferases in using maltodextrins and starch as substrates. However, the *A. chroococcum* GTFD enzyme catalyzes the synthesis of a high molecular mass and relatively highly branched α-glucan with alternating α(1→4) and α(1→6) glucosidic bonds from amylose. This product does not contain consecutive α(1→6) linkages, clearly differing from the IMMPs and IMMOs synthesized by the *L. reuteri* 121 GTFB and *E. sibiricum* GTFC, respectively. The structure of the polymer formed by the *A. chroococcum* GTFD enzyme is more similar to that of the reuteran synthesized by the *L. reuteri* 121 GTFA glucansucrase from sucrose (Kraj et al., 2004; van Leeuwen et al., 2008a; Dobruchowska et al., 2013). With the discovery of this novel *Azotobacter* GTFD 4,6-α-glucanotransferase it appears that the distribution of GH70 enzymes is not limited to Gram-positive bacteria. *A. chroococcum* NCIMB 8003 is a soil-dwelling, $N_2$ fixing Gram-negative bacterium that forms thick-walled cysts. Based on the analysis of its recently elucidated genome, this bacterium was predicted to produce extracellular polysaccharides such as alginate, levan and cellulose (Robson et al., 2015). Our work suggests that *A. chroococcum* also is able to synthesize a reuteran-like α-glucan from starch/maltodextrins. The in vivo role of the polymer produced by the *A. chroococcum* GTFD 4,6-α-glucanotransferase enzyme remains to be investigated.

*A. chroococcum* GTFD showed 48% identity in amino acid sequence to a hypothetical GH70 enzyme encoded by *Paenibacillus beijingensis* DSM 24997 (Genbank accession WP_052702730.1). With the aim of further expanding the repertoire of starch-converting GH70 family enzymes, the GTFD enzyme of the plant-growth promoting rhizobacterium *Paenibacillus beijingensis* DSM 24997 was characterized. Our data shows that the *P. beijingensis* GTFD is also a reuteran-like polymer-forming 4,6-α-GTase, providing the first example of this novel reaction and product specificity in a Gram-positive bacterium. Besides, differences between the products synthesized by the action of the *A. chroococcum* GTFD and *P. beijingensis* GTFD were found, enlarging the range of reuteran-like polymers that can be synthesized from amylose. Finally, *A. chroococcum* GTFD and *P. beijingensis* GTFD isolated reuteran-like polymers, and the reaction mixtures obtained from starch incubations were subjected to in vitro digestibility studies with digestive enzymes (porcine pancreatin and rat intestinal powder extracts) in other to evaluate the potential use of these enzymes for the production of less easily digestible starchy food.

Materials and Methods

Phylogenetic Analysis

The *E. sibiricum* 255-15 sequence was retrieved from the GH70 database (http://www.cazy.org) and used as query in BLASTp searches (http://www.ncbi.nlm.nih.gov/BLAST/). Phylogenetic analysis was performed using MEGA, version 6 (Tamura et al., 2013) with a total of 71 amino acid sequences corresponding to representative GH70 and GH13 sequences identified via BLASTp. The GenBank accession numbers of the sequences used in this section are listed in Table 1. Sequences were aligned by MUSCLE, using default parameters. A phylogenetic tree was constructed by the Maximum Likelihood method based on the JTT matrix based model using in MEGA6. Partial deletion of the positions containing alignment gaps and missing data was conducted. Statistical confidence of the inferred phylogenetic relationships was assessed by performing 1,000 bootstrap replicates.

TABLE 1

Figure 2:
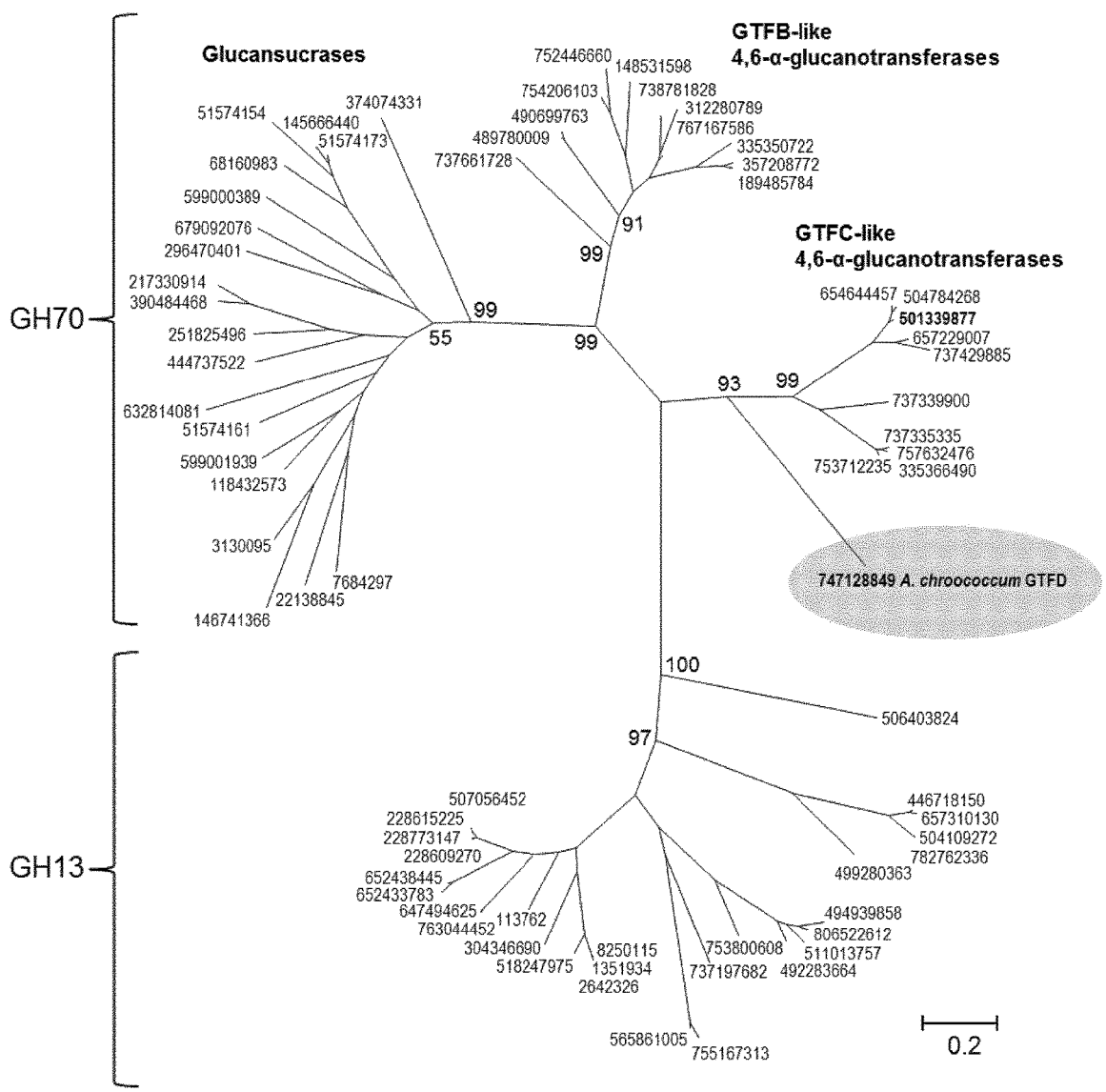
FIG. 2 is a phylogenetic tree of representative family GH70 and GH13 protein sequences identified via BLASTp searches using the *Exiguobacterium sibiricum* 255-15 GTFC 4,6-α-glucanotransferase protein as query (shown in bold). The evolutionary history was inferred by using the Maximum Likelihood method based on the JTT matrix-based model. The bar corresponds to a genetic distance of 0.2 substitutions per position (20% amino acid sequence difference). The bootstrap values adjacent to the main nodes represent the probabilities based on 1000 replicates. The protein sequences are annotated by their GenBank GI number. The names of the bacterial species are provided in Table 1. The novel *Azotobacter chroococcum* NCIMB 8003 GTFD enzyme is highlighted with a grey background.

GenBank accession numbers of the family GH70 and GH13 protein sequences used in the phylogenetic tree of FIG. 2.

| | |
|---|---|
| GTFC-like proteins | gi|501339877|dextransucrase *Exiguobacterium sibiricum* 255-15 |
| | gi|654644457|dextransucrase *Exiguobacterium undae* |
| | gi|504784268|dextransucrase *Exiguobacterium antarcticum* B7 |
| | gi|657229007|dextransucrase *Exiguobacterium acetylicum* |
| | gi|737429885|dextransucrase *Exiguobacterium* sp. RIT341 |
| | gi|737339900|dextransucrase *Bacillus kribbensis* |
| | gi|737335335|dextransucrase partial *Bacillus coagulans* |
| | gi|757632476|dextransucrase partial *Bacillus coagulans* |
| | gi|335366490|dextransucrase *Bacillus coagulans* 2-6 |
| | gi|753712235|alpha amylase catalytic domain protein *Bacillus coagulans* DSM 1 ATCC 7050 |
| GTFD proteins → GFTB-like protei | gi|747128849|dextransucrase *Azotobacter chroococcum* NCIMB 8003 |
| | gi|489780009|dextransucrase partial *Lactobacillus fermentum* ATCC 14931 |
| | gi|490699763|dextransucrase partial *Lactobacillus fermentum* 28-3-CHN |
| | gi|738781828|glycosyl hydrolase family 70 partial *Pediococcus pentosaceus* |
| | gi|767167586|glycosyl hydrolase family 70 *Lactobacillus delbrueckii* |
| | gi|312280789|dextransucrase *Lactobacillus delbrueckii* subsp. *bulgaricus* ND02 |
| | gi|357208772|putative glucansucrase *Lactobacillus reuteri* |
| | gi|737661728|hypothetical protein partial *Lactobacillus acidipiscis* |
| | gi|754206103|dextransucrase partial *Lactobacillus sanfranciscensis* |
| | gi|189485784|inactive glucansucrase *Lactobacillus reuteri* |
| | gi|752446660|hypothetical protein partial *Lactobacillus plantarum* |
| | gi|335350722|inactive glucansucrase *Lactobacillus salivarius* GJ-24 |
| | gi|148531598|dextransucrase *Lactobacillus reuteri* DSM 20016 |
| Glucansucrases | gi|51574161|glucansucrase *Lactobacillus parabuchneri* |
| | gi|118432573|dextransucrase *Oenococcus oeni* ATCC BAA-1163 |
| | gi|599001939|glucosyltransferase GTFG *Lactobacillus sucicola* DSM 21376 JCM 15457 |
| | gi|68160983|lr1943 *Lactobacillus reuteri* |
| | gi|7684297|glucosyltransferase *Streptococcus oralis* |
| | gi|146741366|glucosyltransferase *Streptococcus criceti* |
| | gi|390484468|glucansucrase *Weissella confusa* LBAE C39-2 |
| | gi|3130095|glucosyltransferase-SI *Streptococcus mutans* |
| | gi|251825496|glucansucrase *Leuconostoc lactis* |
| | gi|217330914|glucansucrase *Weissella cibaria* |
| | gi|444737522|dextransucrase *Lactobacillus curvatus* |
| | gi|145666440|dextransucrase *Lactobacillus reuteri* |
| | gi|632814081|glucosyltransferase-I *Lactobacillus kunkeei* EFB6 |
| | gi|599000389|glucosyltransferase GTFG *Lactobacillus sucicola* DSM 21376 JCM 15457 |
| | gi|51574173|glucansucrase *Lactobacillus reuteri* |
| | gi|296470401|dextransucrase *Leuconostoc citreum* |
| | gi|22138845|glucosyltransferase *Streptococcus sobrinus* |
| | gi|679092076|alternansucrase *Leuconostoc citreum* |
| | gi|51574154|glucansucrase *Lactobacillus reuteri* |
| | gi|374074331|chain A Crystal Structure Of *Leuconostoc Mesenteroides* Nrrl B-1299 N |
| GH13 proteins | gi|755167313|alpha-amylase *Streptococcus pneumoniae* |
| | gi|565861005|alpha-amylase *Streptococcus mitis* |
| | gi|494939858|alpha-amylase *Bacteroides intestinalis* DSM |
| | gi|492283664|alpha-amylase *Bacteroides fragilis* |
| | gi|806522612|alpha-amylase *Parabacteroides goldsteinii* DSM 19448 WAL 12034 |
| | gi|446718150|alpha-amylase *Escherichia fergusonii* |
| | gi|737197682|alpha-amylase *Bacillus coagulans* |
| | gi|499280363|alpha-amylase *Agrobacterium tumefaciens* |
| | gi|753800608|alpha-amylase *Odoribacter splanchnicus* |
| | gi|657310130|cytoplasmic alpha-amylase *Escherichia coli* |
| | gi|8250115|maltohexaose-forming alpha-amylase *Geobacillus stearothermophilus* |
| | gi|228609270|glucan 14-alpha-maltohexaosidase *Bacillus cereus* MM3 |
| | gi|228615225|glucan 14-alpha-maltohexaosidase *Bacillus cereus* AH621 |
| | gi|2642326|alpha amylase *Geobacillus stearothermophilus* |
| | gi|507056452|alpha-amylase *Bacillus cereus* |

TABLE 1-continued

GenBank accession numbers of the family GH70 and GH13 protein sequences used in the phylogenetic tree of FIG. 2.

gi|511013757|alpha-amylase *Bacteroides thetaiotaomicron*
gi|1351934|alpha-amylase *Geobacillus stearothermophilus*
gi|504109272|alpha-amylase *Klebsiella pneumoniae*
gi|652433783|alpha-amylase *Exiguobacterium sibiricum*
gi|228773147|glucan 14-alpha-maltohexaosidase *Bacillus thuringiensis* serovar *tochigiensis* BGSC 4Y1
gi|652438445|alpha-amylase *Exiguobacterium undae*
gi|506403824|alpha-amylase B *Halothermothrix orenii* H 18
gi|782762336|cytoplasmic alpha-amylase *Klebsiella pneumoniae*
gi|518247975|hypothetical protein *Anoxybacillus kamchatkensis*
gi|763044452|alpha-amylase *Bacillus licheniformis* S 16
gi|647494625|alpha-amylase *Bacillus licheniformis*
gi|304346690|glucan 14-alpha-maltohexaosidase *Paenibacillus curdlanolyticus* YK9
gi|113762|Maltohexaose-producing amylase *Bacillus* sp. 707

Protein Sequence Analysis

Signal peptide cleavage site was predicted using the Signal P4.1 server (http:/www.cbs.dtu.dk/services/SignalP/). Conserved domain searches were performed using the Pfam server (http://pfam.sanger.ac.uk/). Pairwise sequence comparison between the functional regions identified by the Pfam server and the *Lactobacillus reuteri* 121 GTFB and *Exiguobacterium sibiricum* 255-15 GTFC sequences were performed using Jalview (Waterhouse et al., 2009). Alternatively, multiple amino acid sequence alignments were generated with the ClustalW2 program (http://www.ebi.ac.uk/Tools/msa/clustalw2) and visualized by using Jalview (Waterhouse et al., 2009).

Cloning of the gtfD Gene from *A. chroococcum*

The DNA fragment coding for the full length GTFD protein (GenBank entry AJE22990.1, amino acids 29-780) was amplified from *A. chroococcum* NCIMB 8003 chromosomal DNA with Phusion DNA polymerase (Finnzyme) and cloned into a modified pET15b vector using ligation-independent cloning (LIC). For LIC cloning the following primer pairs with 5' extensions (in bold) were used for PCR amplification: Forward CAGGGACCCGGTGCACCGGC-CCCCACGGCGCTCG (SEQ ID NO: 2) and Reverse CGAGGAGAAGCCCGGTTACTCCTGGGCCTGGAG-GTCCGGAACCC (SEQ ID NO: 3). Basically, the KpnI-digested vector and gtfD PCR product were isolated from gel and then treated with T4 DNA polymerase (New England Biolabs) in the presence of dTTP and dATP, respectively. The two reaction products were mixed together in a 1:4 molar ratio, and the mixture was used to transform *Escherichia coli* DH5α cells (Phabagen). This resulted in a gtfD construct containing an N-terminal His6-tag cleavable by a 3C protease. The constructed expression vector pET15b/gtfD was transformed into host *E. coli* BL21 Star (DE3). The gene sequence was verified by nucleotide sequencing (LGC genomics, Berlin, Germany).

Protein Expression and Purification—*A. chroococcum*

*E. coli* BL21 Star (DE3) harboring the gtfD gene of *A. chroococcum* NCIMB 8003 was cultured in Luria Broth medium supplemented with ampicillin (100 μg ml$^{-1}$) at 37° C. and 230 rpm. When the cultures reached OD600~0.6, the inducer isopropyl-β-D-1-thiogalactopyranoside (IPTG) was added to a final concentration of 0.1 mM, and cultivation was continued for 24 h at 16° C. The cells were harvested by centrifugation (10,000 g, 20 min) and subsequently lysed with B-PER protein extraction reagent (Thermo Scientific, Pierce). After centrifugation (15,000 g, 20 min) the cell-free extracts with soluble GTFD protein were subjected to Ni-IMAC chromatography. Following washing with 20 mM Tris-HCl (pH 8.0) and 1 mM CaCl$_2$ the proteins were eluted with 200 mM imidazole in the same buffer. The GTFD containing fractions were concentrated and exchanged into 20 mM Tris-HCl buffer 1 mM CaCl$_2$ (pH 8.0) in a stirred ultrafiltration unit (Amicon, Beverly, Mass.) on a 30,000 molecular mass cut-off membrane. Purity was checked by SDS-PAGE, and protein concentrations were determined using a Nanodrop 2000 spectrophotometer (Isogen Life Science, De Meern, The Netherlands).

Cloning of the *P. beijingensis* GTFD Gene

The 2241-bp DNA fragment coding for the full-length GTFD enzyme without its putative signal peptide-encoding sequence (amino acids 31 to 776) was amplified by PCR using Phusion DNA polymerase (Finnzyme, Helsinki, Finland) and the *P. beijingensis* chromosomal DNA (DSM 24997) as the template. The PCR primers used for amplifying the GTFD gene incorporated 5' extensions (in bold) to facilitate the ligation-independent (LIC) cloning and were: PbF (5' CAGGGACCCGGTGCGGAAAGCAATGC-GAAAGG 3') (SEQ ID NO: 93) and PbR (5' CGAGGA-GAAGCCCGGTTAATTGCTAAACCGTCTTAATGCTTT-ATTC 3') (SEQ ID NO: 94). The GTFD PCR product was cloned into a modified pET15b vector by ligation-independent cloning (LIC), resulting in a GTFD construct containing an N-terminal His6-tag cleavable by a 3C protease. The constructed expression vector pET15/PbGTFD was transformed into host *E. coli* BL21 Star (DE3). The construct was confirmed by sequencing (GATC, Cologne, Germany).

Recombinant *P. beijingensis* GTFD Protein Production in *E. coli* and Purification

*Escherichia coli* BL21 Star (DE3) carrying pET15/Pb-GTFD was grown in 500-ml LB medium containing 100 μg ml$^{-1}$ ampicillin in a rotary shaker (37° C., 220 rev min$^{-1}$) to an optical density at 600 nm of 0.4-0.6. Expression of recombinant GTFD was induced by adding isopropyl-β-d-thiogalactopyranoside (IPTG) at a final concentration of 0.1 mM, and cultivation was continued at 16° C. for 20 h. Cells were harvested by centrifugation (10,000 g×20 min) and then disrupted with B-PER lysis reagent (Thermo Scientific, Pierce). After centrifugation (15,000 g×20 min), the soluble GTFD protein was purified from the cell-free extract by His-tag affinity chromatography using Ni$^{2+-}$nitrilotriacetate (Ni-NTA) as column material (Sigma-Aldrich). After washing the column with 25 mM Tris-HCl (pH 8.0), 1 mM CaCl$_2$, bound proteins were eluted with 200 mM imidazole in the same buffer and the imidazole was removed by use of a stirred ultrafiltration unit (Amicon, Beverly, Mass.) with a 30,000 molecular weight cut off. Purity and homogeneity of the purified protein was analyzed by SDS-PAGE and the amount of protein in the enzyme solutions was routinely determined with a (Nanodrop 2000 spectrophotometer (Isogen Life Science, De Meern, The Netherlands).

Enzyme Assays

The initial total activity of GTFD enzyme of *A. chroococcum* NCIMB 8003 was determined by the amylose-iodine method (Bai et al., 2015b) using 0.125% (w/v) amylose V (AVEBE, Foxhol, The Netherlands) or 0.125% (w/v) potato starch (Sigma-Aldrich) as substrates. This assay measures the decrease in absorbance of the α-glucan-iodine complex resulting from transglycosylation and/or hydrolytic activity. Enzymatic assays were performed with 28 μg/ml of enzyme in 25 mM sodium phosphate buffer (pH 6.5) at 50° C. One unit of activity corresponds to the amount of enzyme converting 1 mg of substrate per min. The optimal pH and temperature were determined over the pH range of 4.5-9.5 and a temperature range of 30-75° C., using amylose V as substrate. Sodium acetate buffer (25 mM) was used at pH 4.5-6.0, MOPS buffer (25 mM) at pH 6.0-7.0, Tris-HCl buffer (25 mM) at pH 7.0-8.0, and glycine-NaOH at pH 9.0-9.5. For thermostability studies, the enzyme (0.5 mg/ml) was incubated in the absence of substrate for 10 min at different temperatures from 50 to 95° C., and then immediately cooled to 4° C. The residual activity was measured as described above.

The initial activity of the purified *P. beijingensis* GTFD (PbGTFD) enzyme was determined using 0.125% (w v$^{-1}$) amylose V (AVEBE, Foxhol, The Netherlands) as substrate by the iodine-staining assay. This method monitors the decrease in absorbance at 660 nm in time of the α-glucan-iodine complex resulting from transglycosylation and/or hydrolytic activity. Enzymatic assays were carried out with 12 μg ml$^{-1}$ of enzyme in 25 mM sodium phosphate buffer (pH 7.0) containing 1 mM CaCal$_2$ at 50° C. One unit of activity is defined as the amount of enzyme converting 1 mg of substrate per min. The optimal pH and temperature were determined over the pH range of 4.5-10.0 and a temperature range of 35-60° C. Sodium citrate buffer (25 mM) was used for pH between 4.5 and 7.0, Sodium phosphate buffer (25 mM) for pH between 7.0 and 8.0, Tris-HCl buffer (25 mM) for pH between 8.0 and 9.0, and sodium bicarbonate buffer for pH between 8.0 and 9.0.

Substrate/Product Analysis with GTFD

Purified GTFD enzyme (40 μg ml$^{-1}$) of *A. chroococcum* NCBI 8003 was incubated separately with 25 mM sucrose (Acros), nigerose (Sigma-Aldrich), panose (Sigma-Aldrich), isomaltose (Sigma-Aldrich), isomaltotriose (Sigma-Aldrich), isomaltopentaose (Carbosynth), β-cyclodextrins (Sigma-Aldrich), malto-oligosaccharides (MOS) with different degrees of polymerization (G2 to G7), and 0.6% (w/v) amylose V (AVEBE, Foxhol, The Netherlands), potato starch (Sigma-Aldrich) and amylopectin (Sigma-Aldrich). All reactions were performed in 25 mM sodium phosphate buffer, pH 6.5 with 1 mM CaCl$_2$ at 37° C. for 24 h. The same conditions were used for the analysis of the oligosaccharides formed in time with maltohexaose and amylose V, but in this case 20 μg ml$^{-1}$ of GTFD enzyme was used. For acceptor substrate studies, GTFD (40 μg ml$^{-1}$) was incubated in 25 mM sodium phosphate buffer, pH 6.5, containing 1 mM CaCl$_2$, with the acceptor substrates maltose or isomaltose (25 mM) in the presence of 0.35% (w/v) amylose V (donor substrate). The reaction mixtures were incubated at 37° C. for 24 h. In all cases, the progress of the reactions was followed by high-performance-anion-exchange chromatography (HPAEC) and/or thin-layer chromatography (TLC).

The recombinant *P. beijingensis* GTFD enzyme (40 μg ml$^{-1}$) was incubated separately with 25 mM sucrose (Acros), nigerose (Sigma-Aldrich), panose (Sigma-Aldrich), isomaltose (Sigma-Aldrich), isomaltotriose (Sigma-Aldrich), isomaltopentaose (Carbosynth), malto-oligosaccharides (MOS) with degrees of polymerization (DP) 2-7, and 0.6% (w/v) amylose V (AVEBE, Foxhol, The Netherlands), and amylopectin (Sigma-Aldrich). All incubations were performed in 25 mM sodium phosphate buffer (pH 7.0) with 1 mM CaCl$_2$ at 37° C. for 24 h. Reactions were stopped by heating the samples to 100° C. for 8 min. The progress of the reactions was assessed by thin-layer chromatography (TLC) and/or high-performance-anion-exchange chromatography (HPAEC).

Thin Layer Chromatography and High Performance Anion Exchange Chromatography with Pulsed Amperometric Detection Analysis Samples were spotted in 1-cm lines on TLC sheets (Merck Silica Gel 60 F254, 20×20 cm), and after drying, the plates were run for 6 h in n-butanol:acetic acid:water, 2:1:1, v/v. The bands were visualized with orcinol/sulfuric acid staining and compared with a simultaneous run of a mixture of glucose and MOS (DP2 to DP7).

Product mixtures from incubations with GTFD were analyzed by HPAEC on an ICS-3000 workstation (Dionex, Amsterdam, The Netherlands), equipped with an ICS-3000 ED pulsed amperometric detection system (PAD). The oligosaccharides were separated on a CarboPac PA-1 column (Dionex; 250×4 mm) by using a linear gradient of 10-240 mM sodium acetate in 100 mM NaOH at a 1 ml/min flow rate. The identity of the peaks was assigned using commercial oligosaccharide standards.

Production and Analysis of the Products from Amylose Incubation with GTFD

Purified *A. chroococcum* and *P. beijingensis* GTFD enzymes (0.2 mg) were separately incubated with amylose V under the conditions described in "Substrate/product analysis with GTFD". After incubation for 24 h at 37° C., the reactions were stopped by transfer to 95° C. for 6 min. The HMM polymer produced by the *A. chroococcum* GTFD enzyme was isolated by size-exclusion chromatography on a Bio-Gel P-2 column (2.5×50 cm; Bio-Rad) using 10 mM NH$_4$HCO$_3$ as eluent at a flow rate of 48 ml/h. The HMM and LMM polysaccharide fractions generated by *P. beijingensis* GTFD activity on amylose by size-exclusion chromatography on a Superdex S-200 (10×300 mm; GE-Healthcare) using 25 mM ammonium bicarbonate as eluent at a flow rate of 0.5 ml min-1.

(i) Methylation Analysis

Methylation analysis of the isolated polysaccharides was performed as described before (van Leeuwen et al., 2008b) by per-methylation of the polysaccharides using CH$_3$I and solid NaOH in DMSO, followed by acid hydrolysis with TFA. Partially methylated monosaccharides were reduced with NaBD$_4$. The resulting partially methylated alditols were per-acetylated using pyridine:acetic anhydride (1:1 v/v) at 120° C. Partially-methylated alditol acetates (PMAAs) were analysed by GLC-EI-MS and GLC-FID as described (Van Leeuwen et al., 2008b).

(ii) HPSEC Analysis

The molecular mass distribution of the products mixtures were determined by HPSEC-MALS-RI as described previously (Bai et al., 2015b). Briefly, samples were dissolved at a concentration of 3.5 mg ml$^{-1}$ in DMSO-LiBr (0.05 M) and analyzed by high-performance size-exclusion chromatography coupled on-line with a multi angle laser light scattering detector (SLD 7000 PSS, Mainz), a viscometer (ETA-2010 PSS, Mainz) and a differential refractive index detector (G1362A 1260 RID Agilent Technologies). The separation was done by three PFG-SEC columns with porosities of 100, 300 and 4000 Å, coupled with a PFG guard column using DMSO-LiBr (0.05 M) as eluent at a flow rate of 0.5 ml $min^{-1}$. The system was calibrated and validated using a standard pullulan kit (PSS, Mainz, Germany) with $M_w$ ranging from 342 to 805 000 Da. The multiangle laser light scattering signal was used to determine the molecular masses of the amylose and the HMM polymers generated by the *A. chroococcum* and *P. beijingensis* GTFD enzymes with a refractive index increment value (dn/dc) of 0.072. The molecular mass of the *P. beijingensis* LMM polymer was determined by universal calibration method. WinGPC Unity software (PSS, Mainz) was used for data processing. Measurements were performed in duplicate.

(iii) NMR Spectroscopy

One-dimensional $^1H$ nuclear magnetic resonance (NMR) spectra of the product mixtures and the isolated polysaccharide were recorded in $D_2O$ on a Varian Inova 500 spectrometer (NMR Center, University of Groningen) at a probe temperature of 298K and processed with MestReNova 5.3 (Mestrelabs Research SL, Santiago de Compostella, Spain). Samples were exchanged twice in $D_2O$ (99.9 atom % D, Cambridge Isotope Laboratories, Inc., Andover, Mass.) with intermediate lyophilization, and then dissolved in 0.6 mL of $D_2O$. Chemical shifts were expressed in ppm and calibrated by internal standard acetone (δ 2.225 ppm). The percentage of different linkages was estimated by integration of the respective signal peak areas.

Enzymatic Treatment of GTFD Product

Reuteran GTFA polymer, IMMP GTFB polymer, *P. beijingensis* GTFD HMM and LMM polysaccharides and *A. chroococcum* GTFD polymer (5 mg/ml) were subjected to enzymatic digestions using excess α-amylase (*Aspergillus oryzae* α-amylase; Megazyme), dextranase (*Chaetomium erraticum*; Sigma-Aldrich), or pullulanase M1 (*Klebsiella planticola*; Megazyme). Enzymatic hydrolysis of each polymer was carried out in 50 mM sodium acetate buffer pH 5.0 for 48 h at 37° C. The degree of hydrolysis was analyzed by TLC and/or HPAEC analysis. Starch, dextran and pullulan, were used as positive controls for the α-amylase, dextranase and pullulan treatments, respectively, resulting in complete hydrolysis under these conditions.

Results and Discussion

Example 1: Identification of a Novel GH70 Protein Encoded by *Azotobacter chroococcum*

Recently the identification of a novel GH70 subfamily represented by the *Exiguobacterium sibiricum* 255-15 GTFC 4,6-α-GT (designated GTFC enzyme) has been reported (Gangoiti et al., 2015). Aiming to find new enzymes active on maltodextrins and/or starch, but displaying different product specificities, a BLASTp search was carried out using the *E. sibiricum* GTFC protein as query sequence. As described before (Gangoiti et al., 2015), this allows identification of GTFC homologs in various *Exiguobacterium* and *Bacillus* strains, sharing more than 75 and 54% of identity with the *E. sibiricum* GTFC protein, respectively (Table 2). This new BLASTp search also resulted in identification of an additional GTFC homolog (78% coverage, 39% identity with the *E. sibiricum* GTFC) present in the recently elucidated genome of *Azotobacter chroococcum* NCIMB 8003 (ATCC 4412), annotated as a dextransucrase (Robson et al., 2015). The next hits obtained using BLASTp were (putative) GTFB-like 4,6-α-glucanotransferases followed by (putative) family GH70 glucansucrases and family GH13 proteins. The evolutionary relationships among representative GH70 and GH13 family members identified by BLASTp are depicted in FIG. 2. As reported before, GTFC-like proteins cluster separately from glucansucrase- and GTFB-type of enzymes, in between family GH13 and GH70 proteins (Gangoiti et al., 2015). Phylogenetically, the hypothetical dextransucrase encoded by *A. chroococcum* is most closely related to GTFC type of enzymes. However, it only shares 39 to 42% amino acid sequence identity with the other GTFC type of enzymes, a fact reflected in its own long branch in the tree.

TABLE 2

GTFC- and GTFB-like sequences identified via a BLASTp search using the *Exiguobacterium sibiricum* 255-15 GTFC protein as query. GTFC-like sequences are indicated. *Azotobacter chroococcum* NCIMB 8003 GTFD enzyme is shown in bold.

| NCBI protein names | Organism | Coverage | Identity | Length | Accession | GTFC-like? |
|---|---|---|---|---|---|---|
| Dextransucrase | *Exiguobacterium sibiricum* 255-15 | 100% | 100% | 893 | WP_012371512.1 | Yes |
| Dextransucrase | *Exiguobacterium undae* DSM 14481 | 100% | 94% | 893 | WP_028105602.1 | Yes |
| Dextransucrase | *Exiguobacterium antarcticum* B7 | 100% | 93% | 893 | WP_014971370.1 | Yes |
| Dextransucrase | *Exiguobacterium antarcticum* DSM 14480 | 100% | 93% | 893 | WP_026830256.1 | Yes |
| Dextransucrase | *Exiguobacterium sibiricum* 7-3 | 100% | 92% | 893 | WP_026827371.1 | Yes |
| Dextransucrase | *Exiguobacterium acetylicum* DSM 20416 | 100% | 80% | 892 | WP_029342707.1 | Yes |
| Dextransucrase | *Exiguobacterium* sp. RIT341 | 100% | 75% | 892 | WP_035410561.1 | Yes |
| Dextransucrase | *Bacillus kribbensis* DSM 17871 | 98% | 56% | 904 | WP_035322188.1 | Yes |
| Dextransucrase | *Bacillus coagulans* XZL4 | 81% | 58% | 755 | WP_035317646.1 | Yes |
| Dextransucrase | *Bacillus coagulans* H-1 | 79% | 59% | 730 | WP_042872287.1 | Yes |
| Dextransucrase | *Bacillus coagulans* 2-6 | 86% | 55% | 954 | AEH52441.1 | Yes |
| alpha amylase, catalytic domain protein | *Bacillus coagulans* DSM 1 = ATCC 7050 | 86% | 54% | 965 | AJH79253.1 | Yes |
| Dextransucrase | ***Azotobacter chroococcum* NCIMB 8003 | 78% | 39% | 780 | AJE22990.1** | |
| Dextransucrase | *Lactobacillus fermentum* ATCC 14931 | 72% | 35% | 1014 | WP_003683900.1 | |
| Dextransucrase | *Lactobacillus fermentum* | 72% | 35% | 1478 | WP_046948074.1 | |
| Dextransucrase | *Lactobacillus fermentum* 28-3-CHN | 72% | 35% | 986 | WP_004563243.1 | |
| dextransucrase, partial | *Lactobacillus delbrueckii* subsp. *jakobsenii* ZN7a-9 = DSM 26046 | 71% | 34% | 966 | EOD02243.1 | |
| glycosyl hydrolase family 70 | *Pediococcus pentosaceus* IE-3 | 71% | 34% | 989 | WP_036673144.1 | |
| glycosyl hydrolase family 70 | *Lactobacillus delbrueckii* subsp. *lactis* CRL581 | 71% | 34% | 954 | WP_035171046.1 | |
| glycosyl hydrolase family 70 | *Lactobacillus delbrueckii* subsp. *delbrueckii* DSM 20074 = JCM 1012 | 71% | 34% | 922 | WP_044880492.1 | |

TABLE 2-continued

GTFC- and GTFB-like sequences identified via a BLASTp search using the *Exiguobacterium sibiricum* 255-15 GTFC protein as query. GTFC-like sequences are indicated. *Azotobacter chroococcum* NCIMB 8003 GTFD enzyme is shown in bold.

| NCBI protein names | Organism | Coverage | Identity | Length | Accession | GTFC-like? |
|---|---|---|---|---|---|---|
| cell wall binding repeat protein | *Lactobacillus delbrueckii* subsp. *bulgaricus* PB2003/044-T3-4 | 71% | 34% | 957 | WP_003613937.1 | |
| glycosyl hydrolase family 70 | *Lactobacillus delbrueckii* subsp. *lactis* DSM 20072 | 71% | 34% | 1210 | WP_035182758.1 | |
| Dextransucrase | *Lactobacillus delbrueckii* subsp. *bulgaricus* ND02 | 71% | 34% | 1294 | ADQ61508.1 | |
| putative glucansucrase | *Lactobacillus reuteri* | 78% | 30% | 1620 | AAU08003.2 | |
| hypothetical protein | *Lactobacillus reuteri* | 78% | 30% | 885 | WP_042746090.1 | |
| hypothetical protein | *Lactobacillus acidipiscis* KCTC 13900 | 70% | 35% | 908 | WP_035631372.1 | |
| putative glucansucrase | *Lactobacillus reuteri* | 78% | 29% | 1383 | ABP88725.1 | |
| Dextransucrase | *Lactobacillus sanfranciscensis* TMW 1.1304 | 64% | 34% | 866 | WP_041818260.1 | |
| inactive glucansucrase | *Lactobacillus reuteri* 121 | 80% | 29% | 1619 | AAU08014.2 | |
| hypothetical protein | *Lactobacillus plantarum* | 74% | 34% | 1136 | WP_045353679.1 | |
| hypothetical protein | *Lactobacillus plantarum* 16 | 77% | 29% | 1414 | WP_041161886.1 | |
| inactive glucansucrase | *Lactobacillus salivarius* GJ-24 | 68% | 34% | 1626 | EGM52218.1 | |
| Dextransucrase | *Lactobacillus reuteri* DSM 20016 | 75% | 30% | 1363 | ABQ83597.1 | |
| Dextransucrase | *Lactobacillus reuteri* JCM 1112 | 75% | 30% | 1488 | WP_003668618.1 | |
| Dextransucrase | *Lactobacillus reuteri* mlc3 | 75% | 29% | 1488 | WP_019251413.1 | |

This putative dextransucrase sequence of *A. chroococcum* is classified within family GH70 in the Carbohydrate-Active Enzymes (CAZy) database. Up to date, all GH70 members were encoded by members of the low GC phyla of Firmicutes, Gram-positive bacteria belonging exclusively to the orders *Lactobacillales* (GSs and GTFB-like 4,6-α-GTs) and *Bacillales* (GTFC-like 4,6-α-GTs). *A. chroococcum* NCIMB 8003 is an aerobic free-living member of the gammaproteobacteria with the capacity to form dessication-resistant cysts. This Gram-negative bacterium is considered a model microorganism in the study of nitrogen fixation and hydrogen metabolism (Robson et al., 1984; Robson 1986). *A. chroococcum* has been recognized as a producer of extracellular exopolysaccharides (Lawson & Stacey, 1954; Cote & Krull, 1988). In view of its origin and its low sequence identity with other family GH70 proteins, we decided to carry out a detailed characterization of this novel enzyme and designated it as GTFD.

*A. chroococcum* GTFD Protein Primary Sequence Analysis

The complete amino acid sequence of GTFD from *A. chroococcum* encodes a polypeptide of 780 amino acids. This protein harbors a conserved Gram-negative signal peptide with a predicted signal peptidase cleavage site between amino acids 28 and 29, consistent with an extracellular location of this enzyme. Analysis of this GTFD sequence using the Pfam server revealed that two segments of the sequence (residues 82-255 and residues 416-780) are associated with family GH70. Sequence comparisons with *E. sibiricum* GTFC and *L. reuteri* GTFB revealed that *A. chroococcum* GTFD has the (non-permuted) domain organization observed for the *E. sibiricum* GTFC-like enzymes, and differs from GTFB and glucansucrases by a circular permutation of conserved regions I-IV. Thus, from the N-terminus to the C-terminus the *A. chroococcum* GTFD polypeptide chain successively contributes to domains An, Bn, IV, Bc, Ac and C, completely lacking domain V (FIG. 1). The *A. chroococcum* GTFD lacks the Ig-like 2 domains identified in the C-terminal part of the *Exiguobacterium* GTFC homologs (Gangoiti et al., 2015). Glucansucrases and GTFB-like 4,6-α-glucanotransferases present a long variable domain of 200~700 residues at N-terminal region that has been proposed to play a role in cell wall attachment (Bath et al., 2005). This variable domain is also not present in *A. chroococcum* GTFD. However, the mature *A. chroococcum* GTFD protein (without its signal peptide) has ~50 amino acid residues of unknown function at its N-terminus that are not found in the *E. sibiricum* GTFC enzyme (FIG. 1). The four homology regions (I-IV), considered as signature motifs in both families GH13 and GH70 were identified in the *A. chroococcum* GTFD enzyme (FIG. 3). The seven residues that are fully conserved in the GH70 family (van Hijum et al., 2006; Gangoiti et al., 2015) are also present in the *A. chroococcum* GTFD. This includes the three (putative) catalytic residues Asp471, Glu505 and Asp572 (*A. chroococcum* GTFD numbering). Six of these residues also are highly conserved within GH13 enzymes with the exception of Gln208 (GTFD, *A. chroococcum* numbering), which is replaced by a His in GH13 enzymes (His140, BSTA *B. stearothermophilus* α-amylase numbering). Motifs I-IV of *A. chroococcum* GTFD are very similar to the motifs found in (putative) GTFC and GTFB 4,6-α-glucanotransferases, as revealed by the large number of amino acids conserved among these protein sequences. In previous studies, sequence alignments revealed that some residues known to be important for the activity and product specificity in glucansucrases were different in GTFB- and GTFC-like 4,6-α-glucanotransferases (Leemhuis et al., 2013; Gangoiti et al., 2015). Most notable are the replacement of the conserved residue W1065 in glucansucrases by a Tyr residue in the 4,6-α-glucanotransferases, and the differences in conserved region IV at positions 1137, 1140 and 1141 (GTF180 *L. reuteri* 180 numbering). In the *A. chroococcum* GTFD the conserved residue W1065 is replaced by a Tyr residue, and the amino acid residues at positions 1137 and 1141 are Gln and Asn, respectively, similar to other 4,6-α-glucanotransferases. In contrast, the conserved C11140 is replaced by a His residue in *A. chroococcum* GTFD, instead of the Lys residue present in most 4,6-α-glucanotransferases. Previous mutational studies in GTF180 glucansucrase demonstrated that residue Q1140 influences the glycosidic linkage reaction specificity (van Leeuwen et al., 2009). Besides, residue Q1140 together with residues N1411 and D1458, "block" the active site beyond subsite-1, preventing the binding of longer oligosaccharides. Due to this feature glucansucrases only transfer a single glucose moiety per reaction cycle, but not oligosaccharides (Vujicic-Zagar et al., 2010). On the other hand, the sequence order of conserved regions in *A. chroococcum* GTFD is I-II-III-IV reflecting its non-permuted domain organization, similar to the *E. sibiricum* GTFC 4,6-α-glucanotransferase and differing from the permuted order II-III-IV-I characteristic for glucansucrases and GTFB homologues (FIG. 1). *A. chroococcum* GTFD thus appears to be a novel GH13-GH70 evolutionary intermediate with a domain architecture resembling GH13 enzymes, but displaying a new enzymatic reaction specificity (see below).

Purification and Biochemical Properties of the *A. chroococcum* GTFD

The gene encoding *A. chroococcum* GTFD enzyme without the putative signal sequence was cloned in-frame with an N-terminal His-tag and expressed in *E. coli* (DE3) BL21 star. Most of the GTFD protein was produced in soluble form and could be purified to homogeneity by metal-chelate chromatography (FIG. 4). SDS-PAGE analysis of purified enzyme revealed a single protein band with an apparent molecular weight of ~90 kDa which fits the theoretical value deduced from the sequence (86.4 kDa).

The effects of pH and temperature on *A. chroococcum* GTFD activity were determined using amylose V as substrate. The enzyme showed its maximum activity at 60° C. and at pH 6.5 and retained more than 70% of this activity over a pH range from 5.5 to 7.0 (FIG. 5AB). Besides, the enzyme was stable up to 60° C. for at least 10 min in 20 mM Tris-HCl buffer pH 8.0 containing 1 mM $CaCl_2$ (FIG. 5C). Its thermostability was higher than that of the *L. reuteri* 121 α-4,6-GT GTFB and GS GTFA, which are stable at temperatures up to 45° C. and 50° C., respectively (Kralj et al., 2004; Bai et al., 2015b). The specific total activity values of GTFD on 0.125% (w/v) amylose and starch in sodium phosphate buffer, pH 6.5 containing 1 mM $CaCl_2$ and at 50° C. were 6.6±0.05 and 6.0±0.2 U/mg of protein, respectively. These values are significantly higher than the ones reported before for *L. reuteri* 121 GTFB (2.8 U/mg) and *E. sibiricum* 255-15 GTFC (2.2 U/mg) using amylose V as substrate (at their optimal conditions) (Bai et al., 2015b; Gangoiti et al., 2015).

Substrate and Product Specificity of the *Azotobacter chroococcum* GTFD

The substrate specificity of GTFD was studied by incubating the enzyme with different oligosaccharides and polysaccharides at 37° C. for 24 h. The enzyme was inactive on sucrose, panose, nigerose, β-cyclodextrins, and isomalto-oligosaccharides with DP2, DP3, and DP5. However, GTFD showed clear hydrolase/transglycosylase activity with malto-oligosaccharides (MOS) of DP3 to DP7 and formed a range of shorter and longer oligosaccharides (FIG. 6). Also polymer accumulation was detected in the case of G4 (a polymer of four glucose monomers) and larger MOS. However, GTFD was unable to use maltose as glucose donor substrate. When exploring the activity of GTFD enzyme with amylose V, potato starch, and amylopectin, some lower molecular mass products appeared on the TLC, reflecting its hydrolase/disproportionating activity on these polymers. Especially maltose accumulated from the various substrates (FIG. 6).

$^1$H NMR analysis of the product mixture obtained with GTFD using amylose V and starch as substrates showed two broad signals in the anomeric region (δ=~5.40-5.35 and ~4.97) corresponding to the α(1→4) and the newly synthesized α(1→6) linkages (FIG. 7). The spectra also revealed the presence of signals corresponding to free glucose units (Gα H-1, δ 5.225; Gβ H-1, δ 4.637) and 4-substituted reducing-end glucose residues (Rα H-1, δ 5.225; Rβ H-1, δ 4.652). The molar ratio of the α(1→4) linked, α(1→6)-linked and reducing glucose residues for amylose and starch reaction products were 70:28:2 and 80:18:2, respectively. Comparison of these $^1$H NMR spectra with those of the IMMPs generated by GTFB (Leemhuis et al., 2014) from amylose revealed the presence of extra signals strongly overlapping in the α(1→4) anomeric region in the case of the GTFD reaction mixtures. The different built-up of this broad signal at δ~5.40-5.35, indicated that a different product was formed.

The molecular mass distribution of the products generated by GTFD from amylose V was determined by HPSEC-MALS-RI analysis (FIG. 8). The starting amylose V substrate eluted as a single peak at 22 ml, with an average $M_w$ of 174×10$^3$ Da. After incubation of the amylose V with the GTFD enzyme the peak corresponding to the amylose V substrate disappeared and two other main peaks were generated, at 19 and 33 ml. The peak eluting at 19 ml corresponded to a high molecular mass polymer with an average $M_w$ of 13×10$^6$ Da, whereas the second peak eluting at 33 ml corresponded to maltose and other low molecular mass oligosaccharides. The elution profile of the products synthesized by GTFD from amylose V was different to the one obtained after incubating this substrate with the *L. reuteri* 121 GTFB 4,6-α-glucanotransferase. In the case of GTFB, the peak corresponding to the IMMPs (27.6 ml) eluted at a higher elution volume than the one corresponding to the starting amylose V substrate (22 ml), and had an average $M_w$ of 15×10$^3$ Da. These data revealed that GTFD produced a high molecular mass polymer with a $M_w$ value about 80 times greater than that of the starting amylose V substrate. This polymer is also much larger than the IMMPs and the IMMOs generated by the *L. reuteri* 121 GTFB and the *E. sibiricum* GTFC (Gangoiti et al., 2015), respectively, from amylose.

Characterization of the Polymer Synthesized by the *A. chroococcum* GTFD from Amylose V For further analysis the amylose V derived high molecular mass polymer was isolated by size-exclusion chromatography on Biogel P-2 column by collecting the void-volume fraction. 1D $^1$H NMR analysis of this polymer revealed that 68 and 32% of the glucosyl units are forming α(1→4) and α(1→6) linkages, respectively, indicating a slight increase in the percentage of α(1→6) linked glucose residues over those in the reaction mixture. The $^1$H NMR spectrum of this GTFD polymer (FIG. 9) showed high similarity to that of the reuteran synthesized by *L. reuteri* 121 and *L. reuteri* 35-5 GTFA GSs from sucrose (Kralj et al., 2002; van Leeuwen et al., 2008a). In the 1D $^1$H NMR spectrum the structural-reporter-group signal a for 6-substituted Glc residues shows a lower relative intensity for the GTFD product than for the GTFA product. Peak b, indicative for terminal residues, has a higher relative intensity. In the 2D $^1$H-$^1$H TOCSY spectrum the cross-peak with a is only observed in the α(1→4) anomeric track, indicating that 6-substituted Glc residues only occur in a →6)-α-D-Glcp-(1→4)-sequence. There is no evidence for two or more consecutive α(1→6)-linked Glc residues. Moreover, signals d and e in the 2D $^{13}$C-$^1$H HSQC spectrum, corresponding with H-6a and H-6b of 6-substituted residues, have $^1$H chemical shift values of δ 3.97 and 3.78, respectively. In the α(1→6)-anomeric track of the 2D $^1$H-$^1$H TOCSY spectrum no cross peaks at these values are observed. Peak c in the 2D $^{13}$C-$^1$H HQSC spectrum is indicative for 4-substituted residues (Van Leeuwen et al. 2008a). The resemblance of both α-glucans was confirmed by methylation analysis (Table 3). Methylation analysis of the GTFD high molecular mass product revealed the presence of terminal, 4-substituted, 6-substituted, and 4,6-disubstituted glucopyranose residues in molar percentages of 19, 45, 18 and 18%. This shows a higher ratio of branching than the GTFA reuteran product, i.e. 18% rather than 11%, which fits with the observations in the 1D $^1$H NMR spectrum (FIG. 9) (van Leeuwen et al., 2008a). As above, the average molecular mass of the polysaccharide produced by *A. chroococcum* GTFD was determined to be 13×10$^6$ Da, whereas that of the reuteran produced by GTFA GS from sucrose was 45×10$^6$ Da (Kralj et al., 2005). Thus, the high molecular mass product of GTFD showed a higher amount of branches, a lower amount of alternating α(1→4) and α(1→6) linkages, and a decreased molecular mass compared to the reuteran synthesized by GTFA from sucrose.

TABLE 3

Structural analysis of the polymer produced by *Azotobacter chroococcum* NCIMB 8003 GTFD enzyme from amylose V.

| Parameter | Type of glucosyl units | *A. chroococcum* GTFD polymer | *L. reuteri* 121 GTFA reuteran$^c$ |
|---|---|---|---|
| Methylation analysis(%) | Glcp(1→ | 19 | 7 |
|  | →4)-Glcp-(1→ | 45 | 47 |
|  | →6)-Glcp-(1→ | 18 | 35 |
|  | →4,6)-Glcp-(1→ | 18 | 11 |
| NMR chemical shift (%)$^a$ | α(1→4) | 68 | 43 |
|  | α(1→6) | 32 | 57 |
| Molecular mass (10$^6$ Da)$^b$ |  | 13 | 45 |

$^a$The data represent the ratios of integration of the surface areas of the α(1→6) linkage signal at 4.97 ppm and the α(1→4) linkage signal at 5.36 ppm in the $^1$H NMR spectra of the polysaccharides (see FIG. 4).
$^b$The average molecular mass of polysaccharide was determined in duplicate.
$^c$Taken from Kralj et al., 2005.

Oligosaccharides Formed in Time from Maltohexaose and Amylose V by the *A. chroococcum* GTFD Enzyme In order to get information about the formation of products in the progress of time, both maltohexaose and amylose V were incubated with GTFD, and samples for HPAEC analysis were taken at different time points (FIG. 10). From maltohexaose, GTFD produces in addition to G2, an oligosaccharide of unknown structure with a high DP (peak eluting at around 40 min) as the first main reaction products (FIG. 10A). The excess of G2, compared to G4 suggests that GTFD catalyses a maltotetraosyl-transfer reaction yielding the peak of unknown structure. The simultaneous analysis of a mixture of MOS of DPs from 2 to 30, showed that the retention time of this peak did not match exactly with that of maltodecaose, which eluted slightly later, indicating a structure with DP10 and at least one α(1→6) linkage. Later in time, MOS of lower DPs than that of the starting donor, but also small peaks corresponding to oligosaccharides of higher DPs, are detected as a result of the GTFD main disproportionating activity. The unknown product initially formed decreased in the late stage of the reaction indicating that GTFD can use this oligosaccharide as donor and/or acceptor substrate. From amylose V, GTFD releases G2, G3, G4, G5 and G6 after 10 min of reaction as side products of its hydrolase/transglycosidase activity (FIG. 10B). Most notably, glucose is not detected at the beginning of the reaction when both maltohexaose and amylose are used as substrates. Overall, these data suggest that the *A. chroococcum* GTFD enzyme presents more than one donor substrate binding subsite, similar to other amylolytic enzymes, such as amylases, cyclodextrin glycosyl transferases and amylomaltases, (MacGregor et al., 2001; Uitdehaag et al., 2000; Naessens et al., 2005). Thus, this GTFD does not preferentially transfer glucosyl units one by one, but MOS of low DP instead. The *E. sibiricum* GTFC also showed an additional endo-α(1→4)-glycosidase activity, combined with the main α(1→6) transfer activity of single glucosyl units to form IMMOs (Gangoiti et al., 2015). In accordance with this mechanism of polymerization, the *A. chroococcum* GTFD produces an α-glucan with a α(1→6)/α(1→4) alternating structure and α(1→6) branching points.

*A. chroococcum* GTFD Acceptor Substrate Reaction Studies

To gain a better understanding of the mode of action of the *A. chroococcum* GTFD, the acceptor substrate specificity of this enzyme was studied and compared to that of *L. reuteri* GTFB (FIG. 11AB). When amylose V was incubated with GTFD and maltose as acceptor substrate, larger amounts of maltotriose and maltotetraose were detected than in the incubation with amylose V alone. A small amount of panose was also identified by HPAEC, probably formed by coupling of glucose with an α(1→6) linkage to the non-reducing end of maltose (minor activity). In case of GTFB, among other oligosaccharides with higher DPs, peaks at the positions of panose and maltotriose were detected.

These results indicate that GTFD and GTFB have the ability to synthesize α(1→4) linkages and α(1→6) linkages when an acceptor substrate of low DP such as maltose is present. Isomaltose was a poor acceptor substrate for GTFD. HPAEC analysis showed that in the presence of isomaltose, GTFD does not form large amounts of oligosaccharides, and only small amounts of maltose and an unknown product were identified (FIG. 11A). In contrast, GTFB efficiently uses isomaltose as acceptor substrate yielding large amounts of oligosaccharides, corresponding to a isomaltose extended with a series of glucose units (isomaltotriose, isomaltotetraose and isomaltopentaose) (FIG. 11B). This result is in agreement with the presence of consecutive α(1→6) linkages in the GTFB products, and their absence in GTFD products.

Enzymatic Hydrolysis of the *A. chroococcum* GTFD Polymer

To further explore the nature of the *A. chroococcum* GTFD polymer and to compare it with the polymers synthesized by *L. reuteri* 121 GTFA GS (reuteran) and GTFB 4,6-α-GT (IMMP), these 3 α-glucans were treated with a high-dose of α-amylase, dextranase and pullulanase enzymes (FIG. 12). Subsequent TLC analysis revealed that the GTFD polymer, reuteran and IMMP were resistant to the endo-α(1→4)-hydrolase action of α-amylase, whereas starch was completely hydrolysed. Only trace amounts of maltose were detected by TLC in the case of the GTFD polymer and reuteran digestion (FIG. 12A). The GTFD polymer and reuteran were resistant to endo-α(1→6)-hydrolase activity of dextranase, again confirming the absence of consecutive α(1→6) linkages in both polymers. IMMP and dextran, however, were completely degraded by the action of dextranase (FIG. 12B). In the case of pullulanase that cleaves the alternating α(1→6) linkages in pullulan and branched polysaccharides, pullulan was included as a positive control. IMMP was resistant to pullulanase treatment reflecting the presence of consecutive α(1→6) glycosidic bonds only in its structure. In contrast, pullulanase efficiently hydrolysed reuteran and the GTFD polymer, which is in agreement with the presence of alternating α(1→6)/α(1→4), and α(1→4,6) branching points in these polymers (FIG. 12C). It can therefore be seen that the polymer synthesized by *L. reuteri* 121 GTFB 4,6-α-GT (IMMP), described in EP2248907, contains consecutive α(1→6) glycosidic bonds and does not contain alternating α(1→6)

linkages. HPAEC analysis enabled the identification of the reaction products formed from GTFD polymer after pullulanase digestion, and clearly demonstrated that the GTFD polymer is built-up from maltose, maltotriose, and maltotetraose elements linked by α(1→6) linkages (FIG. 13). The same oligosaccharides were obtained by pullulanase M1 hydrolysis of reuteran (van Leeuwen et al., 2008a). However, in case of the GTFD polymer a small additional peak corresponding to maltopentaose was also detected. Combining all data from NMR spectroscopy and methylation analysis and pullulanase digestion, composite structures were formulated (FIG. 14), containing all structural elements observed for the GTFD product in comparison with the GTFA product (Van Leeuwen et al. 2008a). The most notable differences between the GTFA and GTFD products are the higher amount of branching for the GTFD product and the lower amount of α(1→6)-linkages. This results in a composite structure containing less alternating α (1→4)/α (1→6) sequences, and more linear α(1→4) sequences. As indicated in FIG. 14, the *A. chroococcum* GTFD product comprises structures having chains of α(1→4) linked D-glucose units interspersed with α(1→6) glucosidic linkages.

Example 2: In Vitro Digestibility of Gelatinized Wheat Starch Treated with *A. chroococcum* GTFD Generation of the *A. chroococcum* GTFD α-glucan from wheat starch A 0.6% suspension was prepared with wheat starch (Sigma S5127) in water. The suspension was heated to 90° C. for 10 min to gelatinize the starch and subsequently cooled to 37° C. Three hundred and thirty three μL of 50 mM $CaCl_2$ solution were added to the gelatinized starch suspension followed by 283 μL of *A. chroococcum* GTFD (AcGTFD) enzyme solution (667 μg of enzyme/100 mg starch). Starch suspension was incubated for 24 h at 37° C. After incubation, the treated suspension was heated at 95° C. for 6 min to inactivate the AcGTFD enzyme. Finally, the treated starch suspension was freeze-dried to obtain a powder of the AcGTFD generated material.

Preparation of Digestive Enzymes for Assay

Pancreatin from porcine pancreas (Sigma P7545) and intestinal acetone powders from rat (Sigma 11630) were extracted in 10 mM PBS solution (pH 6.8) at a 40 mg enzyme powders per mL concentration. Enzyme suspensions were vortex-mixed and sonicated in iced water for 7 min. Sonicated suspensions were then centrifuged at 10,000×g for 30 min at 4° C. Supernatants were collected and protein content as well as enzyme activities were measured.

Protein Content Measurements in Digestive Enzyme Preparations

Protein was quantified in the supernatants obtained from the enzyme extractions with the BCA (Bicinchoninic Acid) kit for protein determination (Sigma BCA1-1KT). Supernatants were diluted 10 times and protein contents were measured after reacting with BCA reagent for 30 min at 37° C. in a spectrophotometer at 562 nm wavelength. A standard curve was prepared with bovine serum albumin standards for the calculation of total protein content.

Measurements of Activity of Digestive Enzymes

A 1% solution of soluble starch from potato (Sigma S2004) was prepared in 10 mM PBS solution (pH 6.8). One hundred microliters of 1% soluble starch solution were added to 100 μl of pancreatin supernatant or rat intestinal acetone powders supernatant. Starch and enzyme mixtures were incubated at 37° C. for 10 min with constant stirring.

Mixtures were subsequently boiled for 10 min to stop the enzymatic reaction. After allowing the mixtures to cool down, sample tubes were centrifuged at 10,000×g for 10 min and glucose was measured via a colorimetric assay with the use of the Autokit Glucose (439-90901, Wako Diagnostics). One unit of enzyme activity was defined as the amount of protein required to hydrolyze 1 μg of glucose from soluble starch.

In Vitro Digestibility Measurements

A 1% solution of the AcGTFD generated material was prepared in 10 mM PBS (pH 6.8). A 300 μl aliquot of the solution was pre-heated to 37° C., along with the enzyme solutions, for 5 min. One hundred units/mg of the AcGTFD product of each digestive enzyme were added to the sample, standard and blank tube, in triplicate. Sample tubes were vortex-mixed and incubated for 20, 60, and 120 min at 37° C. with constant stirring. After each time point, a 0.5 mL aliquot of sample was transferred into a tube containing 1.5 mL of 90% aqueous ethanol. Sample aliquots in ethanol were stored at 4° C. until ready for glucose quantification. Sample aliquots were centrifuged at 10,000×g for 10 min and glucose was measured via a colorimetric assay with the use of the Autokit Glucose (439-90901, Wako Diagnostics).

1. Results

Treatment of gelatinized wheat starch with AcGTFD resulted in a material with a significantly lower rate and extent of in vitro digestibility. As can be observed from FIG. 27, AcGTFD treatment (B) reduced the total digestibility of the gelatinized wheat starch by 30% after 120 min of incubation with porcine pancreatin and rat intestinal powders. Moreover, the content of rapidly digestible starch, represented by the % hydrolyzed sample after 20 min of incubation, was significantly reduced by the AcGTFD treatment.

Example 3: Identification of a Novel GH70 Protein Encoded by *Paenibacillus beijingensis*

A protein homologous to the *A. chroococcum* GTFD was identified in the genome of *Paenibacillus beijingensis* DSM 24997 by BLASTp searches within the NCBI and IMG-ER platforms. *A. chroococcum* GTFD showed 48% identity in amino acid sequence to a hypothetical GH70 enzyme encoded by *Paenibacillus beijingensis* DSM 24997 (Genbank accession WP_052702730.1).

Primary Sequence Analysis of the *P. beijingensis* GTFD Enzyme

The identified *P. beijingensis* GTFD protein sequence consists of 776 amino acids and contains a putative secretion signal peptidase cleavage site between amino acids 30 and 31, in accordance with the extracellular location of GH70 enzymes. The domain organization of the *P. beijingensis* GTFD resembles that of *E. sibiricum* GTFC and *A. chroococcum* GTFD enzymes, regarded as structurally evolutionary intermediates between GH13 and GH70 families (FIG. 2). Consequently, this enzyme displays a GH13-like domain arrangement with a non-permuted catalytic $(β/α)_8$ barrel, but possess an extra domain IV inserted in domain B. Similar to *E. sibiricum* GTFC and *A. chroococcum* GTFD, this enzyme lacks the variable N-terminal domain and the domain V typically found in GH70 GSs and GTFB homologues. Also, the Ig2-like domains identified in the C-terminal part of some GTFC-like proteins, appeared to be absent from *P. beijingensis* GTFD, as observed in the case of the *A. chroococcum* GTFD.

On the basis of sequence alignments the four conserved regions of clan GH-H were identified in *P. beijingensis*

GTFD and compared with those corresponding to other GH70 proteins. In accordance with its non-permuted domain organization, the order of these four conserved regions in *P. beijingensis* GTFD and *A. chroococcum* GTFD is I-II-III-IV, instead of the permuted order II-III-IV-I characteristic of GH70 glucansucrases and GTFB-like 4,6-α-GTases. The seven amino acid residues that are fully conserved in motifs I to IV of all GH70 family members are also found in both GTFD-like proteins (FIG. 15). Among these seven residues, the nucleophile, the general acid/base and the transition state stabilizer of the catalytic triad were identified as Asp409, Glu442 and Asp512 in *P. beijingensis* GTFD respectively (using *P. beijingensis* GTFD numbering).

Purification and Biochemical Properties of the *P. beijingensis* GTFD Enzyme

Recombinant *P. beijingensis* GTFD without its peptide signal sequence (amino acids 31-776) was expressed in soluble form at high levels and purified to homogeneity from *E. coli* BL21 star (DE3) by His-tag affinity chromatography yielding 50 mg of pure protein per liter of culture. SDS-PAGE analysis of the pure enzyme revealed the appearance of a single ~80-kDa protein band (FIG. 16), consistent with the predicted molecular mass deduced from its amino acid sequence (85 kDa). The effects of pH and temperature on the enzyme activity were determined by the amylose-iodine assay (FIG. 17). The GTFD enzyme of *P. beijingensis* displayed its maximum activity at pH 7.0 and 50° C. A higher optimum temperature value was reported for the *A. chroococcum* GTFD enzyme (65° C.), whereas no significant differences in the optimal pH value existed between both GTFD enzymes. In contrast, the GTFB 4,6-α-GTases characterized from *Lactobacillus* strains have been reported to show significantly more acidic optimum pH values of 4.5 and 5 reflecting their adaptation to the gastrointestinal tract. The specific total activity value of the *P. beijingensis* GTFD in 25 mM sodium phosphate buffer, pH 7.0, containing 1 mM $CaCl_2$, and at 50° C. was 6.3±0.17 U me, and is similar to that of *A. chroococcum* GTFD (at pH 6.5 and 50° C.), namely 6.6±0.05 U me. Thus, both GTFD enzymes exhibited remarkably higher total specific values than those determined for the *L. reuteri* GTFB and the *E. sibiricum* GTFC 4,6-α-GTase, whose specific activity values were 2.8 U $mg^{-1}$ and 2.2 U $mg^{-1}$, respectively (at 40 and pH 5 and 6, respectively) [J. Gangoiti, T. Pijning, L. Dijkhuizen (2015)].

Substrate and Product Specificity

The substrate specificity of the *P. beijingensis* GTFD (FIG. 18) was studied by incubating the enzyme with different carbohydrate substrates at 37° C. for 24 h, and compared with that of the *A. chroococcum* GTFD enzyme (FIG. 6). The *P. beijingensis* GTFD enzyme was inactive on sucrose, panose, nigerose, and isomalto-oligosaccharides with DP2, DP3, and DP5 (Data not shown), similar to the *A. chroococcum* GTFD and other 4,6-α-GTases. Instead, the *P. beijingensis* GTFD enzyme catalyzed the conversion of malto-oligosaccharides (MOS) of DP 3 to 7 showing both hydrolysis and transglycosylase (disproportionation) activity (FIG. 18). Indeed, incubation of *P. beijingensis* GTFD with MOS of DP 3 to 7 revealed the formation of lower- and higher-molecular-mass products. Besides, with G4 and larger MOS as substrates, polymeric material was also clearly detected remaining at the origin of the TLC plates. However, the *P. beijingensis* GTFD failed to act on maltose. Similar substrate specificity was observed with *A. chroococcum* GTFD (FIG. 6). The main difference between both GTFD enzymes was observed when amylose V and amylopectin were used as substrates. As reported before, the *A. chroococcum* GTFD enzyme accumulated G2 and some low molecular mass oligosaccharides from these polymer substrates, reflecting its hydrolase/disproportionating activity. In contrast, these low molecular mass products were not clearly detectable by TLC when exploring the activity of *P. beijingensis* GTFD on amylose and amylopectin.

$^1$HNMR analysis of the product mixture generated from amylose V revealed the presence of two broad anomeric signals corresponding to the α(1→4) (δ 5.40-5.35) and the newly formed α(1→6) linkages (δ~4.97) (FIG. 19). This $^1$H NMR spectrum resembled that of the products derived from amylose V by *A. chroococcum* GTFD treatment (FIG. 7A) suggesting that both GTFD enzymes have the same product specificity. The spectra also showed the presence of small signals corresponding to free glucose units (Gα H-1, δ 5.225; Gβ H-1, δ 4.637) and 4-substituted reducing end glucose residues (Rα H-1, δ 5.225; Rβ H-1, δ 4.652). These signals were much smaller in the case of the *P. beijingensis* GTFD product mixture reflecting that only trace amounts of glucose, maltose and other small oligosaccharides are present in this product, as previously observed by TLC analysis. The molar ratio of the α(1→4)-linked, α(1→6)-linked and reducing glucose residues for both reactions were nearly identical, and were 72:26:2 for the *A. chroococcum* GTFD and 75:25:<1, for the *P. beijingensis* GTFD. Methylation analysis of the product mixture synthesized by the *P. beijingensis* GTFD from amylose V revealed the presence of terminal, 4-substituted, 6-substituted, and 4,6-disubstituted glucopyranose residues in a molar percentage of 18, 54, 8 and 20%, in accordance with the linkage ratios determined by $^1$HNMR. This result confirmed that the *P. beijingensis* GTFD acts as a 4,6-α-glucanotransferase cleaving α(1→4) linkages and synthesising a branched α-glucan consisting of α(1→4) and α(1→6) linkages.

Comparison of the products generated from amylose by the *P. beijingensis* and *A. chroococcum* GTFD enzymes by HPSEC with multi detection, revealed differences in their molecular mass distribution (FIG. 20). After incubating amylose V with the *A. chroococcum* GTFD, the single peak corresponding to amylose with a small molecular mass (approximately 200×$10^3$ Da) disappeared and two new peaks were formed: A peak eluting at ~19 ml corresponding to a high molecular mass (HMM) polymer with an average $M_w$ of 13×$10^6$, and a second peak eluting at ~34 ml corresponding to maltose and other small oligosaccharides. By contrast, the HPSEC profile of products synthesized by *P. beijingensis* GTFD from amylose V revealed the presence of two main polymer populations, whereas maltose and other small oligosaccharides were not significantly accumulated. Besides an early peak eluting at ~19 ml and corresponding to a HMM polymer with a $M_w$ of 27×$10^6$ Da, a second broad peak eluting at ~29 ml and corresponding to a low molecular mass (LMM) polymer with a $M_w$ 19×$10^3$ Da was detected. The synthesis of HMM and LMM products may be the result of two distinct processive and non-processive elongation mechanisms in *P. beijingensis* GTFD. Based on the refractive index response, the *P. beijingensis* GTFD HMM polymer represented only a small percentage (less than 20%) of the total product, the LMM mass polymer being the main product of the reaction.

Characterization of the High- and Low-Molecular Mass Polymers Produced by the *P. beijingensis* GTFD Enzyme from Amylose V For a more detailed characterization the HMM and LMM polymers generated from amylose V by the *P. beijingensis* GTFD were isolated by size-exclusion chromatography analysis on Sephadex S-200 and subjected to 1D/2D (1)H/(13)C NMR spectroscopy. FIG. 21 presents the very similar $^1$H NMR spectra obtained for both polysaccharides, showing a linkage ratio α(1→4):α(1→6)=70:30 for the HMM polymer and a linkage ratio α(1→4):α(1→6)=76:23 for the LMM polymer, indicating a slight increase in the percentage of α(1→6)-linked glucose residues in the HMM polymer. 2D NMR data of the *P. beijingensis* GTFD α-glucans match those of the reuteran type of polymers generated by *A. chroococcum* GTFD and *L. reuteri* 121 GTFA glucansucrase from amylose and sucrose, respectively (FIG. 22). Most notably, the typical chemical shift values corresponding to successive α(1→6) linkages were not identified in the 2D NMR spectra of *P. beijingensis* GTFD HMM (FIG. 22) and LMM (not shown) products. The reuteran-like structure of the *P. beijingensis* GTFD products was further confirmed by methylation analysis, revealing the presence of terminal, 4-substituted, 6-substituted and 4,6-disubstituted glucopyranosyl units (Table 4). The HMM *P. beijingensis* GTFD product contains approximately similar amounts of α(1→6) linkages than the reuteran-like polymer synthesized by *A. chroococcum* GTFD (Table 3), but slightly differs in the amount of 6-substituted and 4,6-disubstituted glucopyranosyl residues. This results in a reuteran-like polymer with a slightly lower amount of alternating α(1→4)/α(1→6) glycosidic linkages (i.e. 14% rather than 18%) and a higher amount of branches (21% rather than 18%). Compared to the HMM *P. beijingensis* product, the LMM *P. beijingensis* GTFD product presents lower amounts of α(1→6) linkages in linear orientation reflected by the reduced amount of 6-substituted glucopyranosyl units (8% rather than 14%).

TABLE 4

Structural characterization of the HMM and LMM polymers synthesized by the *P. beijingensis* GTFD enzyme from amylose V.

| Parameter | Type of glucosyl units | *P. beijingensis* GTFD HMM polymer | *P. beijingensis* GTFD LMM polymer |
|---|---|---|---|
| Methylation analysis (%) | Glcp(1→ | 20 | 17 |
| | →4)-Glcp-(1→ | 45 | 54 |
| | →6)-Glcp-(1→ | 14 | 8 |
| | →4,6)-Glcp-(1→ | 21 | 21 |
| NMR chemical shift (%)[a] | α(1→4) | 70 | 76 |
| | α(1→6) | 30 | 23 |
| Molecular mass (10$^3$ Da)[b] | | 27 10$^3$ | 19 |

[a]The data represent the ratios of integration of the surface areas of the α(1→6) linkage signal at 4.97 ppm and the α(1→4) linkage signal at 5.36 ppm in the $^1$H NMR spectra of the polysaccharides (see FIG. 4).
[b]The average molecular mass of polysaccharide was determined in duplicate.

To gain more insight into the carbohydrate structures of the HMM and LMM *P. beijingensis* GTFD products, and to compare them with the *A. chroococcum* GTFD reuteran-like polymer and *L. reuteri* 121 GTFB IMMP, these α-glucans were incubated for 48 h with different hydrolytic enzymes: α-amylase, dextranase and pullulanase M1 (FIG. 23). Examination of the hydrolysis products showed that HMM *P. beijingensis* GTFD and *A. chroococcum* GTFD polymers were partly resistant to the endo-α-1,4-hydrolase activity of the α-amylase. In both cases, only trace amounts of HMM oligosaccharides were detected after 48 h of α-amylase digestion. The *P. beijingensis* LMM product, however, appeared to be more susceptible to α-amylase digestion, as revealed by the decreased intensity of the spot corresponding to the polymeric material and the accumulation of HMM oligosaccharides. This result correlates well with the decreased molecular mass and lower amount of α(1→6) linkages of the LMM *P. beijingensis* GTFD product, compared to its HMM counterpart. As reported before, the IMMP GTFB product was also resistant to the action of the α-amylase, whereas the amylose substrate was completely degraded under the same conditions. Both *P. beijingensis* GTFD products and the *A. chroococcum* GTFD were resistant to the endo-α-1,6-hydrolase activity of dextranase, reflecting the absence of consecutive α(1→6) linkages in these polymers. In contrast, IMMP and dextran, which contain a linear backbone of α(1→6)-linked D-glucopyranosyl repeating units were efficiently hydrolyzed by the action of dextranase. Pullulanase specifically hydrolyses the α(1→6) linkages of pullulan, amylopectin, and other 4,6-branched polysaccharides. After treatment with pullulanase, the *P. beijingensis* GTFD and the *A. chroococcum* GTFD products were degraded into smaller oligosaccharides, reflecting the presence of alternating α(1→6)/α(1→4), and α(1→4,6) branching points in these polymers. IMMP was not hydrolyzed by the action of the pullulanase, which is in agreement with the presence of linear α(1→6) chains in its structure. More details of the precise structures of the *P. beijingensis* GTFD products were obtained by analysis of the oligosaccharides formed upon incubation of the HMM and LMM polymers with pullulanase M1 by HPAEC (FIG. 24). Incubation of the HMM *P. beijingensis* GTFD polymer with pullulanase yielded a mixture of MOS up to DP 11 (FIG. 24A), whereas in the case of the LMM *P. beijingensis* GTFD polymer additional peaks corresponding to MOSs up to DP14 were also identified (FIG. 24B). The digestion of the *A. chroococcum* GTFD polymer resulted in the formation of MOS of DP 2 to 5 (FIG. 24C) and confirmed that this α-glucan consists of maltose, maltotriose, maltotetraose and maltopentaose units connected via single α(1→6) bonds in linear or branched orientations. The identification of MOSs with higher DPs in the case of the HMM and LMM *P. beijingensis* GTFD products leads to structures containing longer linear α(1→4) sequences. The significant occurrence of MOSs of DP from 6 to 10 in the LMM *P. beijingensis* GTFD polysaccharide explains the observed partial digestion of this polymer by the action of α-amylase (FIG. 23A), which cleaves α(1→4)-linked glucans in an endo-type fashion.

Composite Models.

Using the data obtained by methylation analysis, NMR spectroscopy and enzymatic digestion studies composite models could be constructed, reflecting all major structural elements observed for the HMM and LMM *P. beijingensis* GTFD products (FIG. 25). Comparing with the *A. chroococcum* GTFD product the linear α(1→4)-linked sequences are longer for HMM (up to DP6 in de model) and even longer for LMM (up to DP 7 in the model). Although longer linear DPs of consecutive α(1→4) are observed in the pullulanase digestion analysis (DP11 for HMM and DP14 for LMM), the amounts are too low to be reflected in the composite model. For the *A. chroococcum* GTFD product the pullulanase digestion showed only up to DP5 linear α(1→4)-linked sequences.

Oligosaccharides Formed in Time by the *P. beijingensis* GTFD Enzyme from Maltoheptaose To gain a better understanding of the reaction mechanism of the *P. beijingensis* and *A. chroococcum* GTFD enzymes, both enzymes were incubated with maltoheptaose (G7), and the oligosaccharides formed in time were analyzed by HPAEC (FIG. 26). Incubation of G7 (slightly contaminated with G6 and G5) with the *P. beijingensis* GTFD enzyme yielded G1, G2 and two peaks corresponding to compounds of unknown structure with a higher DP eluting at 53.5 and 55.5 min at the early stage of the reaction (FIG. 26A). A small peak corresponding to G3 was also identified, whereas the amounts of G5 and G6 remained low. HPAEC analysis of MOS standards of DPs from 2 to 30 revealed that these two peaks of unidentified structure eluted slightly earlier than maltododecaose (G12) and maltotridecaose (G13), suggesting structures with DP of 12 and 13 and at least one α(1→6) linkage. The deficit observed in the G5 and G6 released, together with the formation of G1 and G2 indicates that the *P. beijingensis* GTFD enzyme catalyzes the transfer of maltopentaosyl- and maltohexaosyl-moieties to a G7 acceptor substrate, yielding the two unknown peaks (peaks eluting at 53.5 and 55.5 min). After 24 h, the unknown oligosaccharides initially formed by the *P. beijingensis* GTFD enzyme disappeared suggesting that these compounds can be subsequently used as donor and/or acceptor substrates. When exploring the activity of *A. chroococcum* GTFD, G2, G3 and two unknown compounds with high DP eluting at 51.4 and 53.5 min, were detected as the first clear products formed from G7 (FIG. 26B). The appearance of G2 and the peak eluting at 53.5 min, which was also observed in the case of *P. beijingensis* GTFD, indicates that the *A. chroococcum* GTFD also has the ability to catalyze a maltopentaosyl-transfer reaction from G7. The excess of G3, compared to G4, together with the identification of a peak eluting at 51.4 min, suggests that *A. chroococcum* GTFD is also able to cleave off a maltotetraosyl unit and transfer it to a MOS acceptor molecule. Most notably, the release of G1 as a side product of the maltohexaosyl-unit transfer reaction was not seen for the *A. chroococcum* GTFD during the early stage of the reaction. In agreement with this mode of action, the *A. chroococcum* GTFD activity on amylose results in the synthesis of a reuteran-like polymer built-up from MOS up to DP 5 linked by α(1→6) linkages. The preference for the transfer of longer glucan chains by the *P. beijingensis* GTFD enzyme is also reflected by the presence of longer linear α(1→4) sequences in the structure of its reuteran-like products. Overall these results indicate that the architecture of the active site of these GTFD type of enzymes may present more than one donor binding subsite, similar to other starch-converting enzymes of the evolutionary related GH13 and GH77 families (16-18). As a result, these GTFD enzymes have the ability to transfer MOS units, differing from GSs that strictly transfer a single glucose unit per reaction cycle. Differences in the number of donor substrate binding subsites may explain the differences observed in the length of the chains transferred by the *P. beijingensis* and the *A. chroococcum* GTFD enzymes.

Example 4: In Vitro Digestibility of Amylose Treated with *A. chroococcum* GTFD or *P. beijingensis* GTFD GTFD α-glucans were generated as described above (see section "Production and analysis of the products from amylose incubation with GTFD").

Preparation of Digestive Enzymes for Assay

Pancreatin from porcine pancreas (Sigma P7545) and intestinal acetone powders from rat (Sigma 11630) were extracted in 10 mM PBS solution (pH 6.8) at a 40 mg enzyme powders per mL concentration. Enzyme suspensions were vortex-mixed and sonicated in iced water for 7 min. Sonicated suspensions were then centrifuged at 10,000×g for 30 min at 4° C. and supernatants were collected separately.

Protein Content Measurements in Digestive Enzyme Preparations

Protein was quantified in the supernatants obtained from the enzyme extractions with the BCA (Bicinchoninic Acid) kit for protein determination (Sigma BCA1-1KT). Supernatants were diluted 10 times and protein contents were measured after reacting with BCA reagent for 30 min at 37° C. in a spectrophotometer at 562 nm wavelength. A standard curve was prepared with bovine serum albumin standards for the calculation of total protein content.

Measurements of Activity of Digestive Enzymes

A 1% solution of soluble starch from potato (Sigma S2004) was prepared in 10 mM PBS solution (pH 6.8). One hundred microliters of 1% soluble starch solution were added to 100 μl of pancreatin supernatant or rat intestinal acetone powders supernatant separately. Starch and enzyme mixtures were incubated at 37° C. for 10 min with constant stirring. Mixtures were subsequently heated at 100° C. for 10 min to stop the enzymatic reaction. After allowing the mixtures to cool down, sample tubes were centrifuged at 10,000×g for 10 min and glucose was measured via a colorimetric assay with the use of the Autokit Glucose (439-90901, Wako Diagnostics). One unit of enzyme activity was defined as the amount of protein required to hydrolyze 1 μg of glucose from soluble starch.

In Vitro Digestibility Measurements

1% (w/v) solutions of PbGTFD-HMM, PbGTFD-LMM, AcGTFD-HMM, Amylose V, and gelatinized wheat starch were incubated with 100 units of porcine pancreatin and rat intestinal powder extracts in 10 mM PBS (pH 6.8) for 20, 60, and 120 min at 37° C. with constant stirring in a total volume of 1.15 ml. After each time point, samples were subsequently heated at 100° C. for 10 min to stop the enzymatic reaction. After allowing the mixtures to cool down, sample tubes were centrifuged at 10,000×g for 10 min and glucose was measured via a colorimetric assay with the use of the Autokit Glucose (439-90901, Wako Diagnostics).

Results

The in vitro digestibility of the α-glucan products obtained from Amylose V incubation with PbGTFD and AcGTFD enzymes was considerably reduced in comparison to gelatinized wheat starch in both rate and extent of digestion. As can be observed from FIG. 28, the enzyme products from Amylose V incubations had a total digestibility of only 10%, 22% and 30% for AcGTFD-HMM, PbGTFD-HMM and Pb-GTFD-LMM, respectively, after 120 min of incubation with porcine pancreatin and rat intestinal powder extracts. Although the initial rates (at 20 min time point) were comparable among the 3 enzyme products, it is evident that both high-molecular mass α-glucans had lower digestibility than the *P. beijingensis* GTFD low-molecular mass product. All the α-glucan products had a lower digestibility than Amylose V (not plotted).

Overall Conclusions

In this study we report the characterization of the GTFD enzyme of *A. chroococcum* NCIMB 8003, providing the first example of a family GH70 enzyme in a Gram-negative bacterium. Regarding its amino acid sequence and domain organization, this enzyme is closely related to the *E. sibiricum* 255-15 GTFC, the first characterized member of a recently identified novel GH70 subfamily found in non-lactic acid bacteria (Gangoiti et al., 2015). GTFC type of enzymes are considered evolutionary intermediates between families GH13 and GH70, displaying 4,6-α-glucanotransferase activity with malto-oligosaccharides and amylose/starch, as previously found for the GTFB type of enzymes of lactobacilli. The *E. sibiricum* GTFC enzyme activity results in synthesis of isomalto/malto-oligosaccharides which consist of linear α(1→6)-glucan chains attached to the nonreducing ends of MOS or starch fragments. In contrast, the *A. chroococcum* GTFD enzyme is unable to synthesize consecutive α(1→6) linkages and converts amylose V into an α-glucan with alternating α(1→4) and α(1→6) glucosidic bonds, and with α(1→4,6) branching points. The GTFD polymer produced from amylose V thus is more similar to the reuteran produced from sucrose by the *L. reuteri* GTFA glucansucrase (Kralj et al., 2004; van Leeuwen et al., 2008a; Dobruchowska et al., 2013).

The *A. chroococcum* GTFD is the first enzyme reported so far able to synthesize a reuteran-like polymer from amylose and/or starch. This GTFD enzyme is different from other starch-converting enzymes such as the family GH13 and GH57 branching enzymes that only introduce α(1→6) branching points (Grimaud et al., 2014; Palomo et al., 2011) or the family GH15 dextrin dextrinases that synthesize consecutive α(1→6) linkages (Naessens et al., 2005). Functionally, the *A. chroococcum* GTFD also differed from *L. reuteri* 121 GTFB and *E. sibiricum* GTFC in its mechanism of polymerization as it preferentially transfers an oligosaccharide per reaction cycle, visible in FIG. 10, instead of a single glucose unit. In view of this feature the active site organization in *A. chroococcum* GTFD is predicted to present more than one donor substrate binding subsite, similar to the GH13 α-amylases. Overall, the *A. chroococcum* GTFD enzyme is a unique evolutionary intermediate between family GH13 and GH70 enzymes (FIG. 2) that considerably expands our knowledge about the natural diversity of family GH70 members.

The *A. chroococcum* GTFD enzyme represents a powerful tool for the conversion of the starch present in food matrices into a health promoting food ingredient. Indeed, reuteran has been described as a potentially valuable food ingredient being regarded as a dietary fiber. Due to its highly branched structure, reuteran resists enzymatic degradation in the upper gastrointestinal tract and ends up in the large intestine where it can be fully fermented by the colonic microflora. In addition, it appears that reuteran enhances satiety in humans or animals (Ekhart et al., 2006), and can be used as a bread improver (Plijter et al., 2009). The in vivo role of this *A. chroococcum* GTFD reuteran-like polymer is unknown. It has been proposed that EPS provides protection to cells against desiccation and predation by protozoans or phage attack (Flemming & Wingender, 2010). Early studies reported that *A. chroococcum* strains NCIMB 8003 and NRRL B-14341 produce at least two exocellular polysaccharides, one which resembles alginate and a heteropolysaccharide (Lawson & Stacey, 1954; Cote et al., 1988). Following growth of *A. chroococcum* NRRL B-14341 on starch the same exopolysaccharides were isolated (Cote et al., 1988). Studies in *A. vinelandii* have demonstrated that alginates are essential for cyst formation (Nunez et al., 1999), and play a role in the protection of the $O_2$-sensitive nitrogenase responsible of nitrogen fixation (Sabra et al., 2000). The *A. chroococcum* GTFD may have a related physiological function.

We also report on the characterization of the GTFD enzyme of *P. beijingensis* DSM 24997, a further enzyme able to synthesize a reuteran-like polymer from amylose and/or starch. Whereas the *A. chroococcum* GTFD activity on amylose results in the synthesis of a high molecular polymer, in addition to maltose and other small oligosaccharides, two reuteran-like polymer distributions are produced by *P. beijingensis* GTFD: a high-molecular mass polymer with an average Mw of 27 MDa and a low-molecular mass polymer with an average Mw of 19000 Da. Besides, *P. beijingensis* GTFD is able to transfer longer MOS units than the *A. chroooccum* counterpart yielding reuteran polymers containing longer linear α(1→4) sequences. From in vitro digestibility studies, all these polymers show a lower digestibility by digestive enzymes, providing strong support for the application of these enzymes for the reduction of glycemic Index of starchy products.

REFERENCES

Y. Bai, R. M. van der Kaaij, A. J. Woortman, Z. Jin, L. Dijkhuizen (2015a) Characterization of the 4,6-α-glucanotransferase GTFB enzyme of *Lactobacillus reuteri* 121 isolated from inclusion bodies. BMC Biotechnol. 15:49. DOI 10.1186/s12896-015-0163-7

Y. Bai, R. M. van der Kaaij, H. Leemhuis, S. S. van Leeuwen, Z. Jin, L. Dijkhuizen (2015b)—Biochemical characterization of *Lactobacillus reuteri* Glycoside Hydrolase Family 70 GTFB type of 4,6-α-glucanotransferase enzymes that synthesize soluble dietary starch fibers. Appl Environ Microbiol., in press.

K. Bath, S. Roos, T. Wall, H. Jonsson (2005)—The cell surface of *Lactobacillus reuteri* ATCC 55730 highlighted by identification of 126 extracellular proteins from the genome sequence. FEMS Microbiol Lett 253: 75-82.

Y. Brison, T. Pijning, Y. Malbert, E. Fabre, L. Mourey, S. Morel, G. Potocki-Véronèse, P. Monsan, S. Tranier, M. Remaud-Siméon, B. W. Dijkstra (2012)—Functional and structural characterization of an α-(1-2) branching sucrase derived from DSR-E glucansucrase. J Biol Chem. 287: 7915-7924.

G. L. Cote, L. H. Krull (1988)—Characterization of the exocellular polysaccharides from *Azotobacter chroococcum*. Carbohydr Res. 181: 143-152.

J. M. Dobruchowska, G. J. Gerwig, S. Kralj, P. Grijpstra, H. Leemhuis, L. Dijkhuizen, J. P. Kamerling. 2012. Structural characterization of linear isomalto-/malto-oligomer products synthesized by the novel GTFB 4,6-alpha-glucanotransferase enzyme from *Lactobacillus reuteri* 121. Glycobiology 22: 517-528.

J. M. Dobruchowska, X. Meng, H. Leemhuis, G. J. Gerwig, L. Dijkhuizen, J. P. Kamerling (2013)—Gluco-oligomers initially formed by the reuteransucrase enzyme of *Lactobacillus reuteri* 121 incubated with sucrose and malto-oligosaccharides. Glycobiology 23: 1084-1096.

L. Dijkhuizen, M. J. E. C. Van der Maarel, J. P. Kamerling, R. J. Leemhuis, S. Kralj, J. M. Dobruchowska (2010)—Glucooligosaccharides comprising (alpha 1→4) and (alpha 1→6) glycosidic bonds, use thereof, and methods for producing them. EP 2 427 565 B1.

P. Ekhart, G. H. van Geel-Schutten, M. Van Binsbergen, E. Timmerman (2006)—Branched alpha-glucans for weight management. US 20060100171 A1.

H. C. Flemming, J. Wingender (2010)—The biofilm matrix source. Nat Rev Microbiol. 8: 623-633.

J. Gangoiti, T. Pijning, L. Dijkhuizen (2015)—Biochemical characterization of the *Exiguobacterium sibiricum* 255-15 GTFC enzyme representing a novel glycoside hydrolase 70 subfamily of 4,6-α-glucanotransferase enzymes. Appl Environ Microbiol., submitted.

F. Grimaud, C. Lancelon-Pin, A. Rolland-Sabaté, X. Roussel, S. Laguerre, A. Viksø-Nielsen, J. L. Putaux, S. Guilois, A. Buléon, C. D'Hulst, G. Potocki-Véronèse.

(2013)—In vitro synthesis of hyperbranched α-glucans using a biomimetic enzymatic toolbox. Biomacromolecules. 14: 438-447.

K. Ito, S. Ito, T. Shimamura, S. Weyand, Y. Kawarasaki, T. Misaka, K. Abe, T. Kobayashi, A. D. Cameron, S. Iwata (2011)—Crystal structure of glucansucrase from the dental caries pathogen *Streptococcus mutans*. J Biol Chem. 408: 177-186.

S. Kralj, P Grijpstra, S. S. van Leeuwen, H. Leemhuis, J. M. Dobruchowska, R. M. van der Kaaij, A. Malik, A. Oetari, J. P. Kamerling, L. Dijkhuizen (2011)—4,6-alpha-glucanotransferase, a novel enzyme that structurally and functionally provides an evolutionary link between glycoside hydrolase enzyme families 13 and 70. Appl Environ Microbiol. 77: 8154-8163.

S. Kralj, G. H. van Geel-Schutten, H. Rahaoui, R. J. Leer, E. J. Faber, M. J. van der Maarel, Dijkhuizen L. (2002)—Molecular characterization of a novel glucosyltransferase from *Lactobacillus reuteri* strain 121 synthesizing a unique, highly branched glucan with alpha-(1→4) and alpha-(1→6) glucosidic bonds Appl Environ Microbiol. 68: 4283-4291.

S. Kralj, G. H. van Geel-Schutten, M. J. E. C. van der Maarel and L. Dijkhuizen (2004)—Biochemical and molecular characterization of *Lactobacillus reuteri* 121 reuteransucrase. Microbiology 150: 2099-2112.

S. Kralj, E. Stripling, P. Sanders, G. H. van Geel-Schutten, L. Dijkhuizen (2005)—Highly hydrolytic reuteransucrase from probiotic *Lactobacillus reuteri* strain ATCC 55730. Appl Environ Microbiol. 71: 3942-3950.

G. L. Lawson, M. Stacey (1954) Immunopolysaccharides. I. Preliminary studies of a polysaccharide from *Azotobacter chroococcum* containing an uronic acid. J Chem Soc. 1954: 1925-1931.

H. Leemhuis, W. P. Dijkman, J. M. Dobruchowska, T. Pijning, P. Grijpstra, S. Kralj, J. P. Kamerling, L. Dijkhuizen (2013)—4,6-α-Glucanotransferase activity occurs more widespread in *Lactobacillus* strains and constitutes a separate GH70 subfamily. Appl Microbiol Biotechnol. 97: 181-193.

H. Leemhuis, J. M. Dobruchowska, M. Ebbelaar, F. Faber, P. L. Buwalda, M. J. E. C. van der Maarel, J. P. Kamerling, L. Dijkhuizen (2014)—Isomalto/Malto Polysaccharide, a novel soluble dietary fiber made via enzymatic conversion of starch. J Agric Food Chem. 62: 12034-12044.

V. Lombard, H. Golaconda Ramulu, E. Drula, P. M. Coutinho, B. Henrissat (2014)—The carbohydrate-active enzymes database (CAZy) in 2013. Nucleic Acids Res. 42: D490-495.

E. A. MacGregor, S. Janecek, B. Svensson. (2001)—Relationship of sequence and structure to specificity in the alpha-amylase family of enzymes. Biochim Biophys Acta 1546: 1-20.

E. A. MacGregor, H. M. Jespersen, B. Svensson (1996)—A circularly permuted alpha-amylase-type alpha/beta-barrel structure in glucan-synthesizing glucosyltransferases. FEBS Lett. 378: 263-266.

X. Meng, J. M. Dobruchowska, T. Pijning, C. A. López, J. P. Kamerling, L. Dijkhuizen (2014) Residue Leu940 has a crucial role in the linkage and reaction specificity of the glucansucrase GTF180 of the probiotic bacterium *Lactobacillus reuteri* 180. J Biol Chem. 289: 32773-32782.

X. Meng, J. M. Dobruchowska, T. Pijning, G. J. Gerwig, J. P. Kamerling and L. Dijkhuizen (2015)—Truncation of domain V of the multidomain glucansucrase GTF180 of *Lactobacillus reuteri* 180 heavily impairs its polysaccharide-synthesizing ability. Appl Microbiol Biotechnol. 99: 5885-5894.

M. Naessens, A. Cerdobbel, W. Soetaert, E. J. Vandamme (2005)—Dextran dextrinase and dextran of *Gluconobacter oxydans*. J Ind Microbiol Biotechnol. 32: 323-334.

C. Nunez, S. Moreno, G. Soberon-Chavez, G. Espin (1999)—The *Azotobacter vinelandii* response regulator AlgR is essential for cyst formation. J Bacteriol. 181: 141-148.

M. Palomo, T. Pijning, T. Booiman, J. M. Dobruchowska, J. van der Vlist, S. Kralj, A. Planas, K. Loos, J. P. Kamerling, B. W. Dijkstra, M. J. van der Maarel, L. Dijkhuizen, H. Leemhuis (2011)—*Thermus thermophilus* glycoside hydrolase family 57 branching enzyme: crystal structure, mechanism of action, and products formed. J Biol Chem. 286: 3520-3530.

T. Pijning, A. Vujicic-Zagar, S. Kralj, L. Dijkhuizen, B. W. Dijkstra (2012)—Structure of the α-1,6/α-1,4-specific glucansucrase GTFA from *Lactobacillus reuteri* 121. Acta Cryst F. 68: 1448-1454.

J. Plijter, A. Jurgens, M. P. Kats, M. W. J. Noort, C. E. A. Heddes, G. H. Van Geel Schutten (2009) Bread improver US 20090297663 A1.

R. L. Robson, R. Jones, R. M. Robson, A. Schwartz, T. H. Richardson (2015)—*Azotobacter* Genomes: The Genome of *Azotobacter chroococcum* NCIMB 8003 (ATCC 4412). PLoS One. 10:e0127997. doi: 10.1371/journal.pone.

R. L. Robson, J. A. Chesshyre, C. Wheeler, R. Jones, P. R. Woodley, J. R. Postgate (1984)—Genome size and complexity in *Azotobacter chroococcum*. J Gen Microbiol. 130: 1603-1612.

R. L. Robson (1986)—Nitrogen fixation in strains of *Azotobacter chroococcum* bearing deletions of a cluster of genes coding for nitrogenase. Arch Microbiol. 146: 74-79.

W. Sabra, A. P. Zeng, H. Lünsdorf, W. D. Deckwer (2000)—Effect of oxygen on formation of *Azotobacter vinelandii* alginate and its role in protecting nitrogenase. Appl Environ Microbiol. 66: 4037-4044.

M. R. Stam, E. G. Danchin, C. Rancurel, P. M. Coutinho, B. Henrissat, (2006)—Dividing the large glycoside hydrolase family 13 into subfamilies: towards improved functional annotations of alpha-amylase-related proteins. Protein Eng Des Sel. 19: 555-562.

K. Tamura, G. Stecher, D. Peterson, A. Filipski, S. Kumar (2013)—MEGA6: Molecular Evolutionary Genetics Analysis version 6.0. Mol Biol Evol. 30: 2725-2729.

S. A. F. T. van Hijum, S. Kralj, L. K. Ozimek, L. Dijkhuizen, G. H. van Geel-Schutten (2006)—Structure-function relationships of glucansucrase and fructansucrase enzymes from lactic acid bacteria. Microbiol Mol Biol Rev. 70: 157-176.

S. S. van Leeuwen, S. Kralj, W. Eeuwema, G. J. Gerwig, L. Dijkhuizen, and J. P. Kamerling (2009)—Structural characterization of bioengineered alpha-D-Glucans produced by mutant glucansucrase GTF180 enzymes of *Lactobacillus reuteri* strain 180. Biomacromol. 10: 580-588.

S. S. van Leeuwen, S. Kralj, G. H. van Geel-Schutten, G. Gerwig, L. Dijkhuizen, J. P. Kamerling (2008a)—Structural analysis of the alpha-D-glucan (EPS35-5) produced by the *Lactobacillus reuteri* strain 35-5 glucansucrase GTFA enzyme. Carbohydr Res. 343: 1251-1265.

S. S. van Leeuwen, S. Kralj, I. H. van Geel-Schutten, G. J. Gerwig, L. Dijkhuizen, J. P. Kamerling (2008b)—Structural analysis of the α-D-glucan (EPS180) produced by the *Lactobacillus reuteri* strain 180 glucansucrase GTF180 enzyme. Carbohydr Res. 343: 1237-1250.

J. C. Uitdehaag, G. J. van Alebeek, B. A. van Der Veen, L. Dijkhuizen, B. W. Dijkstra. (2000)—Structures of maltohexaose and maltoheptaose bound at the donor sites of cyclodextrin glycosyltransferase give insight into the mechanisms of transglycosylation activity and cyclodextrin size specificity. Biochemistry 39: 7772-7780.

S. A. F. T. van Hijum, S. Kralj, L. K. Ozimek, L. Dijkhuizen, G. H. van Geel-Schutten (2006)—Structure-function relationships of glucansucrase and fructansucrase enzymes from lactic acid bacteria. Microbiol Mol Biol Rev. 70: 157-176.

A. Vujičić-agar, T. Pijning, S. Kralj, C. A. López, W. Eeuwema, L. Dijkhuizen, B. W. Dijkstra (2010)—Crystal structure of a 117 kDa glucansucrase fragment provides insights into evolution and product specificity of GH70 enzymes. Proc Natl Acad Sci. (USA) 107: 21406-21411.

A. M. Waterhouse, J. B. Procter, D. M. A. Martin, M. Clamp, G. J. Barton (2009)—Jalview Version 2—a multiple sequence alignment editor and analysis workbench. Bioinformatics. 25: 1189-1191.

---

The invention claimed is:

1. A method of producing an α-glucan with a ratio of branching of at least 8%, the method comprising;
   contacting an α-glucanotransferase with a polysaccharide or oligosaccharide substrate having degree of polymerization (DP) of at least 3,
   wherein the polysaccharide or oligosaccharide comprises at least two α(1→4) linked D-glucose residues at a non-reducing end and is selected from the group consisting of starch, starch derivatives, malto-oligosaccharides, amylose, amylopectin, maltodextrins, α(1→4) glucans and combinations thereof, and
   wherein the α-glucanotransferase comprises an amino acid sequence having at least 95% identity to SEQ ID NO:1.

2. The method according to claim 1, wherein the production of α-glucan is stopped before the reaction between the polysaccharide or oligosaccharide substrate and the α-glucanotransferase enzyme has reached completion.

3. The method according to claim 1, wherein the polysaccharide or oligosaccharide substrate is contacted with the α-glucanotransferase enzyme at a temperature of between 30° C. and 75° C. and a pH of between 4.8 and 8.0.

4. The method according to claim 1, wherein the α-glucan with a ratio of branching of at least 8% has less than 1.0% consecutive α(1→6) glucosidic linkages.

5. The method according to claim 1, wherein the α-glucan with a ratio of branching of at least 8% has less than 0.5% consecutive α(1→6) glucosidic linkages.

6. The method according to claim 1, wherein the α-glucan with a ratio of branching of at least 8% has no consecutive α(1→6) glucosidic linkages.

7. The method according to claim 1, wherein the α-glucanotransferase comprises an amino acid sequence having at least 96% identity to SEQ ID NO:1.

8. The method according to claim 1, wherein the α-glucanotransferase comprises an amino acid sequence having at least 97% identity to SEQ ID NO:1.

9. The method according to claim 1, wherein the α-glucanotransferase comprises an amino acid sequence having at least 98% identity to SEQ ID NO:1.

10. The method according to claim 1, wherein the α-glucanotransferase comprises an amino acid sequence having at least 99% identity to SEQ ID NO:1.

11. The method according to claim 1, wherein the α-glucanotransferase has an amino acid sequence of SEQ ID NO:1.

* * * * *